(12) United States Patent
Rochelle et al.

(10) Patent No.: US 9,321,007 B2
(45) Date of Patent: Apr. 26, 2016

(54) BLENDS OF AMINES WITH PIPERAZINE FOR $CO_2$ CAPTURE

(71) Applicant: BOARD OF REGENTS, THE UNIVERSITY OF TEXAS SYSTEM, Austin, TX (US)

(72) Inventors: Gary Rochelle, Austin, TX (US); Omkar Namjoshi, Baton Rouge, LA (US); Le Li, Austin, TX (US); Yang Du, Austin, TX (US); Thu Nguyen, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/335,138

(22) Filed: Jul. 18, 2014

(65) Prior Publication Data
US 2015/0073150 A1 Mar. 12, 2015

Related U.S. Application Data

(63) Continuation of application No. PCT/US2013/022603, filed on Jan. 22, 2013.

(60) Provisional application No. 61/589,092, filed on Jan. 20, 2012.

(51) Int. Cl.
*B01D 53/14* (2006.01)
*C07D 241/04* (2006.01)
*B01D 53/40* (2006.01)

(52) U.S. Cl.
CPC .......... *B01D 53/40* (2013.01); *B01D 53/1456* (2013.01); *B01D 53/1475* (2013.01); *B01D 53/1493* (2013.01); *C07D 241/04* (2013.01); *B01D 2252/103* (2013.01); *B01D 2252/2041* (2013.01); *B01D 2252/20415* (2013.01); *B01D 2252/20421* (2013.01); *B01D 2252/20426* (2013.01); *B01D 2252/20431* (2013.01); *B01D 2252/20447* (2013.01); *B01D 2257/304* (2013.01); *B01D 2257/306* (2013.01); *B01D 2257/308* (2013.01); *B01D 2257/504* (2013.01); *B01D 2258/0283* (2013.01); *Y02C 10/06* (2013.01); *Y02P 20/152* (2015.11)

(58) Field of Classification Search
CPC ........ B01D 53/14; B01D 53/40; B01D 53/62; C07D 241/04
See application file for complete search history.

(56) References Cited

U.S. PATENT DOCUMENTS

| | | | |
|---|---|---|---|
| 8,070,856 B2 * | 12/2011 | Cullinane et al. | ............... 95/236 |
| 2008/0125314 A1 | 5/2008 | Shim et al. | |
| 2009/0068078 A1 | 3/2009 | Grobys et al. | |
| 2009/0211446 A1 | 8/2009 | Rochelle et al. | |
| 2010/0204042 A1 | 8/2010 | Asprion | |
| 2010/0326277 A1 | 12/2010 | Chung et al. | |
| 2011/0171093 A1 * | 7/2011 | Freeman et al. | .............. 423/228 |
| 2011/0232489 A1 | 9/2011 | Holub et al. | |

* cited by examiner

*Primary Examiner* — Andrew D Kosar
*Assistant Examiner* — John S Kenyon
(74) *Attorney, Agent, or Firm* — Reed Smith LLP; Robert R. Riddle; Matthew S. Gibson

(57) ABSTRACT

Compositions and methods related to the removal of acidic gas. In particular, the present disclosure relates to a composition and method for the removal of acidic gas from a gas mixture using a solvent comprising a blend of piperazine and at least one diamine or triamine.

7 Claims, 38 Drawing Sheets

1,4-diaminobutane (or putrescine) (DAB)

2-(2-aminoethoxy)ethanamine. (BAE)

Hexamethylenediamine (HMDA)

Piperazine (PZ)

Aminoethylpiperazine (AEP)

BLENDS OF AMINES WITH PIPERAZINE FOR $CO_2$ CAPTURE

CROSS-REFERENCE TO RELATED APPLICATIONS

This application is a continuation of PCT/US2013/022603 filed Jan. 22, 2013 and claims the benefit of U.S. Provisional Patent Application Ser. No. 61/589,092 filed Jan. 20, 2012, which are incorporated herein by reference.

BACKGROUND

As concerns of global climate changes spark initiatives to reduce carbon dioxide emissions, its economic removal from gas streams is becoming increasingly important. Removal by absorption/stripping is a commercially promising technology, as it is well suited to sequester carbon dioxide ($CO_2$). Such carbon dioxide emissions may be produced by a variety of different processes, such as the gas stream produced by coal-fired power plants. The removal of $CO_2$ can be an expensive process, potentially increasing the cost of electricity by 50% or more. Therefore, technology improvements to reduce the costs associated with the removal of $CO_2$ are highly desirable.

The use of absorption and stripping processes with aqueous solvents such as alkanolamines and promoted potassium carbonate is a known, effective technology for the removal and capture of $CO_2$ from flue gas, natural gas, hydrogen, synthesis gas, and other gases. U.S. Pat. Nos. 4,477,419 and 4,152,217, each of which is incorporated herein by reference, describe aspects of this technology. The first generation of technology relating to alkanolamine absorption/stripping uses aqueous solutions of monoethanolamine (MEA). Advances in this technology have provided other alkanolamine solvents for $CO_2$ treating in various industries. Monoethanolamine (MEA), diethanolamine (DEA), and the hindered amine aminomethylpropanol (AMP) are used alone in an aqueous solution. Typical solvent blends include a methyldiethanolamine (MDEA) solution promoted by piperazine or other secondary amines. Also, potassium carbonate solvents are commonly promoted by DEA or other reactive amines.

Gas absorption is a process in which soluble components of a gas mixture are dissolved in a liquid. Stripping is essentially the inverse of absorption, as it involves the transfer of volatile components from a liquid mixture into a gas. In a typical $CO_2$ removal process, absorption is used to remove $CO_2$ from a combustion gas, and stripping is subsequently used to regenerate the solvent and capture the $CO_2$ contained in the solvent. Once $CO_2$ is removed from combustion gases and other gases, it can be captured and compressed for use in a number of applications, including sequestration, production of methanol, and tertiary oil recovery.

The conventional method of using absorption/stripping processes to remove $CO_2$ from gaseous streams is described in U.S. Pat. No. 4,384,875, which is incorporated herein by reference. In the absorption stage, the gas to be treated, containing the $CO_2$ to be removed, is placed in contact, in an absorption column, with the chosen absorbent under conditions of pressure and temperature such that the absorbent solution removes virtually all the $CO_2$. The purified gas emerges at the top of the absorption column and, if necessary, it is then directed towards a scrubber employing sodium hydroxide, in which the last traces of $CO_2$ are removed. At the bottom of the absorption column, the absorbent solution containing $CO_2$ (also called "rich solvent") is drawn off and subjected to a stripping process to free it of the $CO_2$ and regenerate its absorbent properties. Other methods of using absorption/stripping process to remove $CO_2$ from gaseous stream are described in U.S. Patent Application Publication No. 2011/0171093, U.S. Pat. No. 7,938,887, and U.S. Provisional Patent Application Ser. No. 61/585,865, and U.S. patent application Ser. No. 13/740,874, the entireties of which are hereby incorporated by reference.

To effect the regeneration of the absorbent solution, the rich solvent drawn off from the bottom of the absorption column is introduced into the upper half of a stripping column, and the rich solvent is maintained at its boiling point under pressure in this column. The heat necessary for maintaining the boiling point is furnished by reboiling the absorbent solution contained in the stripping column. The reboiling process is effectuated by indirect heat exchange between part of the solution to be regenerated located in the lower half of the stripping column and a hot fluid at appropriate temperature, generally saturated water vapor. In the course of regeneration, the $CO_2$ contained in the rich solvent is released and stripped by the vapors of the absorbent solution. Vapor containing the stripped $CO_2$ emerges at the top of the stripping column and is passed through a condenser system which returns to the stripping column the liquid phase resulting from the condensation of the vapors of the absorbent solution. At the bottom of the stripping column, the hot regenerated absorbent solution (also called "lean solvent") is drawn off and recycled to the absorption column after having used part of the heat content of the solution to heat, by indirect heat exchange, the rich solvent to be regenerated, before its introduction into the stripping column.

In simple absorption/stripping as it is typically practiced in the field, aqueous rich solvent is regenerated at 100-160° C. in a simple, countercurrent, reboiled stripper operated at a single pressure, which is usually 1-10 atm. The rich solvent feed is preheated by cross-exchange with hot lean solvent to within 5-30° C. of the stripper bottoms. The overhead vapor is cooled to condense water, which is returned as reflux to the countercurrent stripper. When used for $CO_2$ sequestration and other applications, the product $CO_2$ is compressed to 100-150 atm.

Commercially used amines that are used by themselves in water as absorbers include monoethanolamine, diethanolamine, methyldiethanolamine, diglycolamine, diisopropanolamine, some hindered amines, and others (Kohl and Nielsen (1997)). These amines are soluble or miscible with water at ambient temperature at high concentrations that are used in the process to maximize capacity and reduce sensible heat requirements. Other amines, including piperazine, are used in combination with methyldiethanolamine and other primary amines.

A number of mono- and polyamines, including piperazine, are identified as potentially useful solvent components but have limited use because they are insufficiently soluble in water when used by themselves. However, certain blends of piperazine with other amines are known to have problems with solid precipitation. It is desirable to provide a blend of piperazine with another amine that does not suffer from solid precipitation.

SUMMARY

The present disclosure generally relates to the removal of acidic gases, including carbon dioxide and hydrogen sulfide, from flue gas or other gases through aqueous absorption and stripping processes. More particularly, in some embodiments, the present disclosure relates to methods and compositions for the removal of acidic gas from a gas mixture using an aqueous amine solvent blend.

In one embodiment, the present disclosure provides an aqueous amine solvent comprising piperazine and one or more amines selected from the group consisting of: hexamethylenediamine, putrescine, bis(aminoethyl)ether, and aminoethylpiperazine.

In one embodiment, the present disclosure provides an aqueous amine solvent comprising piperazine and a linear diamine, wherein the linear diamine comprises at least one of the following between the amine groups on the linear diamine: at least 4 carbon atoms and at least 4 oxygen atoms.

In another embodiment, the present disclosure provides a method comprising contacting an acidic gas with an aqueous amine solvent, wherein the aqueous amine solvent comprises piperazine and one or more amines selected from the group consisting of: hexamethylenediamine, putrescine, bis(aminoethyl)ether, and aminoethylpiperazine.

In another embodiment, the present disclosure provides a method comprising contacting an acidic gas with an aqueous amine solvent, wherein the aqueous amine solvent comprises piperazine and a linear diamine, wherein the linear diamine comprises at least one of the following between the amine groups on the linear diamine: at least 4 carbon atoms and at least 4 oxygen atoms.

In another embodiment, the present disclosure provides a method comprising contacting an acidic gas with a blend comprising piperazine and aminoethylpiperazine.

In another embodiment, the present disclosure provides a method comprising reacting monoethanolamine with piperazine and $CO_2$ in aqueous solution.

In another embodiment, the present disclosure provides a method comprising reacting piperazine with an alkanolamine at a temperature in the range of from about 100° C. to about 200° C.

The features and advantages of the present invention will be readily apparent to those skilled in the art. While numerous changes may be made by those skilled in the art, such changes are within the spirit of the invention.

DRAWINGS

Figure 31:
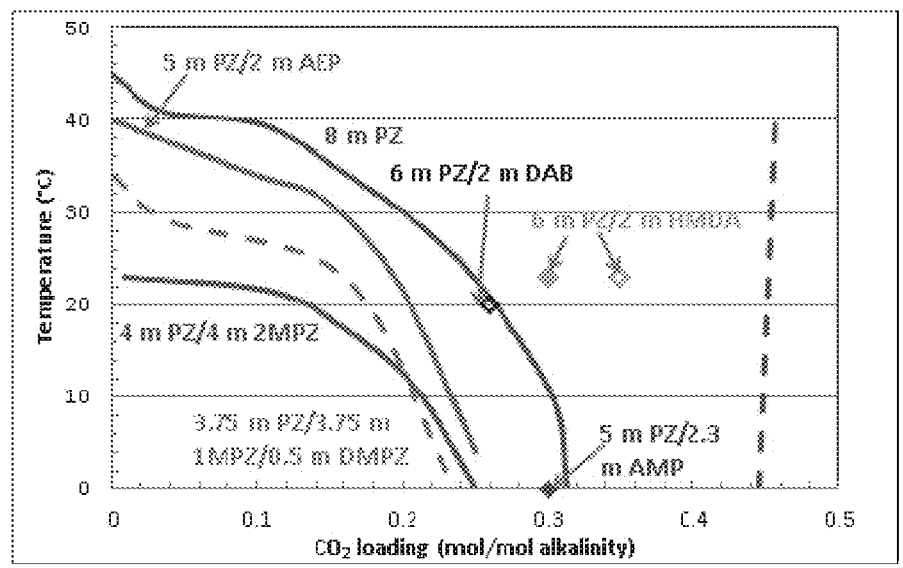

FIG. 31 shows the solid/liquid boundary of 8 m PZ and PZ blends. Solid lines: transition temperature vs. loading. Dash lines: at proximity to transition boundary, within which the solvent is soluble. Empty points: the blends are soluble at this loading or higher. Solid points: the blends are not soluble at this loading or lower.

Figure 32:
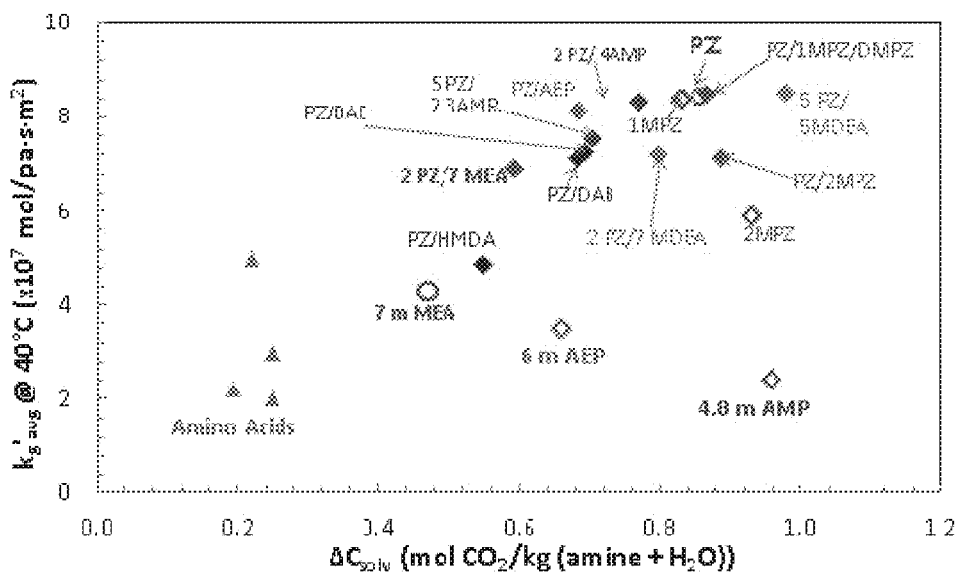

FIG. 32 shows comparison of absorption rates and solvent capacity for PZ blends and other solvents for coal flue gas. Filled diamonds: PZ blends; Empty diamonds: amine solvents; Empty circles: base case solvents 7 m MEA and 8 m PZ; Triangles: amino acid salts.

Figure 33:
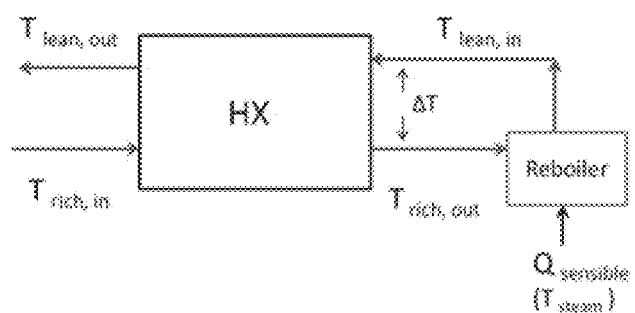

FIG. 33 is a diagram of cross-exchanger temperatures.

Figure 34:
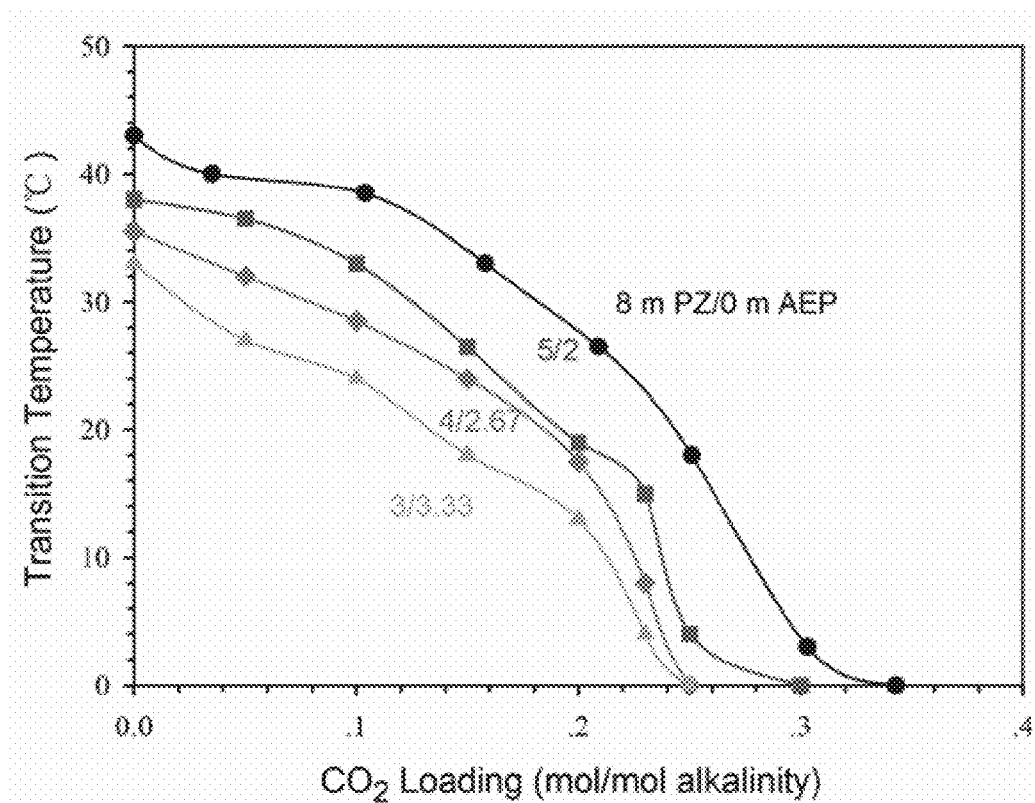

FIG. 34 shows liquid-solid transition temperature for PZ/AEP with different amine ratios, ○: 8 m PZ/0 m AEP; ■: 5 m PZ/2 m AEP; ♦: 4 m PZ/2.67 m AEP; ▲: 3 m PZ/3.33 m AEP.

Figure 35:
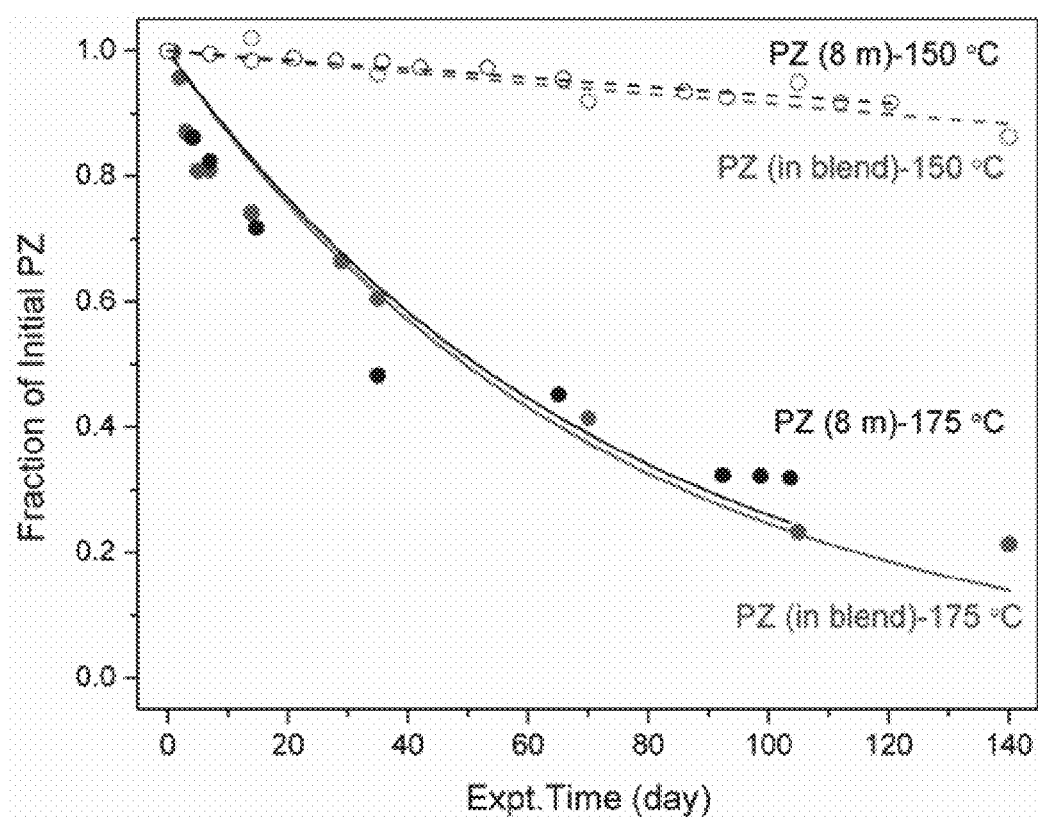

FIG. 35 is a comparison of PZ loss in 5 m PZ/2 m AEP and 8 m pure PZ in thermal degradation at 0.3 mol $CO_2$/mol alkalinity.

Figure 36:
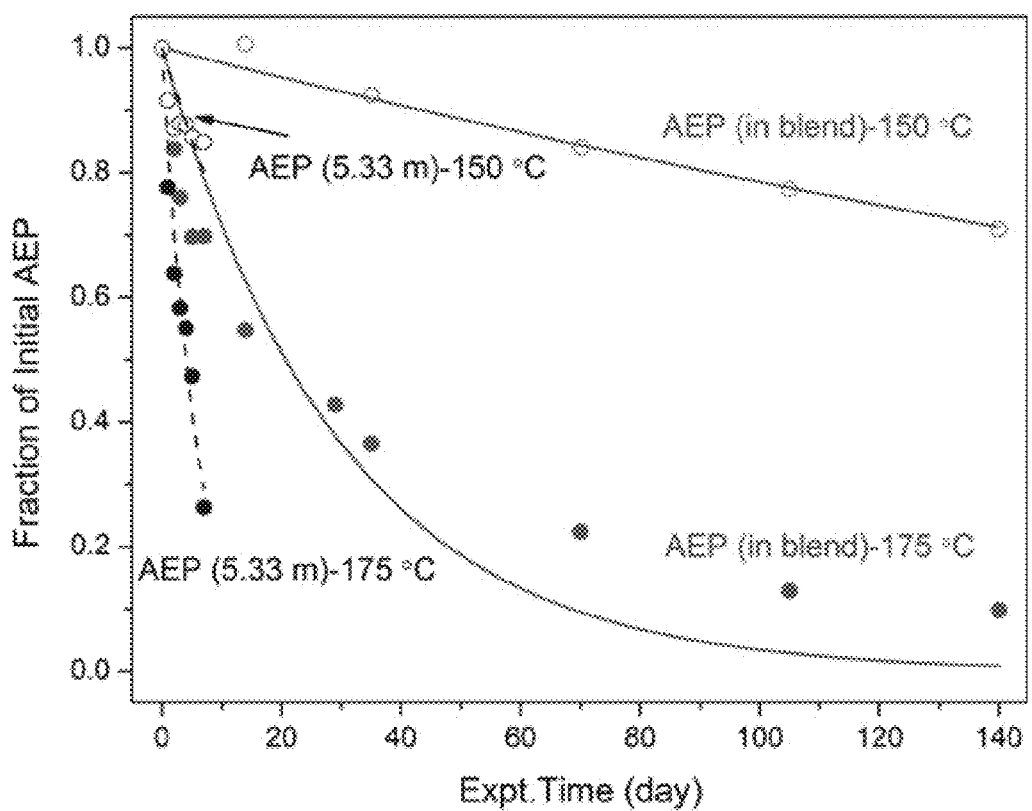

FIG. 36 shows a comparison of AEP loss in 5 m PZ/2 m AEP and 5.33 m pure AEP in thermal degradation at 0.3 mol $CO_2$/mol alkalinity.

Figure 37:
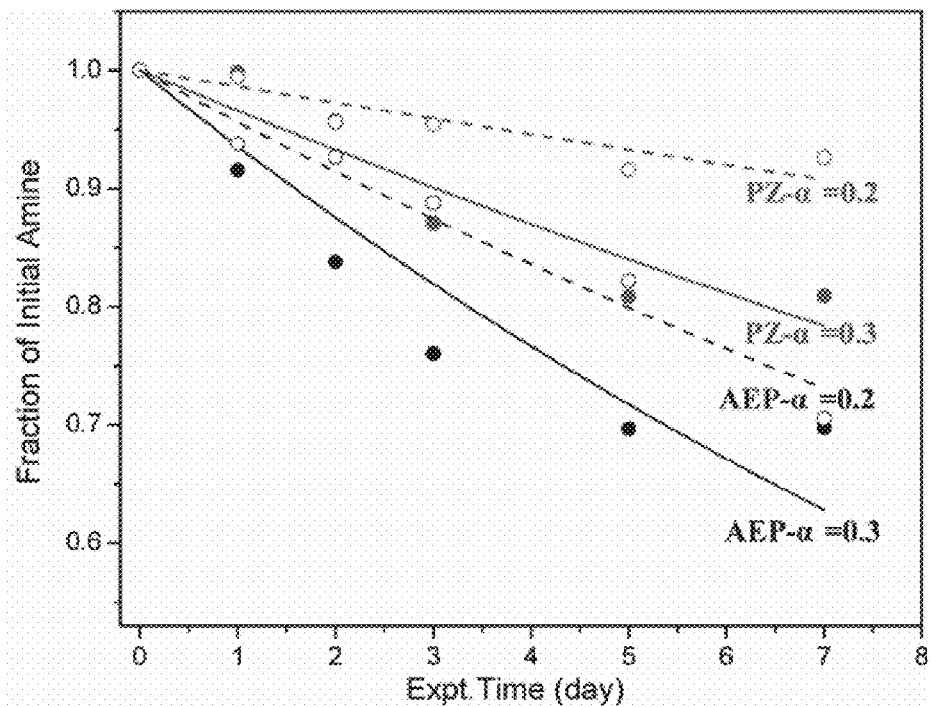

FIG. 37 shows effect of $CO_2$ on the degradation of PZ and AEP in 5 m PZ/2 m AEP at 175° C. (Dashed line: 0.2 mol $CO_2$/mol alkalinity; solid line: 0.3 mol $CO_2$/mol alkalinity).

Figure 38:
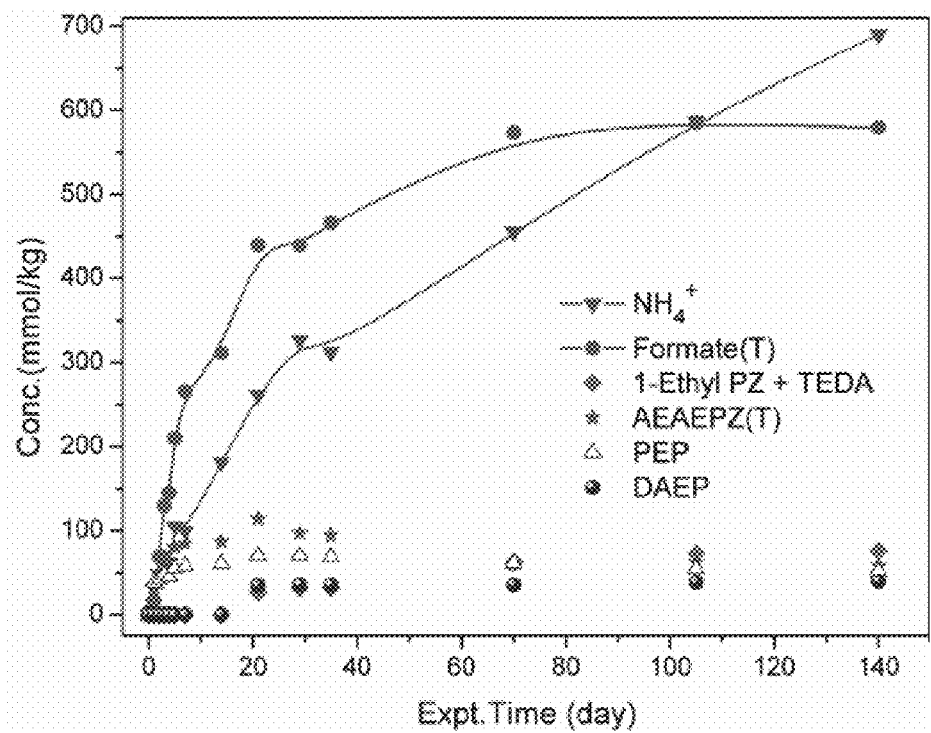

FIG. 38 shows degradation products from thermal degradation of 5 m PZ/2 m AEP with 0.3 mol $CO_2$/mol alkalinity at 175° C.

Figure 39:
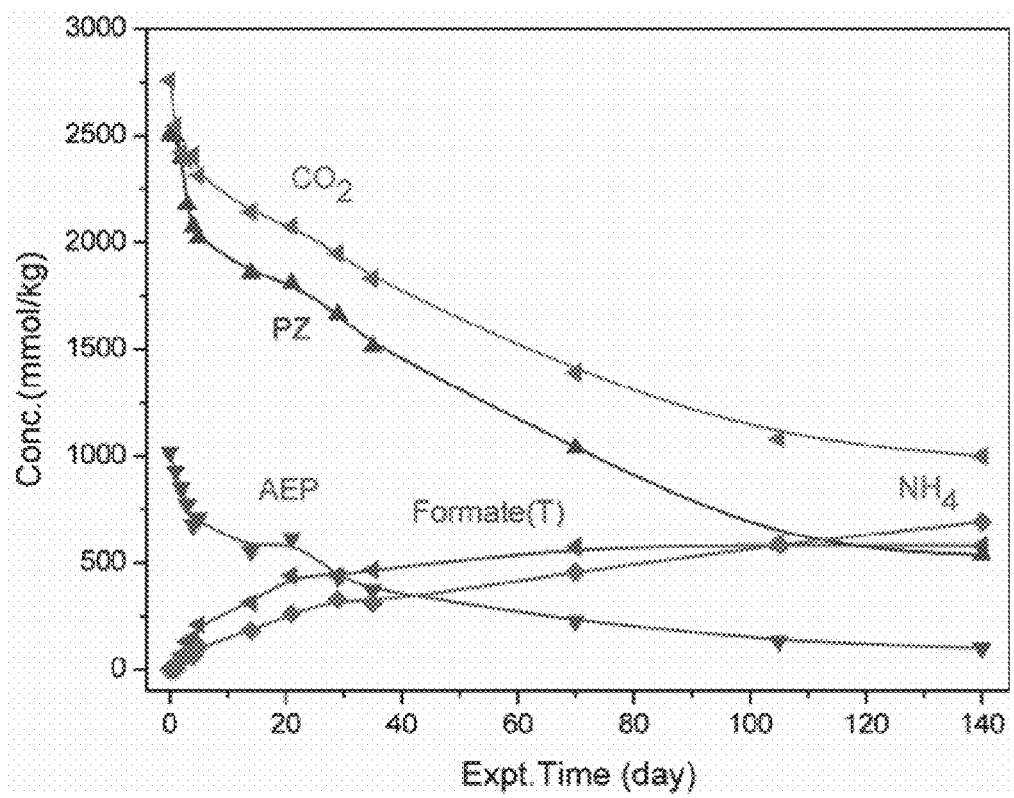

FIG. 39 shows PZ, AEP, and $CO_2$ loss and generation of major degradation products for 5 m PZ/2 m AEP with 0.3 mol $CO_2$/mol alkalinity at 175° C.

Figure 40:
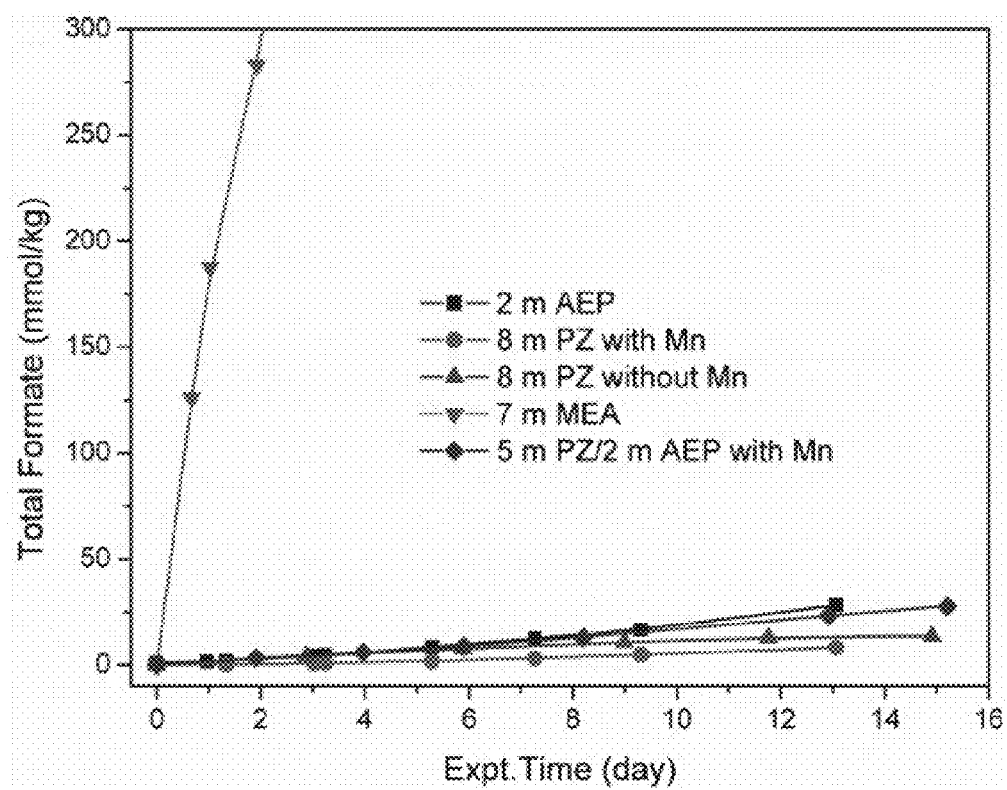

FIG. 40 shows a comparison of total formate production in 8 m PZ with $Mn^{2+}$, 8 m PZ without $Mn^{2+}$, 2 m AEP and 7 m MEA at 70° C.

Figure 41:
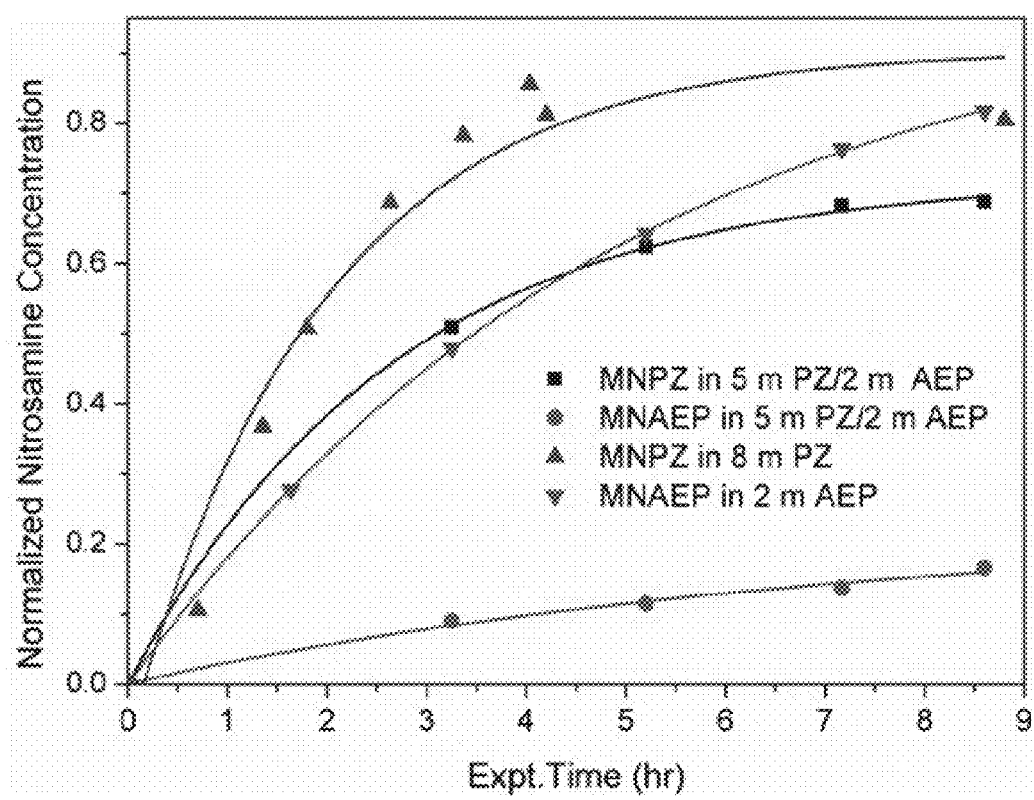

FIG. 41 shows nitrosamines formation in 5 m PZ/2 m AEP at 100° C., compared to that in 8 m PZ and 2 m AEP.

Figure 42:
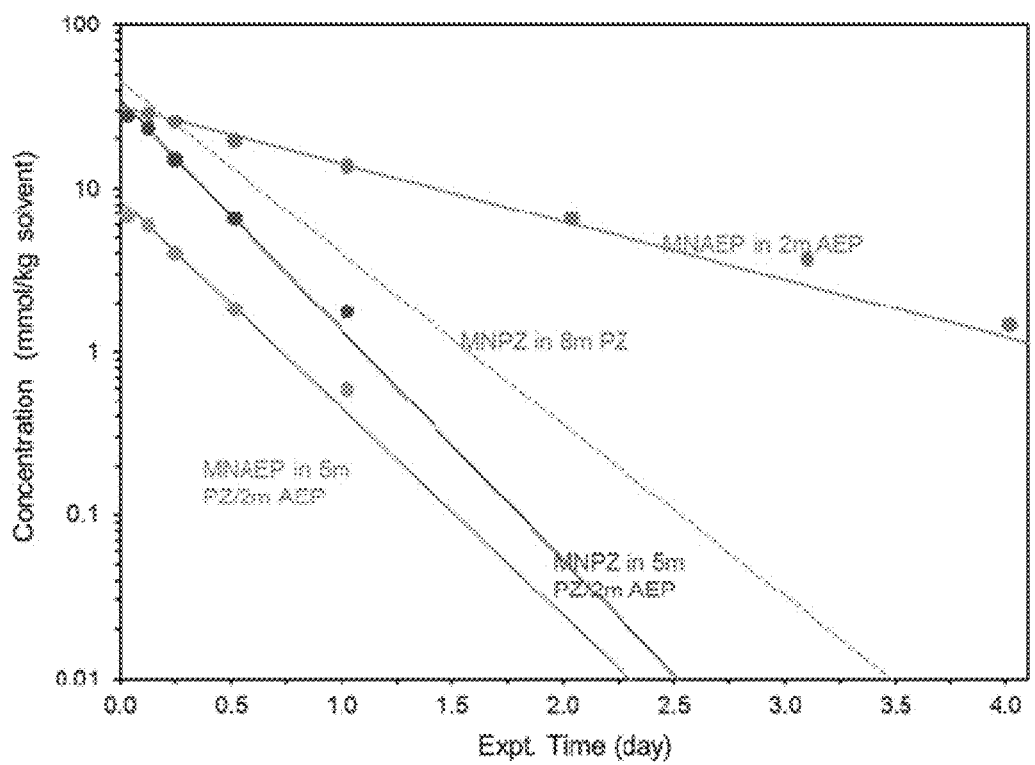

FIG. 42 shows nitrosamine decomposition in 5 m PZ/2 m AEP at 150° C., compared to that in 8 m PZ [8] and 2 m AEP.

Figure 43:
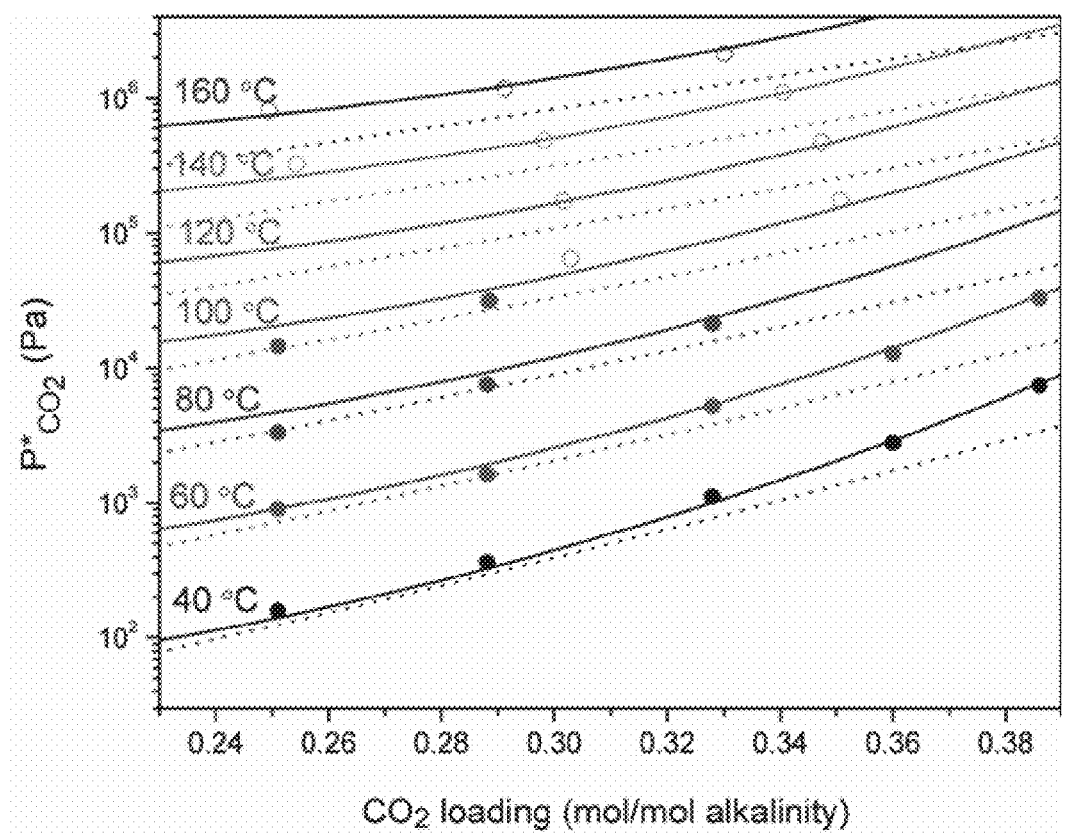

FIG. 43 shows $CO_2$ solubility for 5 m PZ/2 m AEP (Solid lines: 5 m PZ/2 m AEP equation model; Solid circles: measured data for 5 m PZ/2 m AEP using WWC; Open circles: measured data for 5 m PZ/2 m AEP using SA; Dashed lines: 8 m PZ equation model from Xu (Xu Q. Thermodynamics of $CO_2$ Loaded Aqueous Amines. The University of Texas at Austin, Austin, Tex., 2011).

Figure 44:
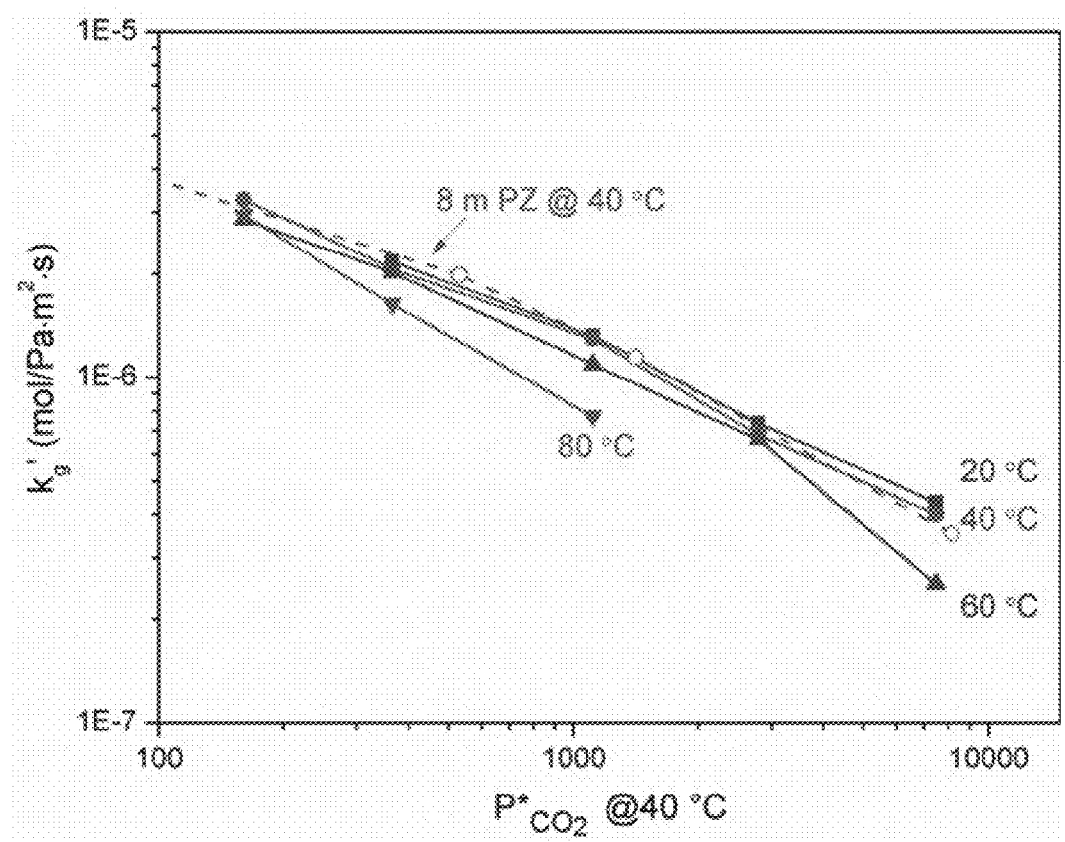

FIG. 44 shows mass transfer coefficients (kg') in 5 m PZ/2 m AEP (solid lines) from 20 to 80° C., compared to that in 8 m PZ (dashed line) at 40° C.

Figure 45:
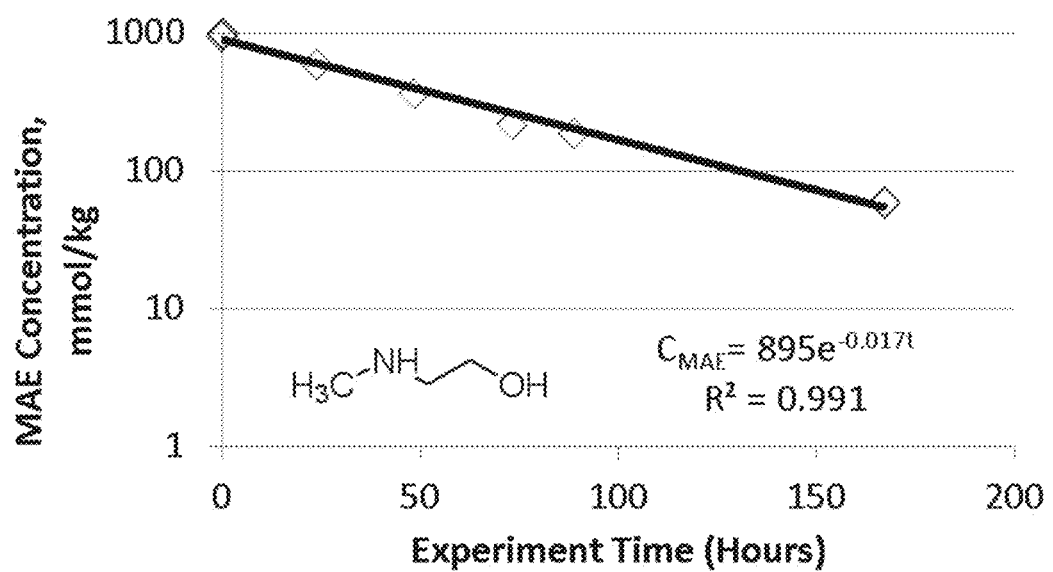

FIG. 45 shows concentration of MAE over time at 150° C.

Figure 46:
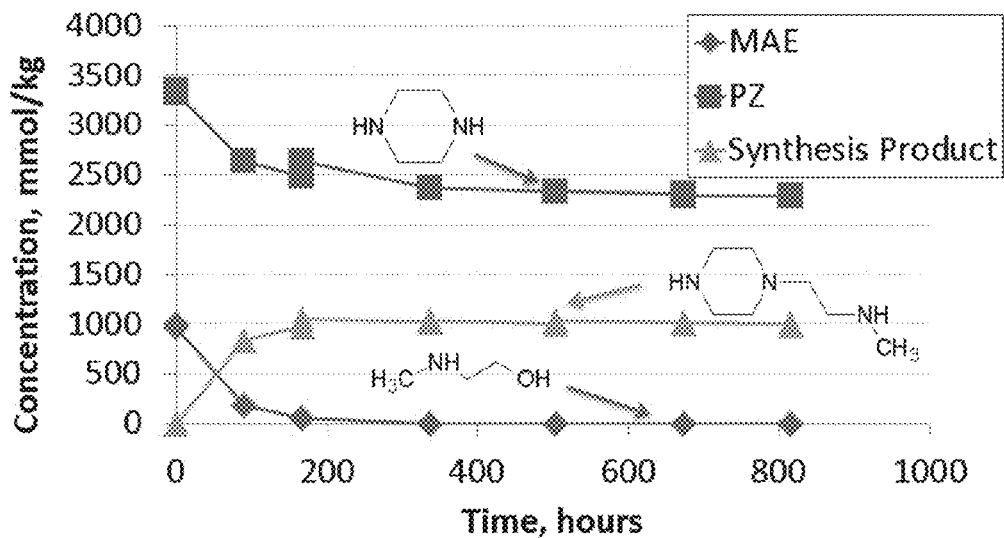

FIG. 46 shows concentration of PZ-MAE Synthesis Product and Parent Amines, demonstrating thermal stability of synthesis product. Initial conditions were 7 m PZ/2 m MAE, 150° C., 0.3 mol $CO_2$/mol N.

Figure 47:
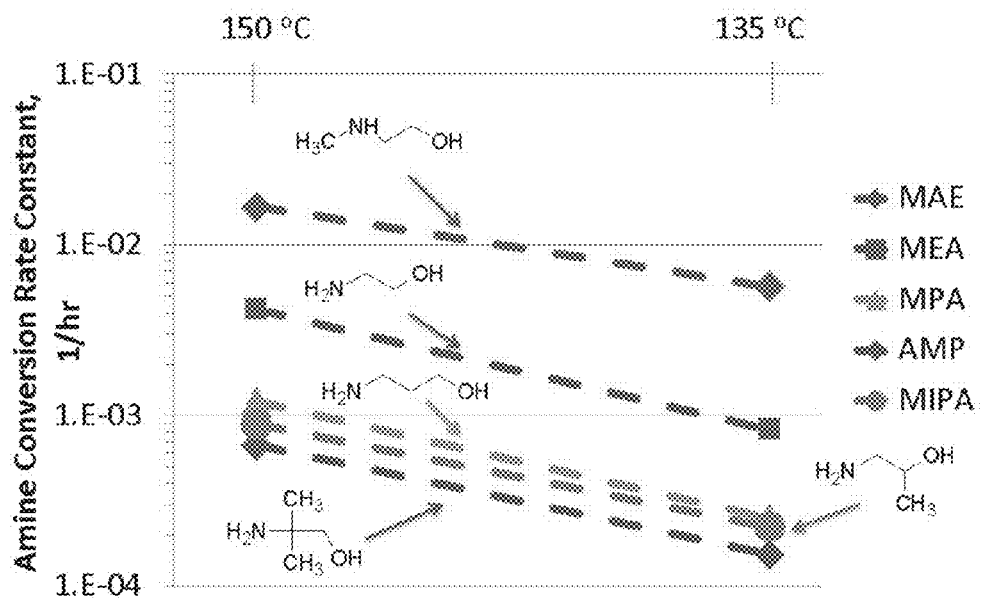

FIG. 47 shows comparison of conversion Rates for Various Amines. Initial conditions were 7 m PZ/2 m amine, 0.3 mol $CO_2$/mol N.

While the present disclosure is susceptible to various modifications and alternative forms, specific example embodiments have been shown in the figures and are described in more detail below. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure generally relates to the removal of acidic gases, including carbon dioxide and hydrogen sulfide, from flue gas or other gases through aqueous absorption and stripping processes. More particularly, in some embodiments, the present disclosure relates to methods and compositions for the removal of acidic gas from a gas mixture using an aqueous amine solvent blend. In some embodiments, the compositions and methods of the present disclosure may be used for the removal of acidic gas from a gas mixture. In one embodiment, the methods of the present disclosure comprise using an aqueous amine solvent comprising a blend of piperazine and at least one diamine or triamine.

In certain embodiments, the present disclosure describes a scrubbing process using a solvent comprising a blend of piperazine and another amine to capture acidic gases such as $CO_2$. Specifically present disclosure describes methods to widen the solubility window of piperazine (PZ) by blending it with another amine, such as hexamethylenediamine (HMDA), putrescine (DAB), 2-(2-aminoethoxy)ethanamine (also known as 3-oxapentane-1,5-diamine or as Bis(aminoethyl)ether, or BAE), or aminoethylpiperazine (AEP). In certain embodiments, the AEP may be produced in situ by thermal degradation with the addition of monoethanolamine to piperazine.

The amine blend has properties broadly similar to piperazine, with high $CO_2$ capacity, high heats of absorption, high $CO_2$ absorption rates, low volatility, and low rates of thermal and oxidative degradation. The wider solubility window may reduce the solid precipitation problems and issues encountered with using only piperazine as the amine solvent. As a result, blending piperazine enables the process to operate at lower temperatures, lower lean loading, and richer rich loading.

The blends described in this disclosure are different from other conventional amine blends in that they avoid the problems of solid precipitation when blending together. The other conventional blends may comprise two dissimilar amines. The blended solvent system described herein may be used over a wider range of $CO_2$ loading than other solvents. For example, it could be used effectively to treat gas with lower or higher $CO_2$ concentration than typically seen in coal flue gas. It could also be used at lower absorber temperatures (for example 20° C.) with greater rich and lean loading. It can be used at lower lean $CO_2$ loading to increase $CO_2$ capacity and reduce the circulation rate of the solvent.

While the amine that is to be blended with the piperazine may be more expensive than piperazine or available in lower quantities, some of these amines degrade at lower temperatures than piperazine and thus could be used in systems that do not have higher pressure steam available to take advantage of greater degradation.

In one embodiment, the present disclosure provides a solvent comprising a blend of piperazine and at least one other amine, such as hexamethylenediamine, putrescine, 2-(2-aminoethoxy)ethanamine, or aminoethylpiperazine.

The piperazine and the other amines may be present in the aqueous amine solvent in any amount. In one embodiment, each of the piperazine and the other amines may be present in an amount sufficient to produce a thermal equilibrium ratio at 100° C. to 160° C. In another embodiment, each of the piperazine and the other amines may be present in amount sufficient to produce a blend with an equilibrium constant ($K_{eq}$) between 0.1 and 0.2. In another embodiment, the piperazine and the other amines may be present in amount sufficient to produce a blend with a $K_{eq}$ between 0.04 and 0.5. In other embodiments, the blend may comprise from about 0.01% to about 99.9% piperazine, from about 0.01% to about 99.9% other amines. In one embodiment, the blend ratio of piperzine:other amine of could be between 50 and 80% piperazine.

The aqueous amine solvent may further comprise water in an amount from about 0.01% to about 99.9% by weight of the blend.

In one embodiment, the present disclosure provides an aqueous amine solvent comprising piperazine and a linear diamine. In certain embodiments, the linear diamine may contain at least 4 carbon atoms between the amine groups present on the linear diamine. In certain embodiments, the linear diamine may contain at least 4 oxygen atoms between the amine groups present on the linear diamine. In certain embodiments, the linear diamine may contain from about 4 to about 6 carbon atoms between the amine groups. In certain embodiments, the linear diamine may contain from about 4 to about 6 oxygen atoms between the amine groups. In certain embodiments, the linear diamine may be 3-oxapentane-1,5-diamine, hexamethylenediamine, 1,4-butanediamine, or 1,5-pentanediamine. In certain embodiments, the linear diamine may be 3-oxapentane-1,5-diamine present in the amine solvent at a concentration in the range of from about 4 to about 12 equivalents/kg water.

The linear diamine may be present in the aqueous amine solvent in an amount sufficient to affect the solubility window of piperazine. In certain embodiments, the linear diamine may comprise 50 mol % or less of the amine in the solvent. In certain embodiments, the linear diamine comprises from about 10 mol % to about 50 mol % of the amine in the solvent. In certain embodiments, the linear diamine may comprise about 10 mol % of the amine in the solvent, in certain embodiments, about 15 mol % of the amine in the solvent, in certain embodiments, about 20 mol % of the amine in the solvent, in certain embodiments, about 25 mol % of the amine in the solvent, in certain embodiments, about 30 mol % of the amine in the solvent, in certain embodiments, about 35 mol % of the amine in the solvent, in certain embodiments, about 40 mol % of the amine in the solvent, in certain embodiments, about 45 mol % of the amine in the solvent, or in certain embodiment, about 50 mol % of the amine in the solvent. In certain embodiments, the linear diamine may be present in the solvent in the range of from about 10 mol % to about 15 mol % of the amine in the solvent, in certain embodiments, from about 15 mol % to about 20 mol %, in certain embodiments, from about 20 mol % to about 25 mol %, in certain embodiments, from about 25 mol % to about 30 mol %, in certain embodiments, from about 30 mol % to about 35 mol %, in certain embodiments, 35 mol % to about 40 mol %, in certain embodiments, 40 mol % to about 45 mol %, in certain embodiments, from about 45 mol % to about 50 mol %.

In certain embodiments, the amine concentration of the aqueous amine solvent may be from about 4 to about 12 equivalents/kg water. In certain embodiments, the amine concentration of the aqueous amine solvent may be from about 8 to about 24 equivalents/kg water. In certain embodiments, the amine concentration may be from about 4 to about 5 equivalents/kg water, in certain embodiments, from about 5 to about 6 equivalents/kg water, in certain embodiments, from about 6 to about 7 equivalents/kg water, in certain embodiments, from about 7 to about 8 equivalents/kg water, in certain embodiments, from about 8 to about 9 equivalents/kg water, in certain embodiments, from about 9 to about 10 equivalents/kg water, in certain embodiments, from about 10 to about 11 equivalents/kg water, in certain embodiments, from about 11 equivalents/kg water to about 12 equivalents/kg water. In certain embodiments, the amine concentration of the aqueous amine solvent may be about 4, about 5, about 6, about 7, about 8, about 9, about 10, about 11, or about 12 equivalents/kg water.

In another embodiment, the present disclosure provides a blend comprising piperazine and aminoethylpiperazine. In certain embodiments, the blend may further comprise diaminoethylpiperazine. In certain embodiments, the blend may comprise 5 m piperazine and 2 m aminoethylpiperazine. In certain embodiments, the amine concentration of the blend may be in the range of from about 8 to about 24 equivalents/kg water. In certain embodiments, the amine concentration of the blend may be about 8 equivalents/kg water, in certain embodiments, about 9, about 10, about 11, about 12, about 13, about 14, about 15, about 16, about 17, about 18, about 19, about 20, about 21, about 22, about 23, or about 24 equivalents/kg water. The blend may be flowed to a stripper. In certain embodiments, the stripper may be operating at a temperature in the range of from about 120° C. to about 165° C. In certain embodiments, the blend composition may reach equilibrium at the operating temperature of the stripper.

In certain embodiments, the aminoethylpiperazine may comprise from about 50 mol % or less of the amine in the blend. In certain embodiments, the aminoethylpiperazine may comprise from about 10 mol % to about 50 mol % of the amine in the blend. In certain embodiments, the aminoethylpiperazine may comprise about 10 mol % of the amine in the blend, in certain embodiments, about 15 mol % of the amine in the blend, in certain embodiments, about 20 mol % of the amine in the blend, in certain embodiments, about 25 mol % of the amine in the blend, in certain embodiments, the about 30 mol % of the amine in the blend, in certain embodiments, about 35 mol % of the amine in the blend, in certain embodiments, about 40 mol % of the amine in the blend, in certain embodiments, about 45 mol % of the amine in the blend, in certain embodiment about 50 mol % of the amine in the blend. In certain embodiments, the aminoethylpiperazine may be present in the range of from about 10 mol % to about 15 mol % of the amine in the blend, in certain embodiments, from about 15 mol % to about 20 mol %, in certain embodiments, from about 20 mol % to about 25 mol %, in certain embodiments, from about 25 mol % to about 30 mol %, in certain embodiments, from about 30 mol % to about 35 mol %, in certain embodiments, 35 mol % to about 40 mol %, in certain embodiments, 40 mol % to about 45 mol %, in certain embodiments, from about 45 mol % to about 50 mol %.

The aqueous amine solvents of the present disclosure may be used for the removal of an acidic gas from a gas mixture. In certain embodiments, the aqueous amine solvents may be flowed to a stripper operating at a temperature in the range of from about 100 to about 200° C., in certain embodiments, from about 120° C. to about 180° C., in certain embodiments, from about 120° C. to about 165° C.

While the present disclosure primarily discusses removal of $CO_2$, any acidic gas capable of removal by the methods of the present invention is contemplated by the present disclosure. Such acidic gases may include, but are not limited to, hydrogen sulfide ($H_2S$) or carbonyl sulfide (COS), $CS_2$, and mercaptans. Similarly, amines may be recovered following absorption of acidic gas. In certain embodiments, such recovery may occur through an evaporation process using a thermal reclaimer.

The gas mixture may be any gas mixture comprising an acid gas for which acid gas removal is desired and which is compatible with (i.e., will not be adversely affected by, or will not adversely react with) the methods of the present disclosure. In certain embodiments, the gas mixture may comprise any gas mixture produced as the byproduct of a chemical process. Suitable gas mixtures may comprise one or more of flue gas, natural gas, hydrogen gas and other gases.

In another embodiment, the present disclosure provides a method for synthesizing aminoethylpiperazine from aqueous monoethanolamine and piperazine in the presence of $CO_2$. By synthesizing aminoethylpiperazine using piperazine and monoethanolamine, the solvent cost may be reduced. In certain embodiments, the synthesis reaction may occur at a temperature in the range of from about 100° C. to about 200° C. In certain embodiments, the synthesis reaction may occur at a temperature in the range of from about 120° C. to about 165° C. The reaction may produce a blend comprising a dimer reaction product, wherein the dimer reaction product may comprise from about 10 mol % to about 50 mol % of the amine in the blend.

In another embodiment, the present disclosure provides a method of forming a substituted piperazine. A substituted piperazine may be formed by reacting piperazine with an alkanolamine at a temperature in the range of from about 100° C. to about 200° C., in certain embodiments, from about 120° C. to about 180° C. In certain embodiments, the reaction may occur within a stripper. The alkanolamine may comprise at least one of a methyl group and an ethyl group. In certain embodiments, the alkanolamine may be a primary or a secondary amine. In certain embodiments, the alkanolamine may be monoethanolamine, methylaminoethanol, monoisopropanolamine, 2-amino-2-methyl-1-propanol, or monopropanolamine.

To facilitate a better understanding of the present invention, the following examples of certain aspects of some embodiments are given. In no way should the following examples be read to limit, or define, the entire scope of the invention.

EXAMPLES

Example 1

Solid Solubility

Experimental Methods:

Amine blends were prepared gravimetrically. Solutions were loaded with $CO_2$ by sparging the gas in the solution and measuring the amount of $CO_2$ added gravimetrically. Samples of both the 6 m PZ/2 m HMDA and 6 m PZ/2 m DAB blends were prepared over a range of $CO_2$ loadings. Solubility (presence of solids) was measured at room temperature in the lab.

Samples of 5 m PZ/2 m AEP, 4 m PZ/2.67 m AEP, and 3 m PZ/3.33 m AEP were prepared over a range of $CO_2$ loadings. The amine solution was placed in a jacketed cylinder; ethylene glycol was used to cool or heat the amine solution to the desired temperature. Transition from solid to liquid was measured over a range of temperatures.

Figure 1:
FIG. 1 is a drawing depicting the structures of various amines.
Figure 1:
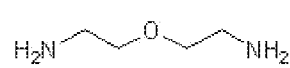
Figure 1:
Figure 1:
Figure 1:
Figure 2:
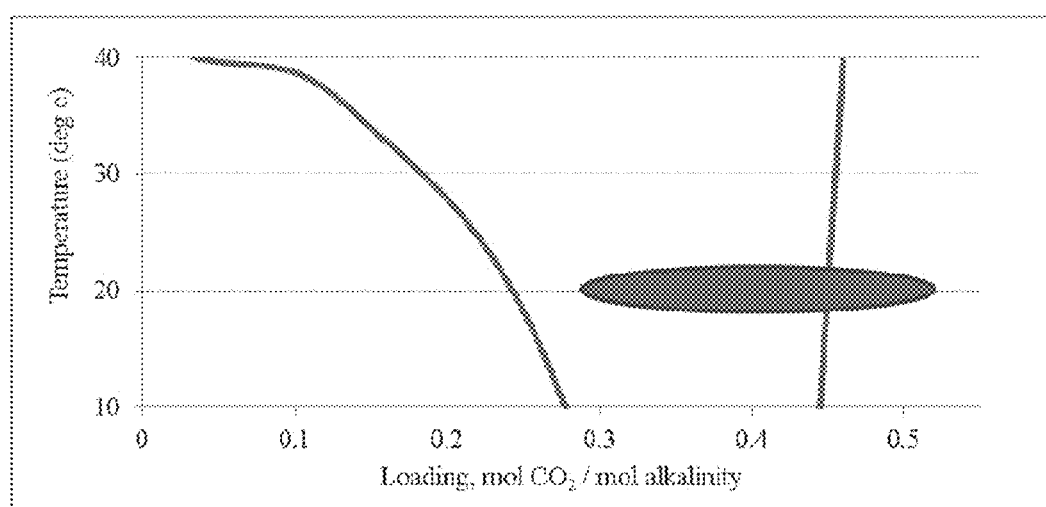
FIG. 2 shows solid solubility limits for 8 m PZ (throughout loading range) denoted by blue lines. For 6 m PZ/2 m HMDA the solubility limit at room temperature (solid-liquid transition) is denoted by the red oval.

FIG. 2 shows the solubility limits for 8 m PZ (blue lines) through a range of $CO_2$ loading and temperature. 8 m PZ is a liquid between the blue lines.

Table 1 gives the observed solid solubility behavior of 6 m PZ/2 m HMDA. 6 m PZ/2 m HMDA is soluble at a loading between 0.3-0.35 mol $CO_2$/mol alkalinity and greater at room temperature (approx. 20° C.); at loading equal to or less than 0.3 and room temperature, solid precipitation does occur. Unlike 8 m PZ there is no upper solubility limit for 6 m PZ/2 m HMDA, and the blend is soluble at loading beyond 0.46 (which is the upper solubility limit for 8 m PZ at room temperature).

TABLE 1

Solid Solubility of 6 m PZ/2 m HMDA at room temperature
Solid Solubility - 6 m PZ/2 m HMDA
Lab room temperature

| Loading mol $CO_2$/mol alk | Solubility Result |
|---|---|
| 0.25 | Solids seen |
| 0.3 | Solids seen |

TABLE 1-continued

Solid Solubility of 6 m PZ/2 m HMDA at room temperature
Solid Solubility - 6 m PZ/2 m HMDA
Lab room temperature

| Loading mol $CO_2$/mol alk | Solubility Result |
|---|---|
| 0.35 | Solids seen after several weeks |
| 0.4 | Soluble |
| 0.5 | Soluble |
| 0.55 | Soluble |

Table 2 gives observations on the solid solubility in 6 m PZ/2 m DAB at room temperature. There appears to be no precipitate at rich loading up to 0.5. At about 0.25 loading there appears to be a phase transition, probably involving solids.

TABLE 2

Solid Solubility of 6 m PZ/2 m DAB at room temperature
Solid Solubility - 6 m PZ/2 m DAB
Lab room temperature

| Loading mol $CO_2$/mol alk | Solubility Result |
|---|---|
| 0.25 | Transition? |
| 0.3 | Soluble |
| 0.35 | Soluble |
| 0.5 | Soluble |

DAB and BAE are diamines whose structures are similar to HMDA but have significantly lower melting points than HMDA. For these blends, the lower solubility limit is wider than 8 m piperazine, and like the 6 m PZ/2 m HMDA blend, do not have an upper solubility limit.

Figure 3:
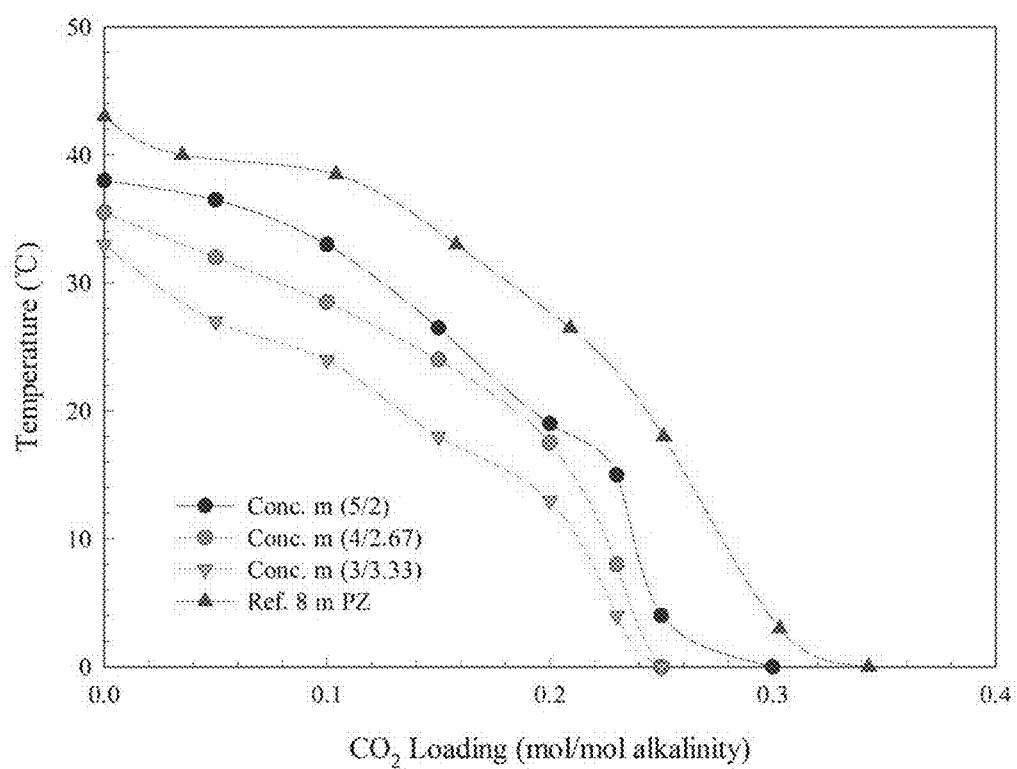
FIG. 3 shows lower solubility limits for various piperazine/aminoethylpiperazine blends.

AEP is a structural analog of PZ. Its solubility window is given in FIG. 3. As with the other diamine blends, blending piperazine with aminoethylpiperazine eliminates the rich solubility window.

Example 2

Rates, Capacity, Thermodynamics

Experimental Methods

The absorption rate and $CO_2$ solubility for each solvent were measured using a wetted wall column (WWC) apparatus.

Materials

The solvent blends were prepared by mixing chemicals gravimetrically. To achieve each $CO_2$ loading condition, $CO_2$ was added to the solvents by bubbling gaseous $CO_2$ (99.99%, Matheson Tri-Gas) into the liquid.

Analytical Methods

The $CO_2$ content in the samples was measured using the total inorganic carbon method. The total alkalinity in the samples was measured using the acid titration method.

Absorption/Desorption Rates

Figure 4:
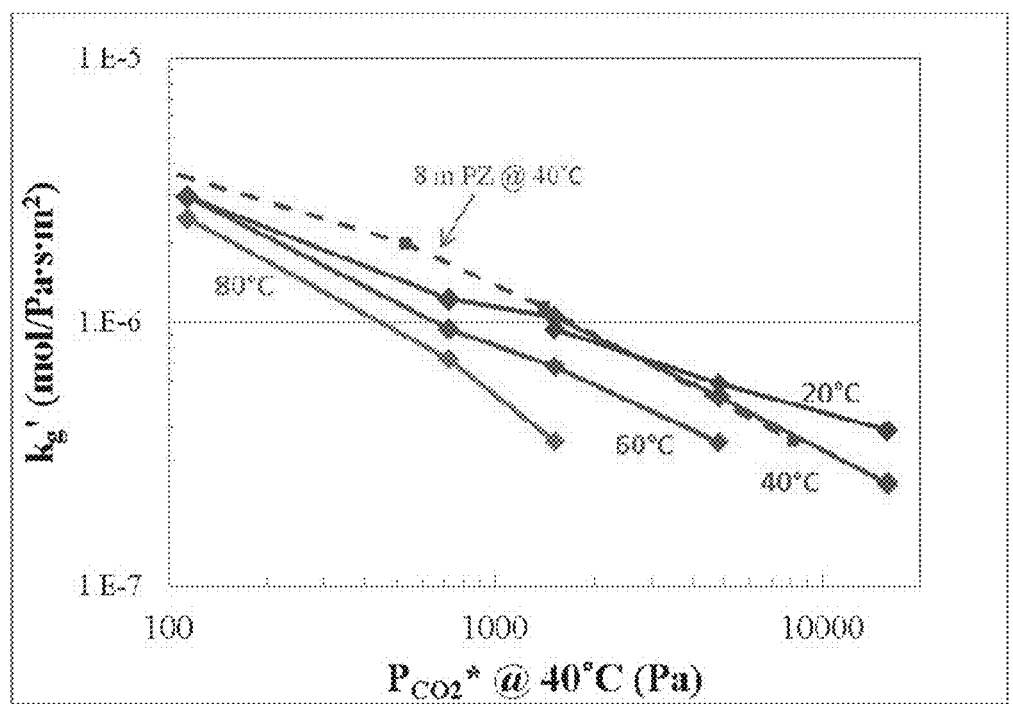
FIG. 4 shows $CO_2$ Liquid Phase Mass Transfer Coefficient ($k_g'$) in 6 m PZ/2 m DAB

The liquid film mass transfer coefficient ($k_g'$) was measured for 6 m PZ/2 m DAB (DAB) at five loadings across the lean and rich loading range (FIG. 4). Four temperatures from 20° C. to 80° C. were tested. Data was not collected at 100° C. for this blend due to the high $CO_2$ partial pressure at high temperature which exceeded the measureable range of the apparatus. Compared at 40 C., the measured $k_g'$ of this blend is slightly lower than 8 m PZ at low loading. At rich loading the absorption rates of the blend is the same as 8 m PZ. The $k_g'$ of this blend has no temperature dependence at low loading and low temperature. Temperature dependence becomes significant as temperature and loading increase. Absorption rate decreases with increase in temperature.

Figure 5:
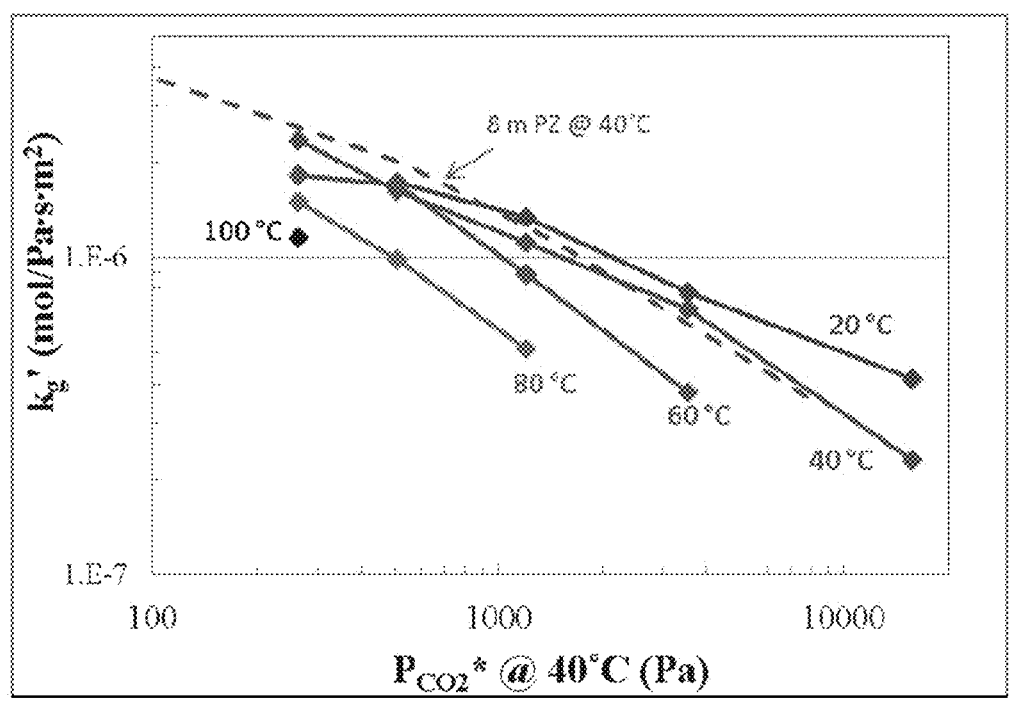
FIG. 5 shows $CO_2$ Liquid Phase Mass Transfer Coefficient (kg') in 6 m PZ/2 m BAE.

It is important to note that 6 m PZ/2 m DAB has unique surface tension property which inhibits formation of smooth and stable liquid film on the WWC. At the typical liquid flowrate of approximately 240 mL/min, a significant portion (10-20%) of the WWC surface area was dry. Therefore, the experiments operated with liquid flowrate 1.5 to 2 times higher than the typical set point. While this adjustment ensured the WWC is wetted in its entirety during the measurements, the liquid film on the WWC exhibits visible ripples at this new condition. The higher liquid flowrate will result in a higher physical mass transfer coefficient ($K_1°$) in the liquid film, which contributes to the values of $k_g'$. The effect of liquid flowrate is more significant at rich loading conditions, where diffusion of species becomes important in the mass transfer in the liquid film. The observed ripples increase the surface area for mass transfer, which results in a higher measured $CO_2$ flux and in turn a higher $k_g'$. Therefore, the reported $k_g'$ values for this blend are potentially higher than their true values (if measured at typical conditions), and this effect is more significant at rich loadings. Also, this observed physical property suggests similar behavior of the solvent in an absorber, where a high liquid flowrate will be necessary for proper wetting of the packing The absorption rates for 6 m PZ/2 m BAE were measured at five $CO_2$ loadings and five temperatures from 20° C. to 100° C. (FIG. 5). The blend has similar $k_g'$ values to 8 m PZ at 40 C. across the $CO_2$ loading range of the experiment. Thus, amine BAE is likely to have similar rate performance to PZ. The absorption rate of the blend decreases with increase in temperature at all loadings except 0.362. In general, the temperature dependence of $k_g'$ for this blend is more significant at rich loadings and at temperatures between 40° C. and 100 C.

Figure 6:
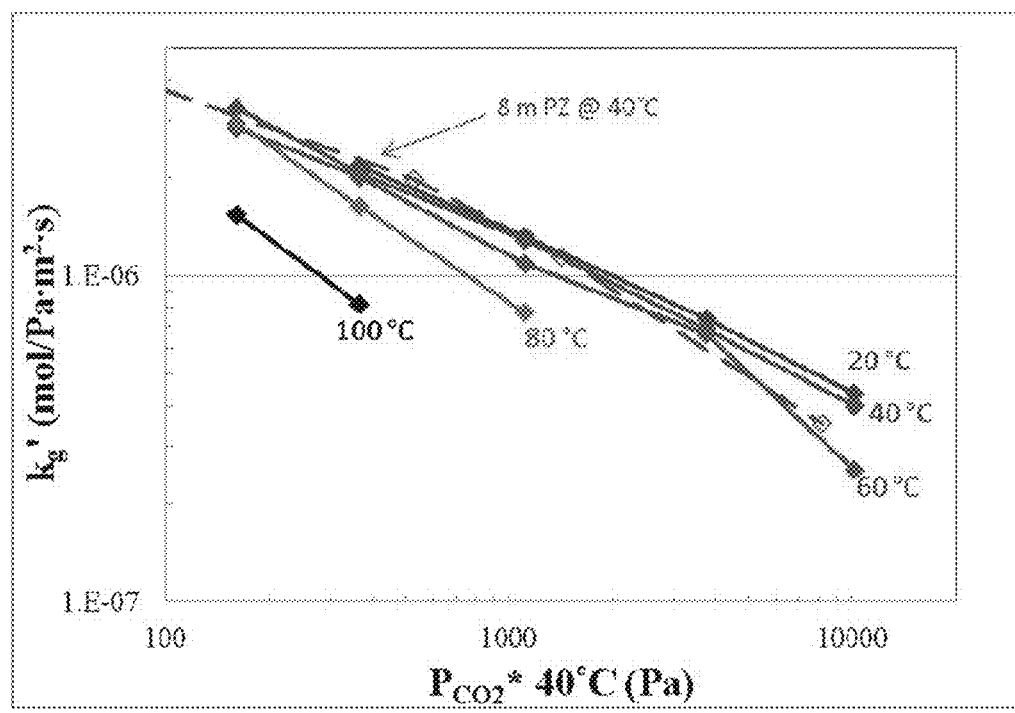
FIG. 6 shows $CO_2$ Liquid Phase Mass Transfer Coefficient ($k_g'$) in 5 m PZ/2 m AEP

For 5 m PZ/2 m AEP, absorption rates were measured at five loadings across the lean and rich operating range (FIG. 6). Five temperatures between 20° C. and 100° C. were measured. At 40° C., the blend has rates similar to 8 m PZ at lean loadings. At rich loadings, the rates of the blend are higher than 8 m PZ. The addition of amine AEP resulted in more highly reactive species in the blend at rich loadings than 8 m PZ. The absorption rate of the blend does not change with temperature between 20° C. and 40° C. at all measured loadings. At 60° C., the measured rate decrease significantly only at the highest loading. Between 80° C. and 100° C., more significant temperature dependence of absorption rate is observed, particularly with an increase in $CO_2$ loading.

To compare the rate performance of the solvents in an absorber, the parameter of $k_{g\,avg}'$ is used to simplify the dynamic behavior in a column into an average rate shown below (Equation 1).

$$k_{g\,avg}' = \frac{(Flux_{CO_2,top} - Flux_{CO_2,bottom})\big/\ln\left(\frac{Flux_{CO_2,top}}{Flux_{CO_2,bottom}}\right)}{\left[(P_{CO_2,top} - P^*_{CO_2,lean}) - (P_{CO_2,bottom} - P^*_{CO_2,rich})\right]\big/\mathrm{Ln}\left[\frac{(P_{CO_2,top} - P^*_{CO_2,lean})}{(P_{CO_2,bottom} - P^*_{CO_2,rich})}\right]} \quad \text{Equation (1)}$$

The approximation in the $k_{g\,avg}'$ assumes an isothermal absorber operating at 40° C. and log mean average between the top and bottom of the absorber column. The approximation is more accurate in the case where the $CO_2$ equilibrium curve is close to linear on a log scale. Nonetheless, the $k_{g\,avg}'$ concept is useful to compare rate performance of solvents on a first order basis. The calculated values of $k_{g\,avg}'$ for the four blends are listed in Table 5.

$CO_2$ Solubility

The equilibrium $CO_2$ partial pressures ($P_{CO2}^*$) for each PZ blend were measured at five $CO_2$ loadings and temperatures from 20° C. to 100° C. A semi-empirical vapor liquid equilibrium model is generated for each solvent by regressing the measured $P_{CO2}^*$ results using Equation 2.

$$\ln(P^*_{CO_2}) = a + \frac{b}{T} + c \cdot ldg + d \cdot \frac{ldg}{T} + e \cdot ldg^2 + f \cdot \frac{ldg^2}{T} \quad (2)$$

The regressed model parameters for each blend are summarized in Table 3.

To calculate cyclic capacity, the solvent lean and rich loadings are first found using the VLE model (Equation 2). The lean and rich loadings corresponds to $P_{CO2}^*$ of 0.5 and 5 kPa at 40 C., respectively. These values are then used in Equation 3 to give the capacity of the solvent. A large difference between the rich and lean loading values will result in a high cyclic capacity.

$$\text{Capacity} = (\text{rich } ldg - \text{lean } ldg) \cdot \frac{\text{mol Alkalinity}}{\text{kg solvent}} \quad (3)$$

The semi-empirical VLE model (Equation 2) can also predict solvent heat of absorption. Theoretically, the heat of absorption of $CO_2$ is defined as the temperature dependence of the thermodynamic equilibrium of $CO_2$ in the solvent. This thermodynamic relationship is expressed is Equation 4.

$$H_{abs} = -R \cdot \frac{\partial(\ln P^*_{CO_2})}{\partial\left(\frac{1}{T}\right)} = -R \cdot (b + d \cdot ldg + f \cdot ldg^2) \quad (4)$$

The calculated cyclic capacity and heat of absorption at the midpoint of the loading range ($P_{CO2}^*=1.5$ kPa) for each solvent are summarized in Table 4.

Figure 7:
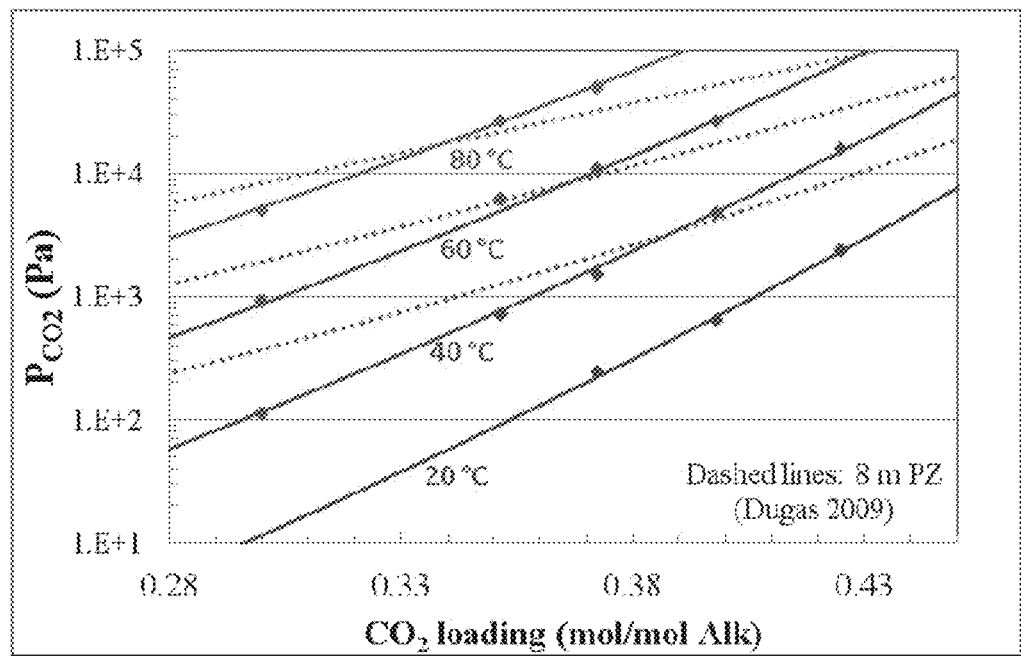
FIG. 7 shows $CO_2$ solubility of 6 m PZ/2 m DAB.

The measured $P_{CO2}^*$ and the regressed semi-empirical VLE model for 6 m PZ/2 m DAB are plotted in FIG. 7 and compared against 8 m PZ (dashed lines). $CO_2$ is more soluble in the blend than 8 m PZ at low loadings, but less soluble at rich loadings. The high $CO_2$ solubility at low loadings could be attributed to the free amine DAB in the blend, which has a high pKa value. As loading increases, free amine DAB is consumed by protonation and formation of carbamate. At rich loadings, the second amine group on the carbamate of amine DAB and protonated amine DAB is likely the dominating $CO_2$ absorbing species. The low $CO_2$ solubility at rich loading suggests low $CO_2$ capacity of the second amine group on amine DAB, which could be the result of low pKa value. The addition of amine DAB results in a large change of $P_{CO2}^*$ with increased $CO_2$ loading, and thus a lower solvent capacity. However, with two carbamate-forming amine groups, amine DAB contributes to the heat of absorption of the solvent which results in a high heat of absorption for the blend.

Figure 8:
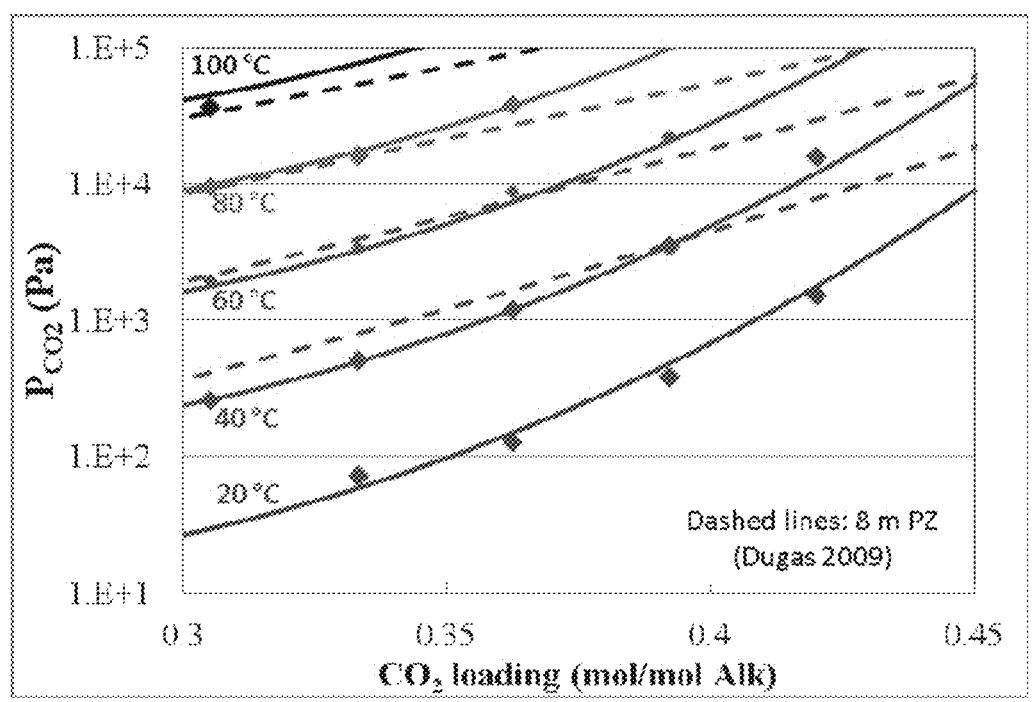
FIG. 8 shows $CO_2$ solubility of 6 m PZ/2 m BAE.

The $CO_2$ solubility results for 6 m PZ/2 m BAE (FIG. 8) exhibit similar trends to PZ/DAB but to a lesser extent. The first amine group of amine BAE has a lower pKa value than amine DAB, while the pKa of the second amine group is likely higher than that of amine DAB. Therefore, the $CO_2$ solubility curve of PZ/BAE is more similar to 8 m PZ than the PZ/DAB blend. Since the slope of the $CO_2$ solubility curve is lower for PZ/BAE than for PZ/DAB, PZ/BAE has higher cyclic capacity. Both of the amine groups in amine BAE react with $CO_2$ to form carbamates, which results in a high heat of absorption of the blend similar to PZ/DAB.

Figure 9:
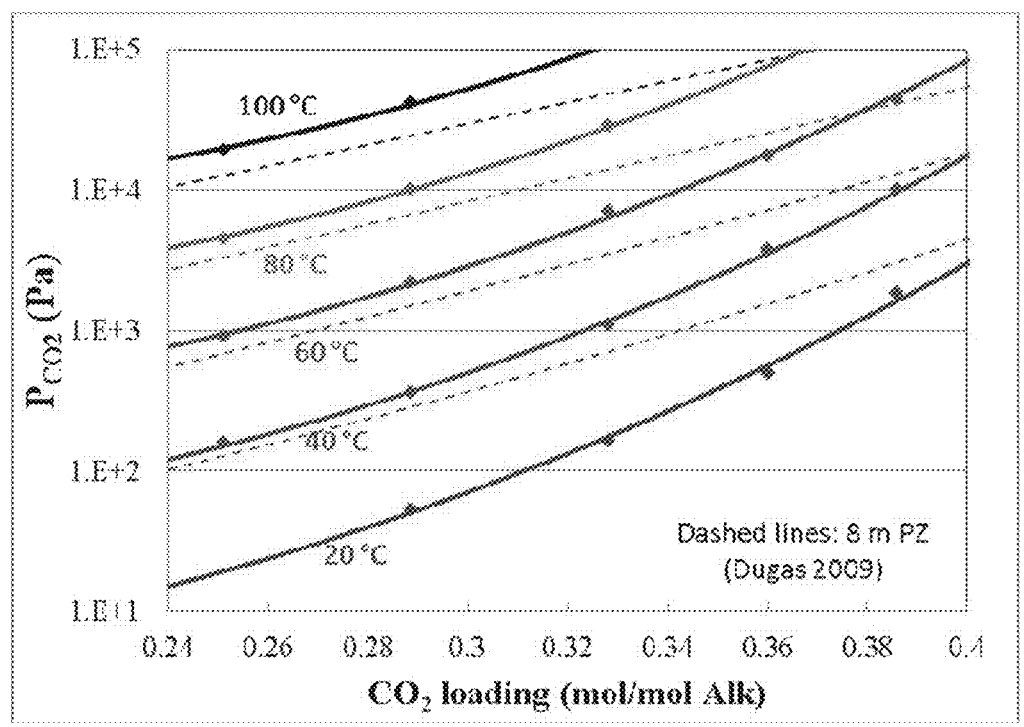
FIG. 9 shows $CO_2$ solubility of 5 m PZ/2 m AEP

The $P_{CO_2}*$ for 5 m PZ/2 m AEP is higher than 8 m PZ across the operating loading range and all temperatures (FIG. 9). The low $CO_2$ solubility of the blend is because $CO_2$ is less soluble in amine AEP than in PZ. At low loadings, the measured $P_{CO_2}*$ for the blend is similar to 8 m PZ since a significant amount of PZ is available for $CO_2$ absorption. As loading increases, PZ is consumed by absorbed $CO_2$, and amine AEP and derivatives become the active species in the blend, which results in much lower $CO_2$ solubility of the blend at high loadings. The large increase in $P_{CO_2}*$ at high loadings results in a steep slope for the $CO_2$ solubility curve, which contributes to a lower capacity for this blend than 8 m PZ.

TABLE 3

Regressed semi-empirical VLE model parameters for PZ blends

| Amines | Concentration (m) | a Intercept | b 1/T | c Loading | d ldg/T | e ldg$^2$ | f ldg$^2$/T |
|---|---|---|---|---|---|---|---|
| PZ/DAB | 6/2 | 45.7 | −15287.6 | −33.2 | 15702.5 | 30.4 | / |
| PZ/BAE | 6/2 | 37.5 | / | −8410.2 | −16668.0 | / | 37391.1 |
| PZ/AEP | 5/2 | 42.0 | −11781.6 | −45.3 | 9154.8 | 73.7 | / |

Properties of the new PZ blends are compared against 8 m PZ, 7 m MEA, and 6 m PZ/2 m HMDA. All four PZ blends have competitive absorption rates compared to 8 m PZ, with 5 m PZ/2 m AEP having the highest and 6 m PZ/2 m DAB the lowest rate. The cyclic capacities of the four blends are lower than 8 m PZ by 15-20%. 5 m PZ/2 m AEP, has a higher capacity at 0.66 mol/kg, which is 10% higher than 7 m MEA. The heats of absorption of 6 m PZ/2 m DAB, and 6 m PZ/2 m BAE are higher than both 8 m PZ and 7 m MEA by about 10-12%. 5 m PZ/2 m AEP has a heat of absorption slightly higher than 7 m MEA, which is about 5% higher than 8 m PZ. Compared to 6 m PZ/2 m HMDA, the two new amine blends have higher absorption rates (60%), slightly higher capacities, and higher heats of absorption (18%).

TABLE 4

Measured performance properties of PZ blends

| Amines | Concentration (m) | $k'_{g\,avg}$ ×10$^7$ (mol/ s·Pa·m$^2$) | Capacity mol/kg | −$H_{abs}$ kJ/mol |
|---|---|---|---|---|
| PZ/DAB | 6/2 | 7.68 | 0.55 | 79 |
| PZ/BAE | 6/2 | 8.03 | 0.62 | 79 |
| PZ/AEP | 5/2 | 8.92 | 0.66 | 72 |
| PZ/HMDA | 6/2 | 4.90 | 0.53 | 67 |
| PZ (Dugas, 2009) | 8 | 8.46 | 0.79 | 64 |
| MEA (Dugas, 2009) | 7 | 4.30 | 0.47 | 70 |

The various piperazine blends all have capacities somewhat less than that of piperazine (70-85%) but have generally similar absorption rates and higher (by 5-20%) heats of absorption.

Example 3

Thermal Degradation

Experimental

Solvent Preparation

Amine blends were prepared gravimetrically. Solutions were loaded with $CO_2$ by sparging the gas in the solution and measuring the amount of $CO_2$ added gravimetrically.

Thermal Degradation Experiments

Samples were kept in 10 ml stainless steel cylinders and placed in convection ovens operating at 175° C. for several weeks and were removed periodically. 10 ml of loaded amine solution was placed in each cylinder for the 6 m PZ/2 m amine DAB and 8 m amine DAB thermal degradation experiments. For the 6 m PZ/2 m amine BAE degradation experiment, only 7 ml of amine solution was placed in the cylinder, giving an extra 3 ml of headspace and reducing the chance of cylinder failure due to overpressure.

Samples were analyzed using cation chromatography (Dionex ICS2100) and anion chromatography (Dionex ICS3000) to determine amine loss over time. Samples were diluted to 10000× prior to analysis in the cation chromatography column and 100× prior to analysis in the anion chromatography column.

Results and Discussion—Thermal Degradation of piperazine Blends

Thermal Degradation—Model Development

First-order rate models were used to analyze degradation rates. This model can reasonably represent degradation rates and is helpful for comparing degradation rates of different amine solvents as well as individual amines in a blend. The first rate order equation is given as follows:

$$-\frac{dC_A}{dt} = -r_A = kC_A \quad (5)$$

This expression can then be integrated:

$$C_A = C_{A0}\exp(-kt) \quad (6)$$

Figure 10:
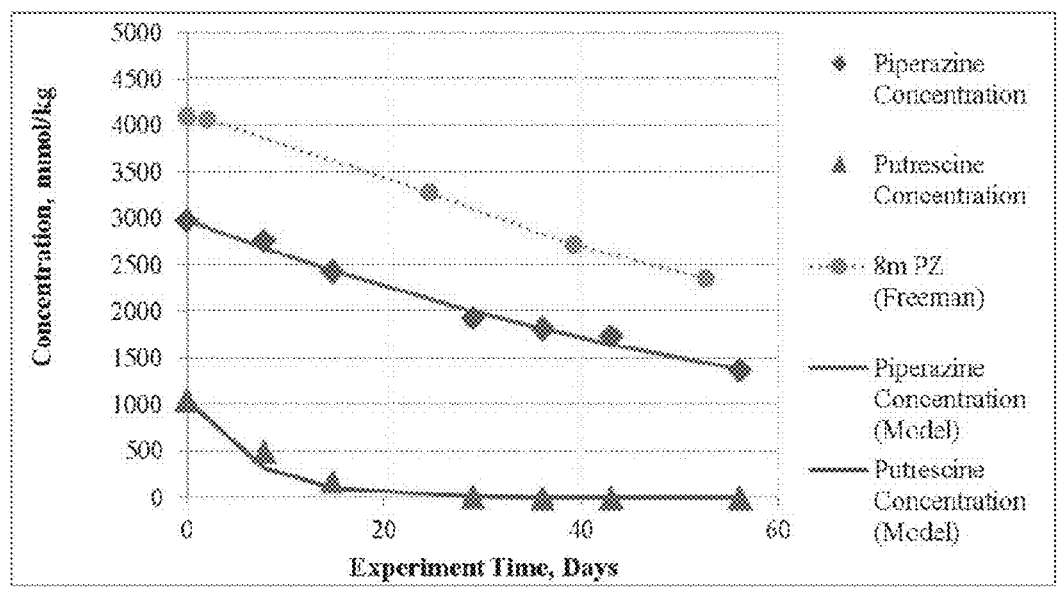
FIG. 10 shows concentration versus time plot of 6 m PZ/2 m amine DAB, T=175 C., initial loading=0.4 mol $CO_2$/mol alkalinity.

Thermal Degradation—6 m PZ/2 m Amine DAB 6 m PZ/2 m amine DAB at a loading of 0.4 mol $CO_2$/mol alkalinity was degraded over approximately two months. Concentrations of the amines as functions of time are plotted in FIG. 10.

Although amine DAB is almost completely degraded after about three weeks, the rate of degradation of PZ in the blend is relatively unaffected and is comparable to the degradation rate of 8 m PZ at a loading of 0.3. This seems to suggest that there is no synergistic effect between the two amines from a degradation standpoint; they degrade independently of one another.

The model degradation rate constant estimates are $1.60*10^{-7}$ seconds$^{-1}$ for PZ and $1.78*10^{-6}$ seconds$^{-1}$ for amine DAB.

Figure 11:
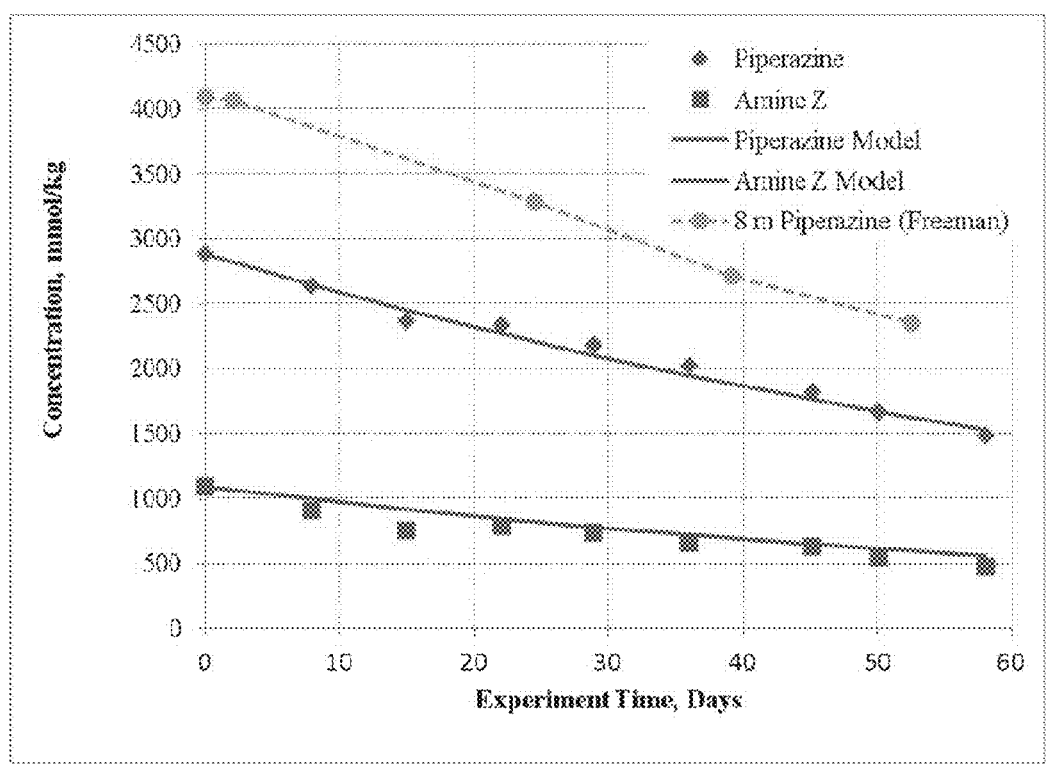
FIG. 11 shows concentration versus time plot of 6 m PZ/2 m Amine BAE, T=175 C., initial loading=0.35 mol $CO_2$/mol alkalinity.

Thermal Degradation—6 m piperazine/2 m Amine BAE 6 m PZ/2 m amine BAE at an initial loading of 0.35 mol $CO_2$/mol alkalinity was degraded at 175° C. over 58 days. Amine concentration over time is plotted in FIG. 11.

Figure 12:
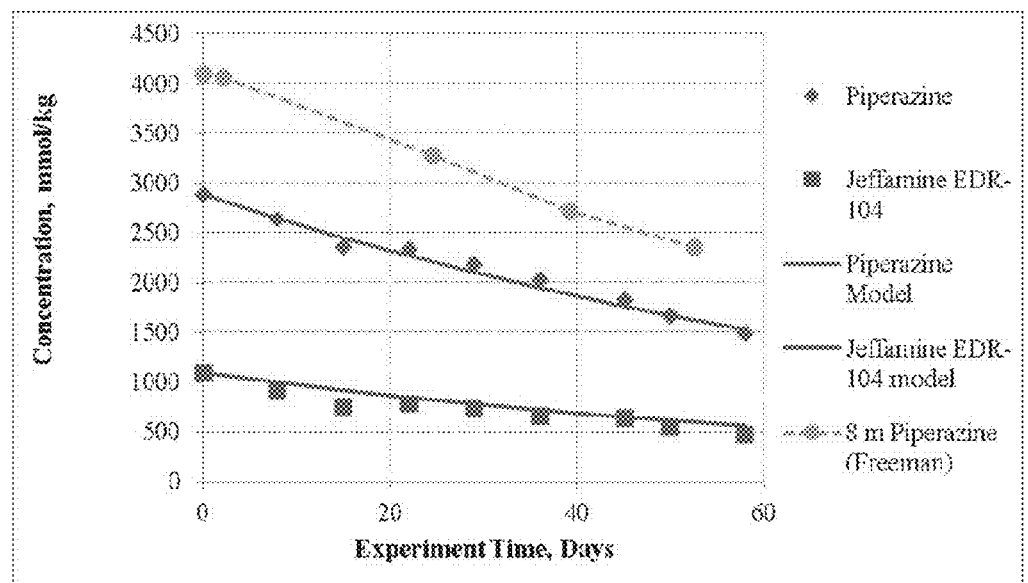
FIG. 12 shows concentration versus time plot of 6 m PZ/2 m amine DAB, T=175 C., loading=0.4 mol $CO_2$/mol alkalinity.

As with 6 m PZ/2 m amine DAB, the 6 m PZ/2 m amine BAE blend shows little blend synergism from a degradation standpoint. The degradation rate of the PZ in the blend is identical to straight-run 8 m PZ. The degradation rate of amine BAE is nearly identical to PZ, as shown in FIG. 12.

The model rate constant estimates are $1.29*10^{-7}$ seconds$^{-1}$ for PZ and $1.33*10^{-7}$ seconds$^{-1}$ for amine BAE.

Figure 13:
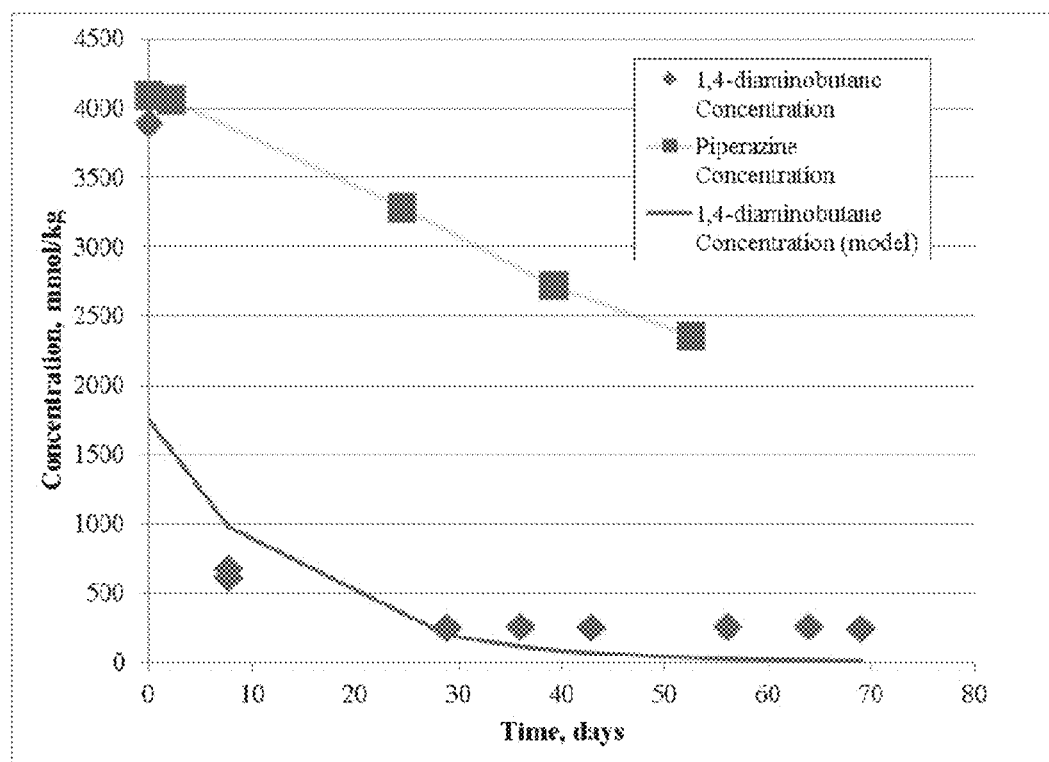
FIG. 13 shows degradation of 8 m 1,4-diaminobutane at 175° C. The degradation of 8 m PZ is from Freeman (Freeman, 2011) and at a loading of 0.3 mol $CO_2$/mol alkalinity.

Thermal Degradation—8 m 1,4-diaminobutane 8 m 1,4-diaminobutane was degraded at 175° C. over 69 days. Concentration of the amine as a function of time is plotted in FIG. 13. The degradation rate was approximated using first order kinetics.

Unlike PZ, the degradation of DAB is fairly rapid; using first order kinetics, it has a degradation rate constant of $750*10^{-9}$ 1/sec, compared to $130*10^{-9}$ 1/sec for PZ. Only the data for the first two weeks are considered for the degradation analysis as the concentration of DAB appears to reach a constant value after two weeks at 175° C. This behavior was not seen when 1,4-diaminobutane was blended with PZ; all of the DAB degraded after two weeks when blended with piperazine.

Figure 14:
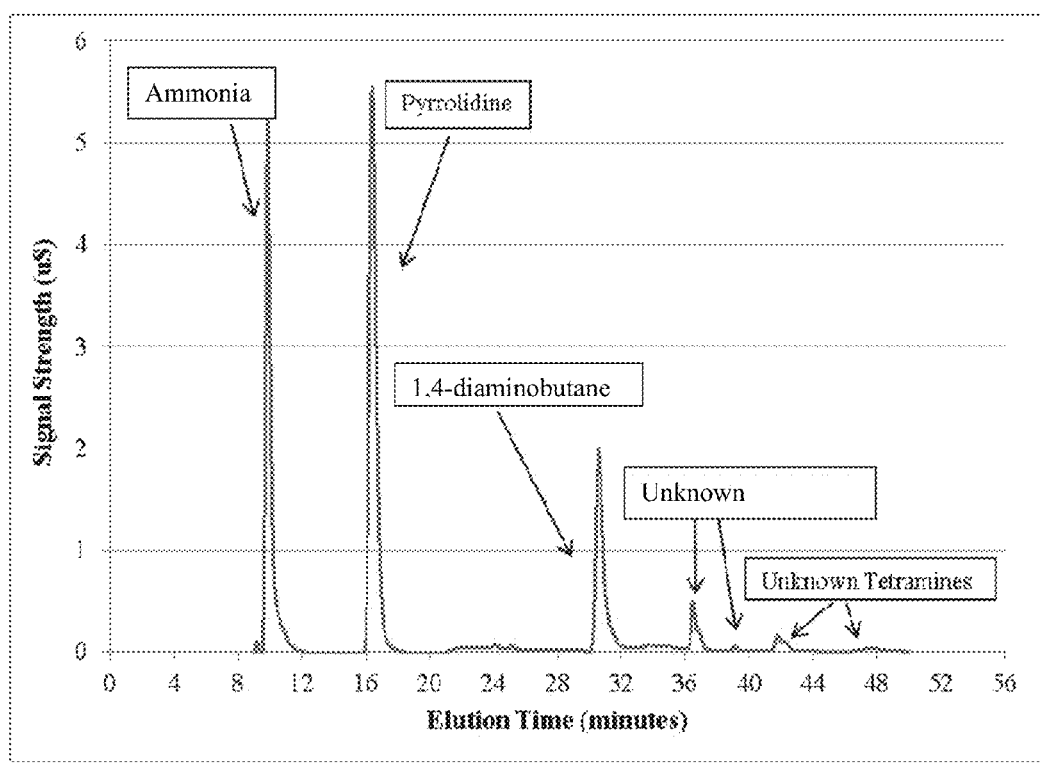
FIG. 14 is a chromatogram showing degradation products of 1,4-diaminobutane after one week. Temperature was held at 175° C. with initial loading equal to 0.4 mol $CO_2$/mol alkalinity.

The chromatogram of a sample after 1 week at 175° C. is presented in FIG. 14.

Figure 15:
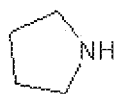
FIG. 15 is a drawing depicting the structure of pyrrolidine.

The primary degradation products appear to be pyrrolidine and ammonia. Minor degradation products include unknown triamines and tetramines; these are probably degradation products between DAB and itself, pyrrolidine and itself, or DAB and pyrrolidine. FIG. 15 is a drawing of the structure of pyrrolidine.

Figure 16:
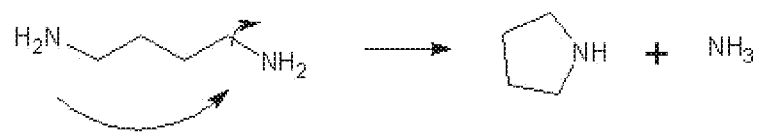
FIG. 16 is a drawing depicting a proposed degradation pathway of 1,4-diaminobutane to pyrrolidine and ammonia.

A proposed degradation pathway is given in FIG. 16, in which the nitrogen on one end of the molecule attacks the alpha carbon of the amino group on the other end of the molecule, creating a cyclic amine and forming ammonia in the process.

Figure 17:
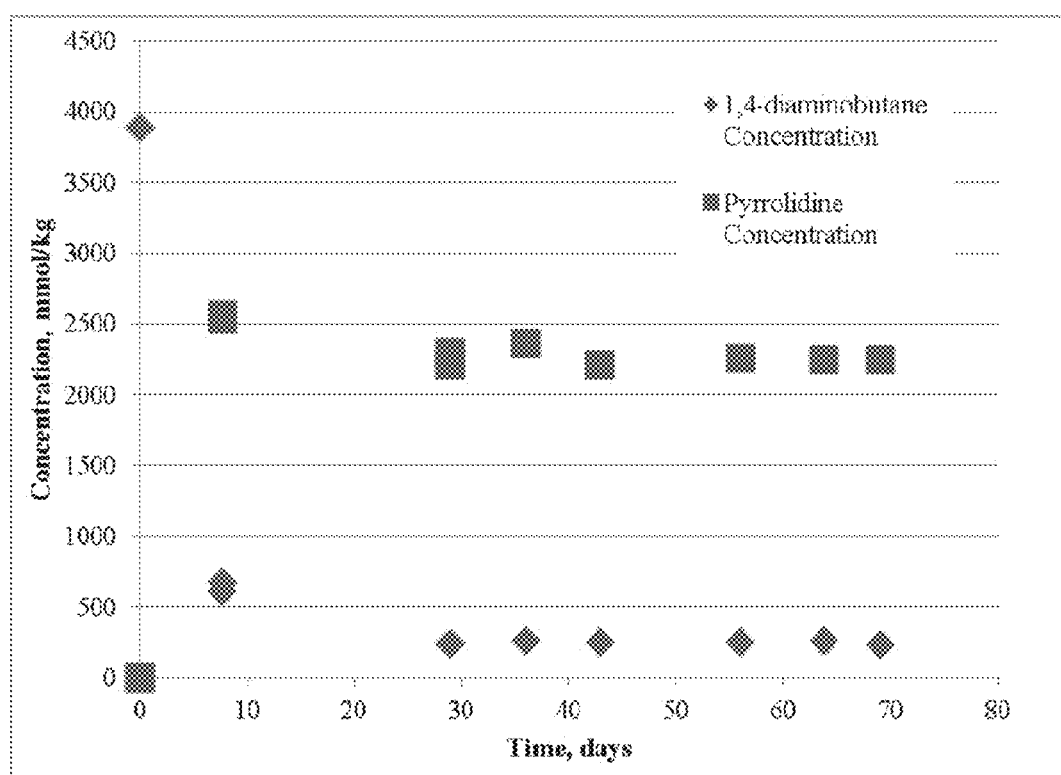
FIG. 17 is a plot of the concentration of pyrrolidine over time and concentration of 1,4-diaminobutane over time at 175° C.

FIG. 17 shows a plot of the concentration of pyrrolidine over time and concentration of 1,4-diaminobutane over time. It appears that after about two weeks the concentrations of 1,4-diaminobutane and pyrrolidine stabilize and approach an equilibrium.

Figure 18:
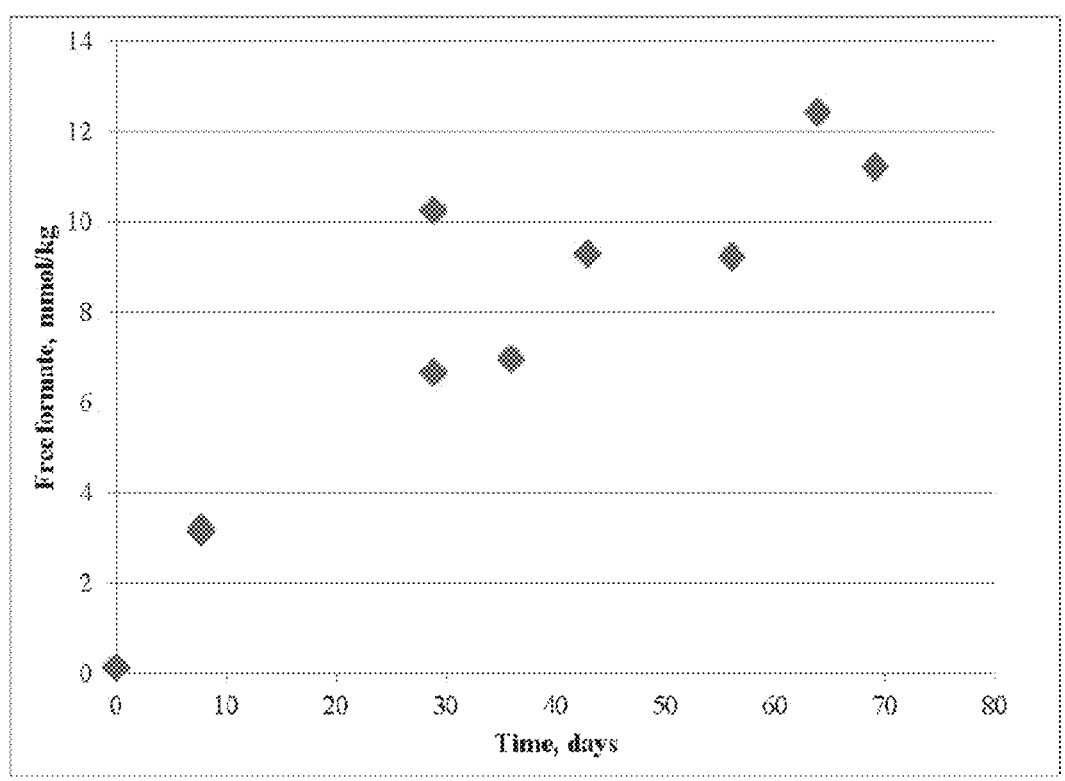
FIG. 18 is a chart depicting the formation of free formate in 8 m DAB at 175° C.

FIG. 18 shows the concentration of free formate over time. Other salts (oxalates, nitrates) were present but below the detection range of the instrument. The samples were not hydrolyzed with sodium hydroxide prior to analysis. There is scatter in the data, but the free formate seems to increase steadily with time. At a maximum value of 12 mmol/kg solution, it does not represent a significant fraction of the degraded DAB, 3500 mmol/kg.

Figure 19:
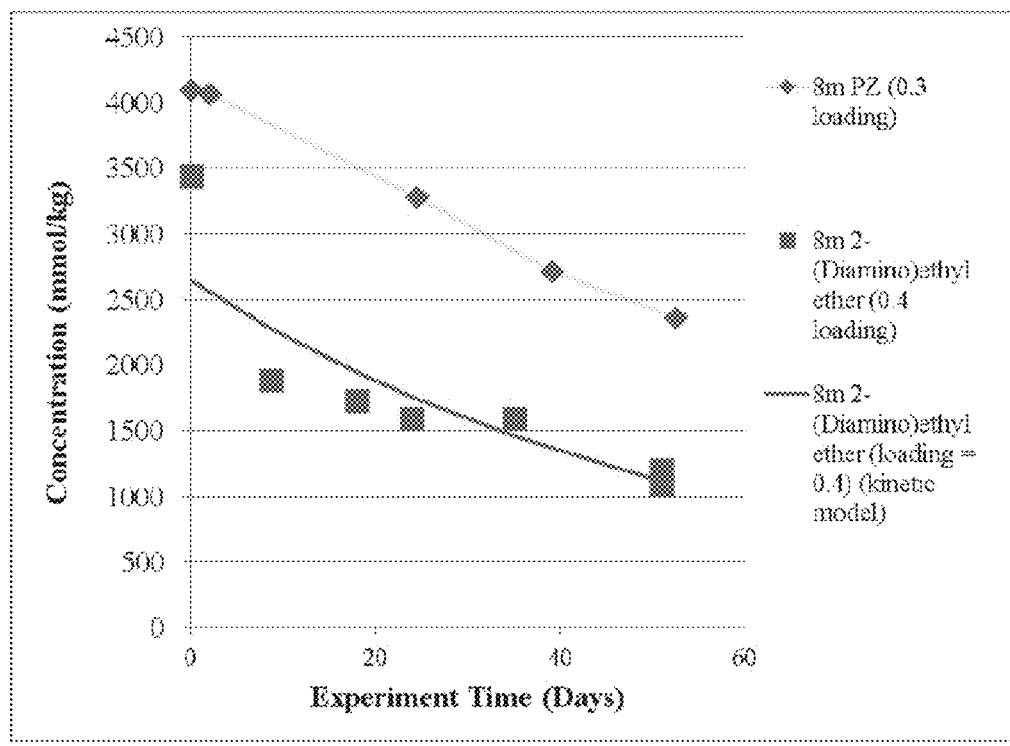
FIG. 19 is a chart depicting degradation of 8 m 3-oxapentane-1,5-diamine at 175° C. The degradation of 8 m PZ is from Freeman (Freeman, 2011).

Thermal Degradation—8 m 3-oxapentane-1,5-diamine 8 m BAE was degraded at 175° C. over 51 days. The concentration of the amine as a function of time is plotted in FIG. 19.

Like PZ, BAE is resistant to thermal degradation with a first order degradation rate constant of about $200*10^{-9}$ 1/sec. For comparison, the first order degradation rate constant of 8 m PZ is about $130*10^{-9}$ 1/sec. The first order degradation rates of PZ and BAE when in a 6 m PZ/2 m BAE blend were about $130*10^{-9}$ 1/sec and $130*10^{-9}$ 1/sec respectively, which suggests that blend synergism is not taking place.

Figure 20:
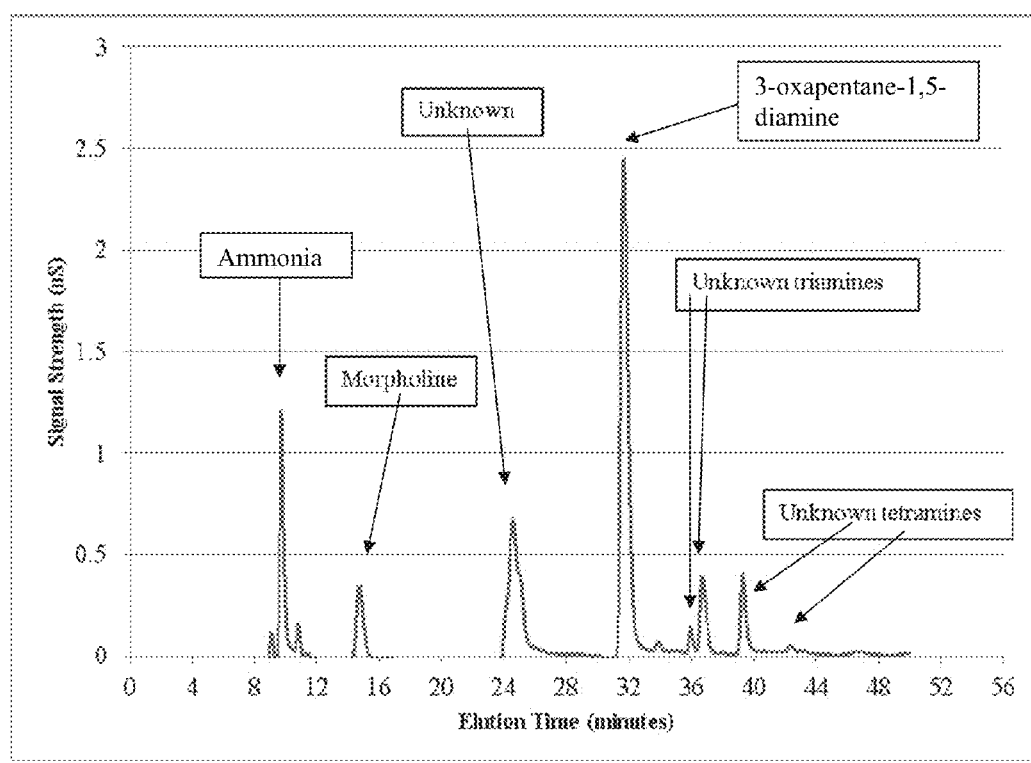
FIG. 20 is a chromatogram showing degradation products of 3-oxapentane-1,5-diamine after one week. Temperature was held at 175° C. with initial loading equal to 0.4 mol $CO_2$/mol alkalinity.

Key degradation products likely consist of morpholine, ammonia, an unknown triamine, and an unknown tetramine. Like 1,4-diaminobutane, these degradation products might be between BAE and itself, BAE and morpholine, or morpholine and itself. The elution times of these products are presented in the chromatogram in FIG. 20.

Figure 21:
FIG. 21 is a drawing depicting the structure of morpholine.
Figure 22:
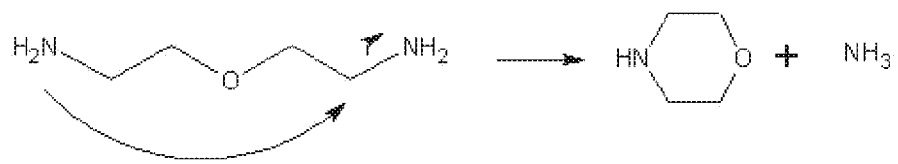
FIG. 22 is a drawing depicting a proposed degradation pathway of 3-oxapentane-1,5-diamine to morpholine and ammonia.

Morpholine might be formed from the ring closing of BAE in a manner similar to how 1,4-diaminobutane ring closes to form pyrrolidine. FIG. 21 shows the structure of morpholine. FIG. 22 shows a pathway for forming morpholine.

Table 5 shows the first order rate constants for the thermal degradation rates of the various piperazine blends at a temperature of 175 degrees C. It is important to note that the presence of the other amine does not significantly increase the degradation rate of the piperazine.

TABLE 5

Degradation of Amines in Piperazine Blends at T = 175° C.

| Amines | Loading (mol $CO_2$/mol alkalinity) | $k_{Overall}$ $\times 10^7$ (1/s) | $k_{Piperazine}$ $\times 10^7$ (1/s) | $k_{otheramine}$ $\times 10^7$ (1/s) |
|---|---|---|---|---|
| 6 m PZ/2 m DAB | 0.4 | 1.28 | 1.26 | 1.33 |
| 6 m PZ/2 m BAE | 0.35 | 2.42 | 1.59 | 16.5 |
| 6 m PZ/2 m HMDA | 0.4 | 1.09 | — | — |
| 8 m PZ (Ref 1) | 0.3 | 1.26 | — | — |

Viscosity Measurements:

Viscosity was measured using a cone and plate rheometer (Anton Parr Physica MCR301).

Viscosity measurements of 5 m PZ/2 m AEP with $CO_2$ loading of 0.2 and 0.3 mol/mol alkalinity were conducted at 20° C., 40° C. and 60° C. (presented in Table 6). The primary result suggests that the viscosity of the blend is comparable to that of pure 8 m PZ (i.e., 11.96 cP for 5 PZ/2 AEP vs. 9.99 cP for 8 m PZ at 0.3 loading and 40° C.). The data also demonstrate the expected trend that viscosity increases with increasing $CO_2$ concentration and decreasing temperature.

TABLE 6

Viscosity of 5 m PZ/2 m AEP from 20 to 60° C.

| $CO_2$ Loading (mol/mol alk) | Viscosity (cP) | | |
|---|---|---|---|
| | 20° C. | 40° C. | 60° C. |
| 0.20 | 21.92 ± 0.068 | 9.843 ± 0.082 | 5.88 ± 0.162 |
| 0.30 | 24.75 ± 0.090 | 11.96 ± 0.108 | 7.78 ± 0.720 |

Example 4

Synthesis of Aminoethylpiperazine

AEP is readily synthesized from aqueous monoethanolamine and piperazine in the presence of $CO_2$.

In the presence of $CO_2$ MEA reacts reversibly to form the oxazolidinone:

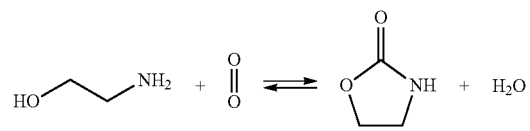

In the absence of other primary or secondary amines the oxazolidinone will react with MEA to produce hydroxyethylethylenediamine:

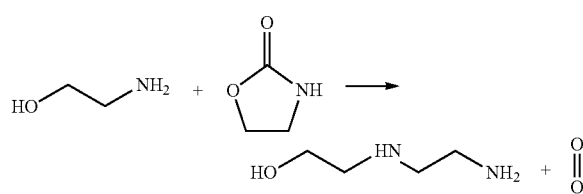

In a blend of MEA and PZ, it has been shown that PZ reacts with the oxazoldinone to degrade the MEA and PZ to AEP:

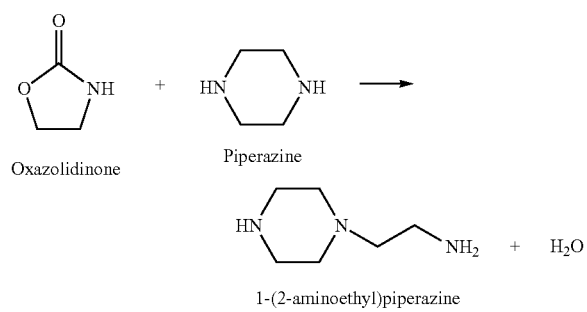

Figure 23:
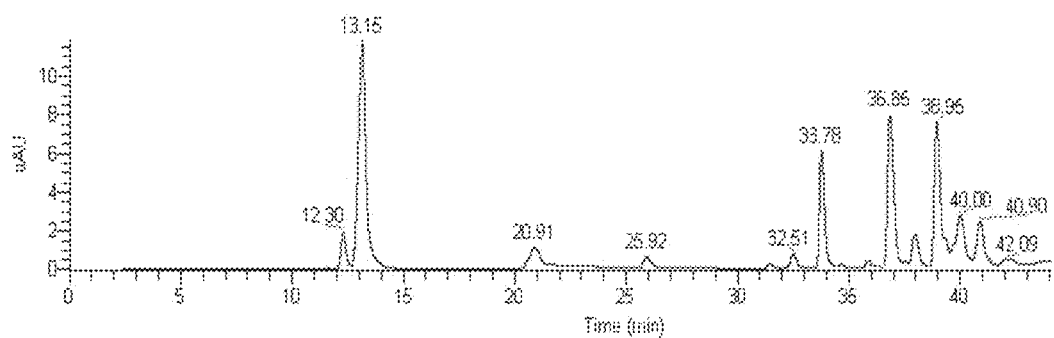
FIG. 23 is a IC/MS chromatogram of a 7 m MEA/2 m piperazine aqueous solution with a loading of 0.4 moles of $CO_2$ per mole of alkalinity held at 135° C. for 8 weeks (Davis, 2009).
Figure 24:
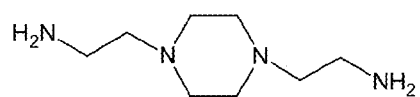
FIG. 24 is a drawing depicting the structures of products formed from 1-(2-aminoethyl)piperazine with oxazolidone
Figure 25:
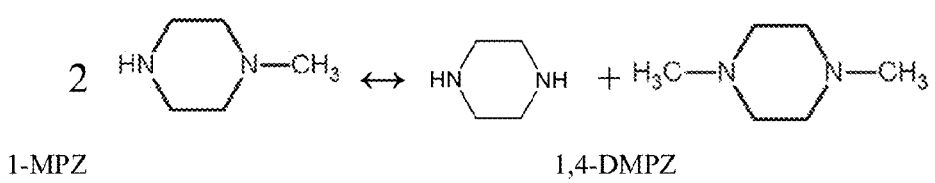
FIG. 25 is a drawing depicting the structure of methyl-substituted PZs.

FIG. 23 shows a IC/MS chromatogram of a 7 m MEA/2 m piperazine aqueous solution with a loading of 0.4 moles of $CO_2$ per mole of alkalinity held at 135° C. for 8 weeks.

The peak at 13.1 min is MEA and the peak at 33.8 min is PZ. The next largest peak at 36.9 minutes is the primary product that we want to make, 1-(2-aminoethyl)piperazine, with a mass of 129. The next largest product peak is at 39.0 min with a molecular weight of 172 corresponds to 1,4-piperazinediethanamine (DAEP) which would be made that the reaction of AEP with oxazolidinone.

In the absence of MEA DAEP will also be produced by an arm switching mechanism common with tertiary amines at elevated temperatures. It has been shown that the 1-methylpiperazine (1MPZ) would react to form an equilibrium mixture of 1-MPZ, PZ and 1,4-dimethylpiperazine (DMPZ)

By a similar mechanism, AEP will disproportionate at elevated temperature to make an equilibrium mixture of AEP, PZ, and DAEP:

The peak at 32.5 minutes is HEEDA, the dimer of MEA found in MEA only systems, and the peak at 20.7 minutes corresponds to triHEIA also from the MEA only system. HPLC also showed the appearance of HEIA which is the largest degradation product found in the MEA only system. A mixture of degradation products has been detected from the interaction of MEA and PZ as well as from the reactions seen in a MEA only system.

Figure 26:
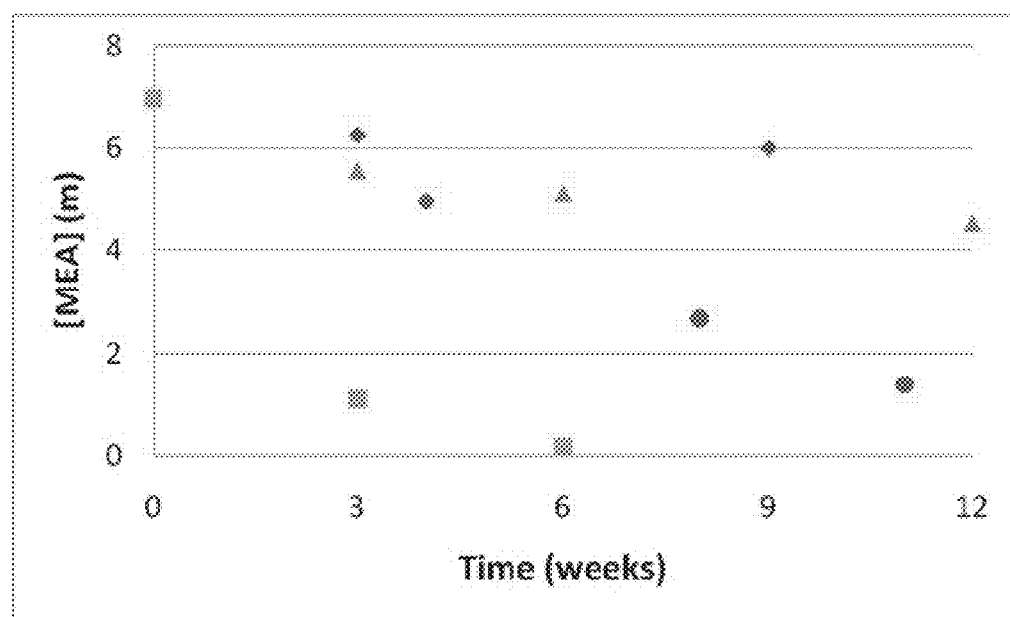
FIG. 26 shows MEA concentration over time in a 7 m MEA/2 m PZ aqueous solution with a loading of 0.4 moles $CO_2$/mole of alkalinity at varying temperatures. diamond=100° C., triangle=120° C., circle=135° C., and square=150° C.

FIG. 26 shows the concentration of MEA over time at a variety of temperatures.

The amount of MEA loss behaves very similarly to an MEA only system with small losses at 100 and 120° C. and substantial losses at 135 and 150° C.

Figure 27:
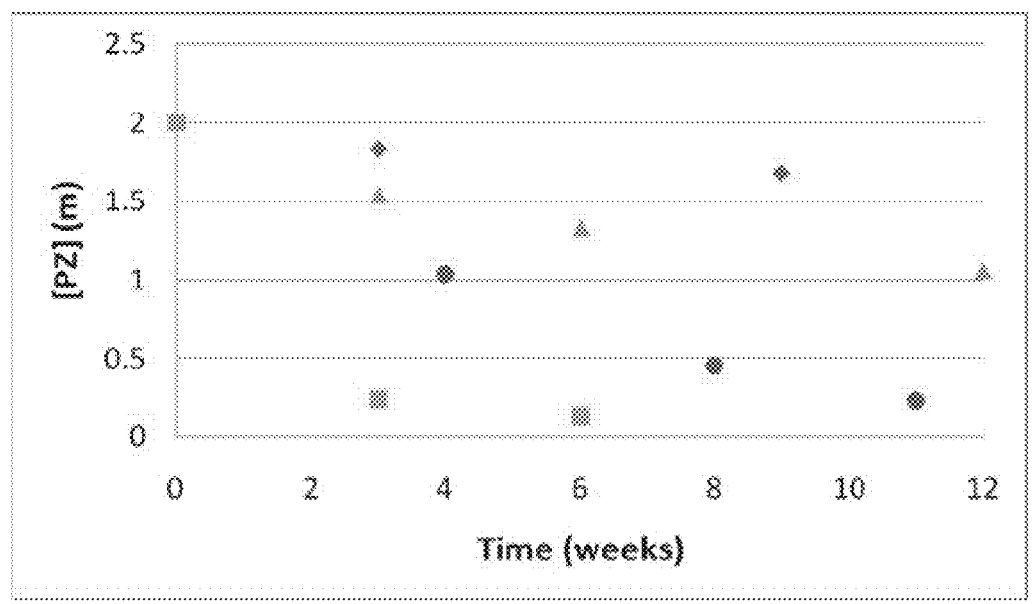
FIG. 27 shows PZ concentration over time in a 7 m MEA/2 m PZ aqueous solution with a loading of 0.4 moles $CO_2$/mole of alkalinity at varying temperatures. diamond=100° C., triangle=120° C., circle=135° C., and square=150° C.

FIG. 27 shows the loss of PZ for the same time points.

Piperazine shows more substantial losses as a percentage of the initial amine than MEA with measurable losses even at 100° C. When concentration is taken into account, piperazine reacts with oxazolidone over 5 times faster than MEA. This is expected from the comparison of the species rate constants with $CO_2$.

Piperazine reacted over five times faster than MEA with oxazolidone and that is why on the IC/MS chromatogram there is a much larger concentration of MEA/PZ products than MEA only products. This observation is slightly exaggerated since MEA/PZ products will not form an equilibrium concentration of imidazolidones as they do not have an alcohol group for ring closing and as such will remain in polymeric form and are all detected by IC. The temperature dependence of these reactions is much lower than that of the MEA only system.

Disproportionation of AEP

AEP will disproportionate at elevated temperature to make an equilibrium mixture of AEP, PZ, and DAEP as follows:

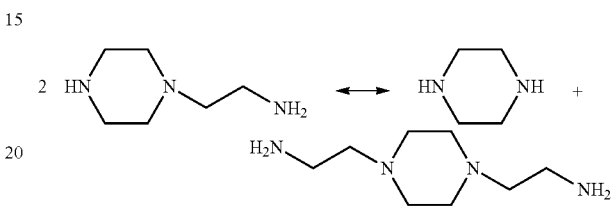

Figure 28:
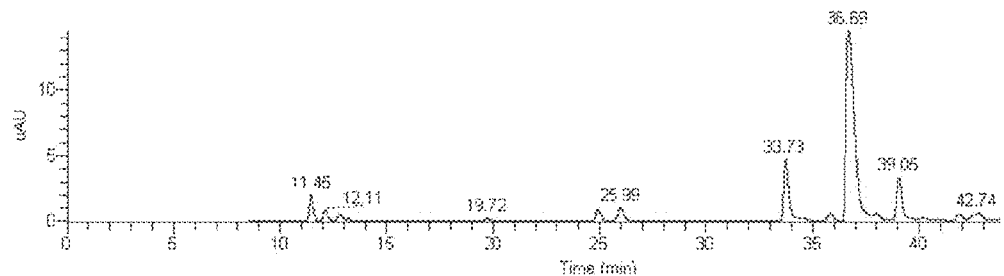
FIG. 28 shows an IC/MS chromatogram of a 2.33 m 1-(2-aminoethyl)piperazine aqueous solution with a loading of 0.4 moles of $CO_2$ per mole of alkalinity held at 135° C. for 4 weeks.

FIG. 28 shows the IC/MS chromatogram of a 2.33 m 1-(2-aminoethyl)piperazine aqueous solution with a loading of 0.4 moles of $CO_2$ per mole of alkalinity held at 135° C. for 4 weeks.

The peak at 36.7 minutes corresponds to AEP with a mass of 129. The peak at 33.7 min has a mass of 86 and corresponds to piperazine which was also found in the original solution, but the amount of PZ has increased in the sample. The peak at 39.1 min corresponds to the addition of an aminoethyl group onto AEP to make 1,4-piperazinediethanamine.

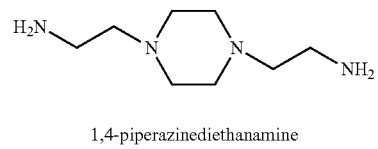 [SMILES: NCCN1CCN(CCN)CC1]

1,4-piperazinediethanamine

These products are the same as the ones found in the blended MEA/PZ system which formed AEP as an intermediate. The peak at 39.1 min and PZ correspond to a disproportionation reaction like the ones found in HEP and MDEA degradation due to the tertiary amine where the aminoethyl group dissociates from the AEP molecule and reattaches to another molecule.

Innovative Synthesis of Useful Triamines

Daive (2009) performed experiments to quantify the loss of MEA and PZ as degradation products. We propose to make use of his chemistry to synthesize a useful solvent.

It has been proposed to produce AEP more selectively from MEA by using a much greater ratio of piperazine to MEA. In the experiments by Davis (2009) the ratio of PZ to MEA was 2/7. The apparent production of products from the reaction of MEA with its oxazolidinone was less than ⅓ of the total products. If the PZ/MEA is increased by a factor of ten to about 3/1, the production of products other than AEP and DAEP will be less than 3%. In a solvent with a nominal PZ concentration of 8 m, the appropriate MEA concentration would be less than 2.7 m.

The synthesis of AEP in the solvent blend can be achieved by feeding MEA batchwise or continuously to the circulating solvent while maintaining an MEA concentration less than 2.7 m. For example, the solvent system could be charged with 7 m PZ and 2.0 m MEA. If 20% of the solvent inventory is at 150° C., half of the MEA in the total inventory will react to AEP and DAEP in about 5 weeks. After 10 weeks the solvent will contain about 5.5 m PZ, 1.5 m AEP, and 0.5 m MEA. After another 10 weeks the solvent will be about 5.1 m PZ, 1.9 m AEP, and 0.1 m MEA.

This in situ method may also be prepare useful solvent blends from PZ and aminomethylpropanol (AMP) or mono isopropanolamine (MIPA). These primary amines degrade in the same way as MEA. Their respective oxazolidinones will react with PZ to produce molecules analogous to AEP:

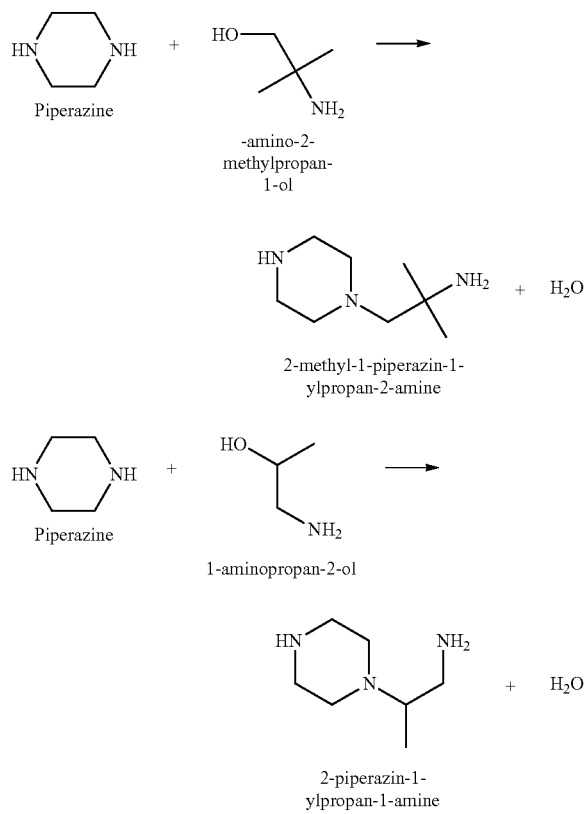

These solvents will also disproportionate to equilibrium mixtures of the substituted piperazines:

For alkanolamines with 2 carbons between the alcohol and the N:

PZ+HO—CR1R2-CR3R4-NHR7→PZ—CR1R2-CR3R4-NHR5+H2O between the alcohol and the N:

PZ+HO—$CR_1R_2$—$CR_3R_4$—$CR_5R_6$=$NHR_7$→PZ—$CR_1R_2$—$CR_3R_4$—$NHR_5$+$H_2O$ where $R_1$ to $R_7$ may be —H, —$CH_3$, or —$C_2H_5$.

Example 5

Amine Blends Using Concentrated Piperazine

Recent studies show 8 m piperazine (40 wt % PZ) has superior performance to the previous industry standard, 7 m monoethanolamine (30 wt % MEA). At process conditions, 8 m PZ has double the absorption rate and cyclic $CO_2$ capacity of 7 m MEA. Compared to MEA, PZ is more stable at high temperature and less prone to oxidation. Also, 8 m PZ has lower volatility than 7 m MEA. These physical and chemical advantages of 8 m PZ translate into an expected energy cost of 220 kWh/tonne $CO_2$ with optimized process design, which is the new standard for amine scrubbing.

The major disadvantage of 8 m PZ is limited solvent solubility, where solid precipitation occurs at both low and high $CO_2$ loading. While 8 m PZ can be safely used as an aqueous solvent at its optimum loading range (between 0.26 and 0.42 mol $CO_2$/equivPZ) above 20° C., it can be problematic in case of process upsets and temperature fluctuation. Advanced control mechanisms can help ensure proper operation, though these would incur additional cost and demand advanced handling techniques. Due to its solubility limitations, historically PZ has been mainly used at low concentration (<10 wt %) as a promoter for amines with slow reaction rates. However, most of these PZ-promoted solvents lose one or more other performance advantages of 8 m PZ because the amount of PZ present is too low.

This example evaluates the performance of amine blends using concentrated PZ (25-35 wt %). Using a larger amount of PZ is expected to maximize the advantages of PZ. Since the solid solubility window for PZ solvents becomes more limited with increased PZ, slightly reducing the PZ from 8 m by replacing it with other highly performing amines will improve or eliminate the precipitation problem. The characterized blends are 6 m PZ/2 m hexamethylenediamine (HMDA), 6 m PZ/2 m diaminobutane (DAB), 6 m PZ/2 m bis(aminoethyl)ether (BAE), 5 m PZ/2 m N-2(aminoethyl)

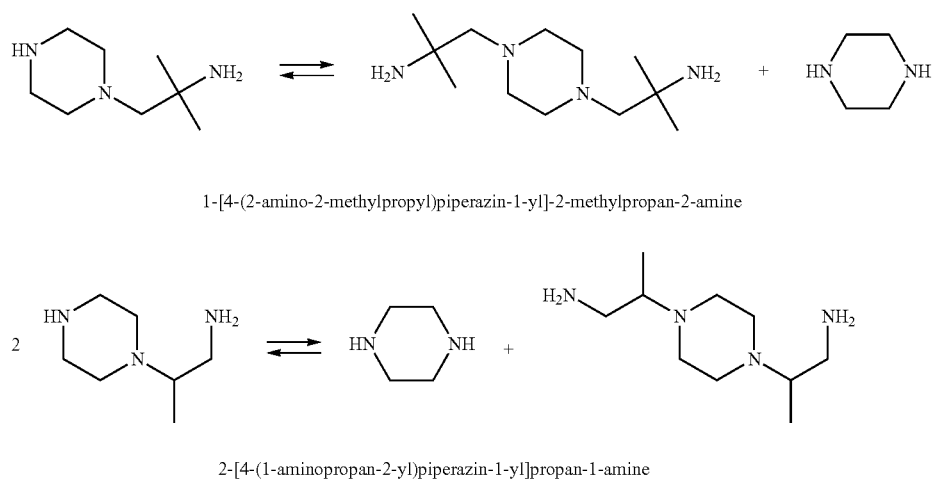

piperazine (AEP), and 5 m PZ/2.3 m 2-amino 2-methylpropanol (AMP). The chemical structures of the amines are in Table 7.

TABLE 7

Molecular structure of amines used in new blends with concentrated PZ

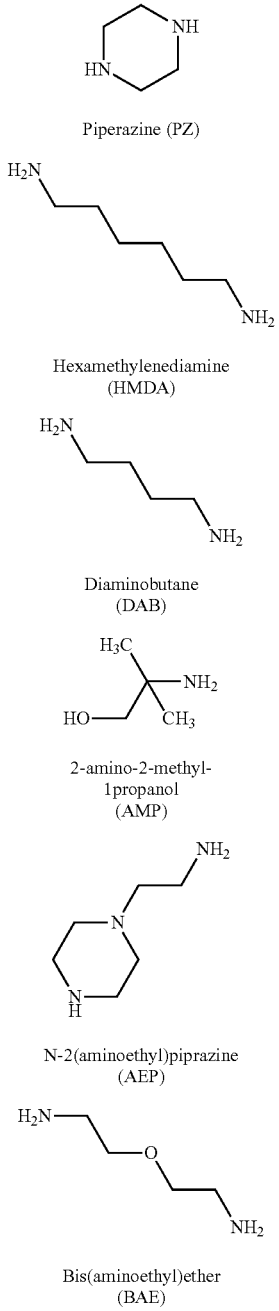

Piperazine (PZ)

Hexamethylenediamine (HMDA)

Diaminobutane (DAB)

2-amino-2-methyl-1propanol (AMP)

N-2(aminoethyl)piprazine (AEP)

Bis(aminoethyl)ether (BAE)

The blends were tested experimentally at relevant process conditions for solid precipitation limits, absorption rate, $CO_2$ cyclic capacity, heat of $CO_2$ absorption, rates of thermal and oxidative degradation, and amine volatility. Previous modelling for coal flue gas (12 kPa $CO_2$) shows 8 m PZ to have the best energy performance when the absorber operates with the solvent having equilibrium partial pressure ($P_{CO2}^*$) of 0.5 and 5 kPa at 40° C. at the top and bottom of the absorber, respectively. Thus, the nominal lean and rich loading for a solvent are defined as the liquid $CO_2$ loading (mol $CO_2$/equiv N) that correspond to $P_{CO2}^*$ of 0.5 and 5 kPa at 40° C., respectively. It is important to evaluate solvents within the range of these conditions because it provides a common basis for comparison.

This example offers a comprehensive evaluation of solvents where several important properties are presented together and interpreted interdependently to demonstrate the trade-off necessary in choosing solvents. Advanced parameters are introduced to interpret basic solvent properties, which can be used directly to suggest process performance such as required absorber packing area, maximum stripper operating temperature and pressure, and heat exchanger size. Also, a review of published results on other PZ blends is included in order to evaluate new solvents in relation to their competitors. The new PZ blends are compared against 1) base case amine solvents such as 8 m PZ and 7 m MEA, 2) blends with less PZ concentration (20 wt %) including 4 m PZ/4 m 2-methylpiperazine (2MPZ), 3.75 m 1-methylpiperazine (1MPZ)/3.75 m PZ/0.5 m 1,4-dimethylpiperazine (1,4-DMPZ), 5 m MDEA/5 m PZ, and 3) blends with low PZ concentrations (10 wt %) such as 7 m methydiethylamine (MDEA)/2 m PZ, 7 m MEA/2 m PZ, and 4 m AMP/2 m PZ.

Results $CO_2$ Absorption Rate

The absorption rate of $CO_2$ was measured at 40° C. and variable $CO_2$ loading ($\alpha_{CO2}$) using a bench scale wetted wall column. The experimental apparatus and methods are identical to those used by Chen et al. (Energy Procedia 2011). The measured rate is reported as $k_g'$, which is the liquid side mass transfer coefficient, defined as the ratio of the $CO_2$ mass transfer flux over the liquid side driving force expressed in partial pressure units (Equation 1).

$$k_g' = \frac{CO_2 \text{ flux}}{\left(P_{CO_2,interface} - P_{CO_2,bulk\ solution}\right)} \quad (1)$$

Absorption of $CO_2$ by aqueous amines is controlled by diffusion with fast chemical reaction in the liquid boundary layer. In most practical absorber conditions, the pseudo first order (PFO) approximation can be applied to the kinetics of $CO_2$ and amine reaction, which assumes the concentration of free amine is constant across the reaction boundary layer and equal to the bulk concentration. In this approximation, $k_g'$ is a function of the diffusivity of $CO_2$ in the liquid ($D_{CO2}$), the reaction rate constant of $CO_2$ and the amine ($k_2$), the free amine concentration in the bulk solution, and the Henry's constant of $CO_2$ over the solvent ($H_{CO2}$):

$$k_g' \approx \frac{\sqrt{D_{CO_2} k_2 [\text{Amine}]_b}}{H_{CO_2}} \quad (2)$$

While it is common to use $k_2$ as the key property when comparing absorption rates of different amines, it neglects the important differences in $D_{CO2}$, speciation, and physical solubility between solvents. The use of $k_g'$ gives more comprehensive and representative comparison of the practical $CO_2$ absorption rates in a real absorber.

Figure 29:
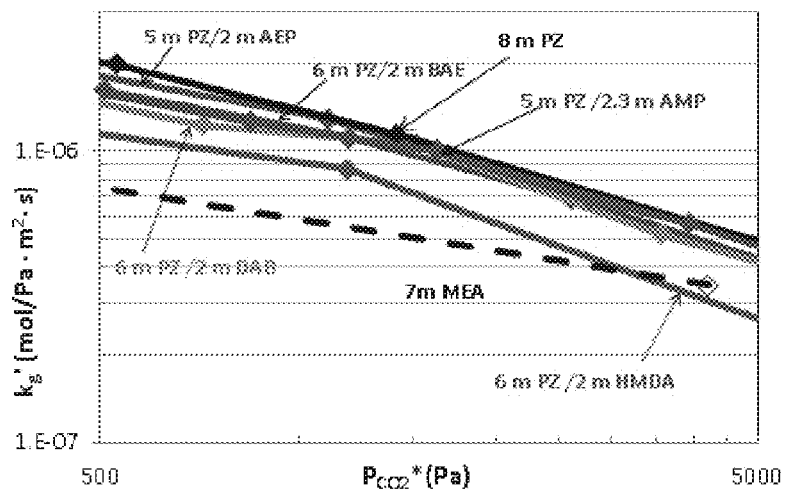
FIG. 29 shows $CO_2$ absorption rate at 40° C. for concentrated PZ blends. Compared with 8 m PZ and 7 m MEA (solid and dashed black lines).
Figure 30:
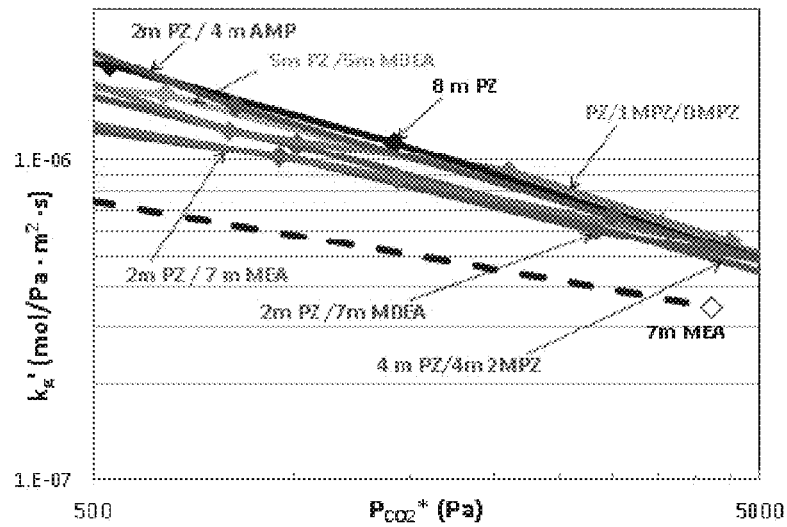
FIG. 30 shows $CO_2$ absorption rate at 40° C. for other PZ blends. 7 m MDEA/2 m PZ, 5 m MDEA/5 m PZ, PZ/1MPZ/1,4DMPZ, 4 m 2MPZ/4 m PZ (Chen 2011); 7 m MDEA/2 m PZ (Dugas 2009); 4 m AMP/2 m PZ (Li et al., Characterization of piperazine/2-aminomethylpropanol).

The measured rate at 40° C. for the concentrated PZ blends and other PZ blends is shown in FIGS. 29 and 30. $k_g'$ is plotted against $P_{CO2}^*$ between 0.5 and 5 kPa, which represents solvent loading at the top and bottom of a typical absorber. The results for the blends are compared against 8 m PZ and 7 m MEA (Dugas R. 2009).

Concentrated PZ blends have similar $k_g'$ to 8 m PZ, with the exception of 6 m PZ/2 m HMDA, which is slower than 8 m PZ and close to 7 m MEA at rich loading. The low rate of 6 m HMDA/2 m PZ is due to its high viscosity and higher lean loading (Table 8). High viscosity leads to lower $D_{CO2}$; and a higher lean loading corresponds to liquid speciation with less free amine for reaction, both contribute to a lower value of $k_g'$ (Equation 2). The rates of blends with less PZ are in the same range as 8 m PZ and most of the concentrated PZ blends (FIG. 30).

For each solvent, $k_{g\,avg}'$ is calculated for an isothermal absorber at 40° C. for coal flue gas and 90% $CO_2$ removal. The $P_{CO2}$ at the bottom and top of the absorber are 12 and 1.2 kPa, the rich and lean $P_{CO2}^*$ are 5 and 0.5 kPa. Experimental values at 40° C. are used to interpolate $k_g'$ that corresponds to $P_{CO2}^*$ at 5 and 0.5 kPa, which are then used to calculate the corresponding flux. $k_{g\,avg}'$ is a simple approach to account for the variation in $k_g'$ between the top and bottom of the absorber as the result of change in $CO_2$ loading. A linear profile of $CO_2$ driving force between the top and bottom of the column are assumed in the derivation of $k_{g\,avg}'$. Also, the gas film resistance is assumed to be negligible, and the overall gas side mass transfer coefficient ($K_G$) is equal to the liquid film

TABLE 8

Summary of composition, solvent solubility, and absorption rates for PZ blends

| PZ | | Amine | | Solid limit[a] | | $k_{g\,avg}'$ (40° C.) mol/Pa s m² | $A_p/V_g \times 10^3$ m²/ (m³/s) | $\mu^d$ cP | Lean ldg mol/mol N |
|---|---|---|---|---|---|---|---|---|---|
| m | wt % | m | wt % | Low | High | | | | |
| 6 | 29.5 | HMDA (2) | 13.3 | 0.35[c] | no | 4.9[h] | 3.1 | 15.4 | 0.37 |
| 6 | 30.5 | DAB (2) | 10.4 | 0.26[c] | no | 7.1[h] | 2.1 | 11.6 | 0.34 |
| 6 | 30.0 | BAE (2) | 12.1 | 0.30[c] | no | 7.3[h] | 2.1 | 11.7 | 0.33 |
| 5 | 25.5 | AEP (2) | 15.3 | 0.22 | no | 8.1[h] | 1.8 | 10.9 | 0.30 |
| 5 | 36.5 | AMP (2.3) | 10.8 | 0.2[b] | no | 7.5[f] | 2.0 | 9.5 | 0.33 |
| 5 | 21.3 | MDEA (5) | 29.4 | no | no | 8.5[e] | 1.8 | 13.2 | 0.21 |
| 4 | 19.8 | 2MPZ (4) | 22.9 | 0.11 | no | 7.1[e] | 2.1 | 10.5 | 0.30 |
| 3.75 | 18.4 | 1MPZ (3.75)/ 1,4DMPZ (0.5) | 21.4/3 | 0.19[c] | no | 8.5[e] | 1.8 | 12.4 | 0.23 |
| 2 | 11.3 | AMP (4) | 23.3 | no | no | 8.3[f] | 1.8 | 5.4 | 0.33 |
| 2 | 10.8 | MEA (7) | 26.7 | no | no | 6.9[g] | 2.2 | | 0.38 |
| 2 | 8.6 | MDEA (7) | 41.6 | no | no | 7.2[e] | 2.1 | 9 | 0.13 |
| 8 | 40 | none | | 0.26 | 0.42[c] | 8.5[g] | 1.8 | 10.8 | 0.31 |
| none | | MEA (7) | 30 | no | no | 4.3[g] | 3.5 | 3 | 0.43 |

[a]The $CO_2$ loading where solid/liquid transition occurs at 20° C. Solvent precipitates at loading lower than the lean limit and higher than the rich limit.
[b]Estimation based on measurements of PZ/AMP blends at other concentrations (Li H, Li L, Nguyen T, Rochelle GT, Chen J. Characterization of piperazine/2-aminomethylpropanol. *Energy Procedia* 2013; Presented at GHGT-11, Kyoto, Japan, Nov. 18-22, 2012. Energy Procedia, 2013).
[c]Lowest/highest loading where no precipitation was observed, solubility window at least reaches to this point
[d]The average viscosity between lean and rich loading at 40° C., also see Table 11.
[e]Chen X, Closmann F, Rochelle GT. Accurate Screening of Amines by the Wetted Wall Column. *Energy Procedia*. 2011; 4: 101-108.;
[f]Li H, Li L, Nguyen T, Rochelle GT, Chen J. Characterization of piperazine/2-aminomethylpropanol. Energy Procedia 2013; Presented at GHGT-11, Kyoto, Japan, Nov. 18-22, 2012. Energy Procedia, 2013.
[g]Dugas R. Carbon dioxide absorption, desorption, and diffusion in aqueous piperazine and monoethanolamine. PhD Dissertation, The University of Texas at Austin, Austin, Texas, 2009;
[h]Li L, Li H, Du Y, Namjoshi O, Rochelle GT. Absorption rates and CO2 solubility in new piperazine blends. Presented at GHGT-11, Kyoto, Japan, Nov. 18-22, 2012. Energy Procedia, 2013.

The measured $k_g'$ values can be used to predict rate performance in a real absorber. First, the log mean average absorption rate ($k_{g\,avg}'$) can be calculated using Equation 3:

$$k_{g_{avg}}' = \frac{Flux_{CO_2,LM}}{(P_{CO_2} - P_{CO_2}^*)_{LM}} \qquad \text{(Equation 3)}$$

$$= \frac{(Flux_{CO_2,top} - Flux_{CO_2,bottom})/ \mathrm{Ln}(Flux_{CO_2,top}/Flux_{CO_2,bottom})}{(P_{CO_2,top} - P_{CO_2,lean}^*) - (P_{CO_2,bottom} - P_{CO_2,rich}^*)/ \mathrm{Ln}\left(\frac{P_{CO_2,top} - P_{CO_2,lean}^*}{P_{CO_2,bottom} - P_{CO_2,rich}^*}\right)}$$

coefficient ($k_g'$). $k_{g\,avg}'$ is a useful parameter because it allows for simple comparison of absorption rate of solvents. Also, the $k_{g\,avg}'$ for each solvent can be used to calculate the required packing area ($A_p$) per volumetric unit of flue gas rate ($V_g$) using Equation 4:

$$\frac{A_p}{V_g} = \frac{Removal \cdot x_{CO_2} \cdot P/RT}{Flux_{CO_2,LM}} \qquad (4)$$

$$= \frac{90\% \cdot 12\% \cdot P/RT}{k_{g_{avg}}'(P_{CO_2} - P_{CO_2}^*)_{LM}}$$

The calculated kg'avg and Ap/Vg for each solvent at coal flue gas conditions are summarized in Table 8.

With higher absorption rate ($k_{g\,avg}'$), less packing ($A_p/V_g$) is required to achieve the same level of removal. Blends with different PZ concentration have about the same rate performance as 8 m PZ, and are about 1.5 to 2 times that of 7 m MEA. The amount of PZ in the solvent and the reaction kinetics of the other amine have little effect on the $k_g'$ of the blend. Instead, the variation in $k_g'$ strongly depends on solvent lean loading and viscosity.

Solid Solubility

The solid solubility limits for 8 m PZ were determined by measuring the transition temperatures of the solvent at various $CO_2$ loading. The same method was used to find the solubility limits for 5 m PZ/2 m AEP (Du Y, et al. Aqueous piperazine/N-(2-aminoethyl)piperazine for $CO_2$ capture. Energy Procedia 2013; Presented at GHGT-11, Kyoto, Japan, Nov. 18-22, 2012. Energy Procedia, 2013) and 4 m PZ/4 m 2MPZ (Rochelle G T, et al. Acidic gas removal by aqueous amine solvents. US Patent 2011/0171093 A1. Jul. 14, 2011). For 3.75 PZ/3.75/1MPZ/0.5 1,4 DMPZ, and the rich end boundary of 8 m PZ, the exact transition points cannot be easily measured. Instead, the points closest to the transition boundary at which the solvent is still soluble are reported. Precipitation is expected at loading lower than the measured boundary for 3.75 PZ/3.75 1MPZ/0.5 1,4 DMPZ, and at loading higher than the rich side boundary for 8 m PZ. For other PZ blends, the solvent solubility was tested at 0° C. or room temperature at loading close to the nominal lean and rich conditions. The measured solid/liquid transition boundaries for the blends are shown in FIG. 31. The solubility windows for the blends at 20° C. are summarized in Table 8.

None of the PZ blends have solubility limitations at rich loading, which is an advantage over 8 m PZ which precipitates at $CO_2$ loading of 0.45 mol/mol N up to 40° C. At room temperature, 6 m PZ/2 m HMDA precipitates at $CO_2$ loading lower than 0.3, which is more limiting than 8 m PZ. Other PZ blends have either less restricting solubility boundaries in the low loading range than 8 m PZ or no precipitation.

$CO_2$ Solubility

The equilibrium partial pressure of $CO_2$ ($P_{CO2}^*$) is measured at low temperature (20-100° C.) using the WWC (Chen X, Closmann F, Rochelle G T. Accurate Screening of Amines by the Wetted Wall Column. Energy Procedia. 2011; 4: 101-108), and high temperature (100-160° C.) using a total pressure apparatus. The apparatus and method of the total pressure experiment are identical to those used by Xu (Xu Q. Thermodynamics of CO2 loaded aqueous amines. The University of Texas at Austin, Austin, Tex., 2011). The results from both experiments are regressed together using a semi-empirical model which expresses $P_{CO2}^*$ as a function of temperature and $CO_2$ loading (Equation 5).

$$\ln(P_{CO_2}^*) = a + \frac{b}{T} + c \cdot \alpha_{CO_2} + d \cdot \alpha_{CO_2}^2 + e\frac{\alpha_{CO_2}}{T} + d\frac{\alpha_{CO_2}^2}{T} \quad (5)$$

The parameters of the model for each solvent are summarized in Table 9.

Thermal Degradation

Thermal degradation experiments were performed at 135-175° C. The experimental methods are describes by Freeman (Freeman S A. Thermal degradation and oxidation of aqueous piperazine for carbon dioxide capture. PhD Dissertation, The University of Texas at Austin, Austin, Tex., 2010) and Namjoshi (Namjoshi O, Du Y, Rochelle G T. Thermal degradation of piperazine blends with diamines. Presented at GHGT-11, Kyoto, Japan, Nov. 18-22, 2012. Energy Procedia, 2013). Amine degradation was measured as the change in amine concentration with time, and the degradation rate is reported as the apparent first order rate constant of amine loss ($k_1$). For a blend, $k_1$ values can be measured for each amine and also for the total amines (TA) in the solvent. The degradation reactions are assumed to be first order with amine concentration. Thus, using $k_1$ measurements at multiple temperatures, the activation energy ($E_{act}$) for degradation can be calculated using the Arrhenius equation for reaction rate constants:

$$k_1 = A \cdot e^{-\frac{E_{ACT}}{RT}} \quad (6)$$

For a blend, $E_{act}$ can be calculated for each amine species and for the total amine.

TABLE 9

Parameters for the semi-empirical model (Equation 5) for PZ blends

| (m) PZ (m) Am | a | b | c | d | e | f | $R^2$ |
|---|---|---|---|---|---|---|---|
| 6/2 HMDA[c] | 0 | 0 | 230 ± 8 | −368 ± 21 | −72489 ± 2900 | 130983 ± 7402 | 1.000 |
| 6/2 DAB[c] | 41.2 ± 4.1 | −16399 ± 1231 | −27.3 ± 10.4 | 0 | 30302 ± 4312 | −16358 ± 6569 | 0.992 |
| 6/2 BAE[c] | 0 | 0 | 190 ± 7 | −264 ± 18 | −56669 ± 2386 | 91862 ± 6373 | 1.000 |
| 5/2 AEP[c] | 58.3 ± 12.3 | −17587 ± 4184 | −138 ± 81 | 200 ± 131 | 42830 ± 27306 | −47262 ± 44107 | 0.998 |
| 5/2.3 AMP[b] | 23.9 ± 6.6 | −6575 ± 2527 | 88.5 ± 35.6 | −160 ± 47 | −28165 ± 13518 | 60725 ± 17866 | 0.999 |
| 2/4 AMP[b] | 31.4 ± 4.2 | −8654 ± 1562 | 32.4 ± 23.1 | −55.9 ± 30.9 | −9562 ± 8362 | 22848 ± 10997 | 0.999 |
| 4/4 2MPZ[a] | 40.1 ± 0.8 | −12807 ± 266 | −21.3 ± 2.4 | 0 | 14114 ± 837 | 0 | 0.999 |
| 3.75/(3.75) 1MPZ (0.5) 1,4DMPZ[a] | 34.5 ± 0.1 | −10629 ± 54 | 0 | 0 | 7578 ± 120 | 0 | 1.000 |
| 5/5 MDEA[a] | 36.1 ± 0.2 | −11199 ± 173 | 0 | −29.1 ± 4.3 | 10551 ± 772 | 0 | 1.000 |
| 2/7 MDEA* | 34.2 ± 0.4 | −9807 ± 137 | 0 | −30.4 ± 3.1 | 8927 ± 345 | 0 | 0.999 |
| 2/7 MEA* | 20.5 ± 7.6 | −6364 ± 2521 | 95.8 ± 46.8 | −144 ± 70 | −27747 ± 15544 | 52307 ± 23248 | 0.999 |
| 8 m PZ[a] | 35.3 ± 0.3 | −11054 ± 120 | 0 | −18.9 ± 2.7 | 4958 ± 347 | 10163 ± 1085 | 0.993 |
| 7 m MEA[a] | 38.6 ± 0.4 | −12379 ± 139 | 0 | −16 ± 2.5 | 3556 ± 231 | 8702 ± 932 | 0.994 |

[a]Xu Q. Thermodynamics of CO2 loaded aqueous amines. The University of Texas at Austin, Austin, Texas, 2011.;
[b]Li H, Li L, Nguyen T, Rochelle GT, Chen J. Characterization of piperazine/2-aminomethylpropanol. Energy Procedia 2013; Presented at GHGT-11, Kyoto, Japan, Nov. 18-22, 2012. Energy Procedia, 2013;
[c]Li L, Li H, Du Y, Namjoshi O, Rochelle GT. Absorption rates and CO2 solubility in new piperazine blends. Presented at GHGT-11, Kyoto, Japan, Nov. 18-22, 2012. Energy Procedia, 2013.
*Regressed with low temperature data (WWC) only, high temperature data not included While the rate of amine loss increases with increase in temperature, the energy performance of the process improves with higher stripper operating temperature. Stripper operating temperature is limited by the rate of thermal degradation, and the optimum corresponds to the maximum tolerable rate of amine loss. Previous work by Davis suggests the acceptable rate of degradation ($k_1$) for 7 m MEA is $2.9 \times 10^{-8}$ s$^{-1}$ with stripper temperature at 121° C. This optimum is calculated by the trade-off between the cost of MEA loss and the energy benefits of higher stripper temperature and pressure (Davis J. *Thermal degradation of aqueous amines used for carbon dioxide captuer*. PhD Dissertation, The University of Texas at Austin, Austin, Tex., 2009.). Assuming this trade-off is consistent for different amines, the optimum stripper operating temperature ($T_{max}$) for each solvent is defined as the temperature which corresponds to an overall amine degradation rate of $2.9 \times 10^{-8}$ s$^{-1}$. $T_{max}$ can be calculated using $k_1$ and $E_{act}$ measured at the practical amine concentration and $CO_2$ loading, which is important as $k_1$ depends strongly on these conditions (Freeman S A. Thermal degradation and oxidation of aqueous piperazine for carbon dioxide capture. PhD Dissertation, The University of Texas at Austin, Austin, Tex., 2010.). In cases where $E_{act}$ is not available, the $E_{act}$ of other amines with similar structures and degradation mechanisms is used. This approximation is acceptable since the $E_{act}$ does not change significantly between amines with similar degradation characteristics. (Freeman S A. Thermal degradation and oxidation of aqueous piperazine for carbon dioxide capture. PhD Dissertation, The University of Texas at Austin, Austin, Tex., 2010.). The results for $k_1$ at 150° C., $E_{act}$, and $T_{max}$ for each blend are summarized in Table 10. The blends are compared against the degradation rate of the amine by itself.

of PZ with MEA, MDEA, and AMP all degrade at much higher rates than the amines if used by themselves. This is because PZ, as a strong nucleophile, will react with alkanolamines (or their respective oxalzolidinone) such as MEA, MDEA and AMP in a blend and result in additional degradation pathways. (Freeman S A. *Thermal degradation and oxidation of aqueous piperazine for carbon dioxide capture*. PhD Dissertation, The University of Texas at Austin, Austin, Tex., 2010.)

Process Performance

The values of the following properties for all PZ blends are summarized in Table 11.

Solvent Capacity ($\Delta C_{solv}$)

The nominal operation lean and rich loading with $P_{CO_2}^*$ of 0.5 and 5 kPa at 40° C. are calculated for each solvent using the semi-empirical model (Equation 5) and its regressed parameters (Table 9). The solvent capacity can then be calculated using the difference between the lean and rich loading ($\Delta \alpha_{CO_2}$) and the total alkalinity in solution (Equation 7):

$$\Delta C_{solv} = \frac{(\alpha_{rich} - \alpha_{lean}) \cdot \text{mol alkalinity}}{\text{kg(amine} + H_2O)} = \frac{\text{mol } CO_2}{\text{kg(amine} + H_2O)} \quad (7)$$

$\Delta C_{solv}$ is the difference in $CO_2$ concentration between lean and rich loading, it represents the amount of $CO_2$ removed per unit mass of solvent (amine and $H_2O$). With higher $\Delta C_{solv}$, less solvent is required to remove the same amount of $CO_2$. $\Delta C_{solv}$ directly relates to the sensible heat requirement, pump work, and the optimum design of the cross-exchanger.

The $\Delta C_{solv}$ for concentrated PZ blends are about 20% lower than 8 m PZ and 15% higher than 7 m MEA. 6 m PZ/2 m

TABLE 10

Summary of thermal degradation rate, activation energy, and maximum stripper temperature for PZ blends and amines in the blends

| PZ (m)/ | | Blend | | | | | | | | Amine | | | |
|---|---|---|---|---|---|---|---|---|---|---|---|---|---|
| | | $k_1 (\times 10^9)$* | | $T_{max}$ | $E_{act}^b$ | | | | | $k_1^* \times 10^9$ | $T_{max}$ | $E_{act}$ | |
| Amine (m) | $\alpha_{CO_2}$ | PZ | Am | TA$^a$ | ° C. | kJ/mol | Ref | Amine m | $\alpha_{CO_2}$ | | ° C. | kJ/mol | Ref |
| 6/2 HMDA$^c$ | 0.4 | / | / | 7.5 | 161 | PZ | [11] | 8 | 0.3 | 9$^c$ | 160 | PZ | [10] |
| 6/2 DAB$^c$ | 0.4 | 9 | 90 | 13 | 157 | PZ | [11] | 8 | 0.4 | 147$^c$ | 127 | PZ | [11] |
| 6/2 BAE$^c$ | 0.35 | 6.9 | 7.2 | 7.0 | 162 | PZ | [11] | 8 | 0.4 | 11$^c$ | 158 | PZ | [11] |
| 5/2 AEP | 0.3 | 10 | 28 | 15 | 155 | PZ | [8] | 2.33 | 0.4 | 1306$^d$ | 121 | PZ | [10] |
| 5/2.3 AMP | 0.4 | 90 | 256 | 133 | 138 | 99 | [7] | 7 | 0.4 | 86 | 137 | MEA | [10] |
| 4/4 2MPZ | 0.3 | / | / | 16 | 155 | PZ | [10] | 8 | 0.3 | 25 | 151 | PZ | [10] |
| 3.75/3.75 1MPZ/ 0.5 1,4DMPZ | 0.3 | 8 | / | 10 | 159 | PZ | [10] | 8 (1MPZ) | 0.3 | 36 | 148 | PZ | [10] |
| 2/7 MEA | 0.4 | 1200 | 683 | 608 | 104 | 84 | [10] | 7 | 0.4 | 828 | 121 | 157 | [10] |
| 2/7 MDEA | 0.11 | 486 | 42 | 61 | 138 | PZ | [20] | 7 | 0.1 | 283 | 128 | MEA | [20] |
| 8 PZ | 0.3 | 6 | / | 6 | 163 | 184 | [10] | | | | | | |
| 7 MEA | 0.4 | / | 828 | 828 | 122 | 157 | [10] | | | | | | |

*$k_1$ is the apparent rate of amine loss at 150° C., with the unit of s$^{-1}$
$^b E_{act}$ is calculated based on the $k_1$ value for total amine loss (TA)
$^c$Extrapolated from data collected at 175° C. using listed $E_{act}$
$^d$Extrapolated from data collected at 135° C. using listed $E_{act}$ When PZ is used together with HMDA, BAE, 2MPZ, 1MPZ, which are thermally stable by themselves, the blends are also stable. DAB and AEP are both less stable amines, but when blended with PZ they do not affect the stability of PZ. Also, DAB and AEP are present at low concentration in the blends, the overall degradation rate of the blends is still competitive against other stable solvents. Also, AEP is identified as a major stable degradation product of PZ. Thus, in a blend of PZ and AEP, the two amines are close to chemical reaction equilibrium which inhibits degradation reactions. The blends HMDA has $\Delta C_{solv}$ (13%) lower than all other concentrated PZ blends and only slightly higher than 7 m MEA. $\Delta C_{solv}$ depends on delta loading, total concentration of alkalinity, and amine mass (Equation 7). Thus, it is sensitive to the molecular structure of the other amine in the blend and the total amine concentration. Blends using primary diamines (HMDA, DAB, BAE) and AEP have lower delta loading which results in lower $\Delta C_{solv}$. PZ blends using large amounts of hindered amines (2 m PZ/4 m AMP) or tertiary amines (MDEA) have large delta loading. For 5 m PZ/5 m MDEA, which also has a high concentration of alkalinity, its $\Delta C_{solv}$ is significantly higher (11%) than 8 m PZ.

The absorption rate and $\Delta C_{solv}$ of the PZ blends are compared in FIG. 32. Also plotted are results for the amines used in the blends and amino acids. In general, the absorption rate of the PZ blend (solid diamond) is better than that of the amines (empty diamonds). For the PZ/AMP blends, a higher ratio of amine/PZ resulted in higher rate and $\Delta C_{solv}$. The opposite was observed for PZ/MDEA, where a higher ratio of amine/PZ produced lower rates and $\Delta C_{solv}$. The PZ blend with the best properties is 5 m PZ/5 m MDEA, and the least attractive blend is 6 m PZ/2 m HMDA.

at the midpoint between the lean and rich loading of the solvent. Since $\Delta H_{abs}$ decreases with increased $CO_2$ loading, the practical $\Delta H_{abs}$ depends both on the pKa of the amine and the loading range of the solvent. Hindered primary amines (AMP) and their blends have good practical $\Delta H_{abs}$, as they typically have high pKa and low lean loading.

Maximum Stripper Pressure ($P_{max}$)

Solvents can be rated for energy performance by their maximum stripper operating pressure ($P_{max}$). A better solvent provides higher stripper pressure, which corresponds to lower $W_{cmpression}$ and lower overall work (Oyenekan B A, Rochelle G T. Alternative stripper configurations for $CO_2$ capture by

TABLE 11

Summary of lean/rich loading, capacity, and energy performance properties for PZ blends

| PZ (m)/ Amine (m) | $\alpha_{CO2}$ (mol/mol N) | | | Capacity | | $-H_{abs}^{a}$ (kJ/mol) | | $T_{max}$ | $P_{max}$ | | $\mu^b$ |
|---|---|---|---|---|---|---|---|---|---|---|---|
| | lean | rich | $\alpha_{CO2}$ | $\Delta C_{solv}$ | $\Delta C_\mu$ | $\alpha_{mid}^a$ | $\alpha_{lean}$ | °C. | bar | $P_{CO2}/P_{H2O}$ | cP |
| 6/2 HMDA | 0.37 | 0.43 | 0.06 | 0.55 | 0.49 | 68 | 75 | 161 | 20.1 | 2.61 | 15.4 |
| 6/2 DAB | 0.34 | 0.41 | 0.07 | 0.68 | 0.66 | 63 | 69 | 157 | 11.7 | 1.3 | 11.6 |
| 6/2 BAE | 0.33 | 0.41 | 0.07 | 0.69 | 0.66 | 70 | 72 | 157 | 14.2 | 1.8 | 11.7 |
| 5/2 AEP | 0.30 | 0.37 | 0.07 | 0.68 | 0.67 | 71 | 75 | 155 | 15.4 | 2.2 | 10.9 |
| 5/2.3 AMP | 0.33 | 0.43 | 0.09 | 0.70 | 0.71 | 71 | 77 | 128 | 5.3 | 1.4 | 9.5 |
| 5/5 MDEA | 0.21 | 0.35 | 0.13 | 0.98 | 0.91 | 69 | 74 | 138 | 7.2 | 1.52 | 13.2 |
| 4/4 2MPZ | 0.29 | 0.39 | 0.10 | 0.89 | 0.88 | 66 | 72 | 155 | 12.8 | 1.7 | 10.5 |
| 3.75/3.75 1MPZ 0.5 1,4DMPZ | 0.23 | 0.33 | 0.10 | 0.87 | 0.83 | 71 | 74 | 159 | 17.0 | 2.2 | $12.4^d$ |
| 2/4 AMP | 0.33 | 0.48 | 0.15 | 0.77 | 0.90 | 73 | 77 | 128 | 5.6 | 1.45 | 5.4 |
| 2/7 MEA | 0.38 | 0.46 | 0.09 | 0.59 | | 73 | 78 | 104 | 1.8 | 0.79 | |
| 2/7 MDEA | 0.13 | 0.28 | 0.15 | 0.80 | 0.82 | 68 | 72 | 138 | 6.3 | 1.17 | $9^c$ |
| 8 | 0.31 | 0.40 | 0.09 | 0.86 | 0.84 | 67 | 71 | 163 | 16.5 | 1.8 | 10.8 |
| 7 MEA | 0.43 | 0.53 | 0.10 | 0.50 | 0.67 | 72 | 76 | 121 | 3.8 | 1.1 | 3 |

$^a$Heat of absorption at the mid loading condition ($P_{CO2}* = 1.5$ kPa)
$^b$The average viscosity between lean and rich loadings at 40° C.
$^c$Measured at solvent lean loading ($P_{CO2}* = 0.5$ kPa)
$^d$Viscosity for 5 m PZ/2 m 1MPZ/1 m 1,4DMPZ. Ref [10].

Heat of Absorption ($\Delta H_{abs}$)

The heat of $CO_2$ absorption for each solvent can be extracted from the equilibrium data by applying the fundamental thermodynamic relationship to the semi-empirical model (Equation 5):

$$-\Delta H_{abs} = R \cdot \left(\frac{\partial \ln(P^*_{CO_2})}{\partial (1/T)}\right)_{P,x} = b + e \cdot \alpha_{CO_2} + f \cdot \alpha_{CO_2}^2 \quad (8)$$

The expression in Equation 8 requires constant pressure and composition of the system, which can be assumed to be valid as the changes in these values are small within the relevant range of process conditions. Xu Q. *Thermodynamics of $CO_2$ loaded aqueous amines*. The University of Texas at Austin, Austin, Tex., 2011. At constant stripper temperature, solvents with higher heat of absorption are expected to have lower overall energy requirement. Oyenekan B A, Rochelle G T. Energy performance of stripper configurations for $CO_2$ capture by aqueous amines. Industrial & Engineering Chemistry Research 2006; 45(8): 2457-2464.

Overall, the variation in the measured value of practical $\Delta H_{abs}$ for the PZ blends is less than 10 kJ/mol. 5 m PZ/2 m AEP, 6 m PZ/2 m BAE, 2 m PZ/7 m MEA, and the two PZ/AMP blends have higher practical $\Delta H_{abs}$ than 8 m PZ and competitive with 7 m MEA. The practical $\Delta H_{abs}$ is measured aqueous amines. American Institutue of Chemical Engineering Journal 2007; 53 (12): 3144-3154):

$$W_{total} = W_{reboiler} + W_{pump} + W_{compression} \quad (9)$$

$P_{max}$ can be calculated as the sum of the partial pressure of water and $CO_2$ exiting the stripper, with the partial pressure of the amines assumed to be negligible:

$$P_{max} = P_{CO_2}|_{T_{max}} + P_{H_2O}|_{T_{max}} = P'_{CO_2,lean}|_{T_{max}} + x_{H_2O} \cdot P_{H_2O,vap}|_{T_{max}} \quad (10)$$

The vapor pressure of water is calculated using data from the DIPPR database (DIPPR, 1998-Provo, Utah: BYU DIPPR, Thermophysical Properties Laboratory, 1998-Version 13.0.), and the partial pressure of water is assumed to follow Raoult's law. The partial pressure of $CO_2$ in the stripper is assumed to be at equilibrium with the lean loading of the solvent at Tmax, which can be calculated by integrating the thermodynamic relationship in Equation 8 from a standard temperature (40° C.) to Tmax:

$$\ln\left(\frac{P^*_{CO_2,lean}|_{T_{max}}}{P^*_{CO_2,lean}|_{40° C.}}\right) = \ln\left(\frac{P^*_{CO_2,lean}|_{T_{max}}}{0.5 \, kPa}\right) \quad (11)$$

$$= \frac{-\Delta H_{abs,lean}}{R}\left(\frac{1}{T_{max}} - \frac{1}{40° C.}\right)$$

Alternatively, $P_{CO_2,lean}*$ can be calculated using a semi-empirical model at solvent lean loading and Tmax.

Solvent $P_{max}$ depends most significantly on thermal stability ($T_{max}$). All thermally stable PZ blends have high $P_{max}$ (above 10 bar), whereas the alkanolamine blends (MEA, MDEA, AMP), which are thermally unstable with low $T_{max}$, have $P_{max}$ about 50-80% lower than the other blends. Solvent $P_{max}$ depends, to a lesser degree, on solvent $\Delta H_{abs}$ at lean loading. While 6 m/PZ 2 m BAE, 6 m PZ/2 m DAB, and 5 m PZ/2 m AEP, all have similar $T_{max}$, 5 m PZ/2 m AEP and 6 m PZ/2 m BAE have higher $P_{max}$ because of their high Habs.

$CO_2$ to Water Ratio ($P_{CO2}/P_{H2O}$)

$$\left.\frac{P_{CO_2}}{P_{H_2O}}\right|_{T_{max}} = \frac{P^*_{CO_2,lean}|_{T_{max}}}{x_{H_2O} \cdot P_{H_2O,vap}|_{T_{max}}} \tag{12}$$

Water is vaporized along with $CO_2$ during the stripping process, and the heat loss associated with this stripping steam contributes to the work loss at the reboiler. The ratio of $P_{CO2}$ and $P_{H2O}$ exiting the stripper represents the amount of $CO_2$ removed relative to heat loss through stripping steam. A high ratio of $P_{CO2}/P_{H2O}$ corresponds to more efficient stripping and better energy performance. Like $P_{max}$, $P_{CO2}/P_{H2O}$ increases with increase in solvent $\Delta H_{abs}$ and $T_{max}$. Solvents with high $P_{max}$ also have high $P_{CO2}/P_{H2O}$, but $P_{CO2}/P_{H2O}$ is more sensitive to variations in $\Delta H_{abs}$.

Cross-Exchanger Optimization

Cross-exchanger optimization involves evaluating the trade-off between the capital cost of the exchanger and the value of sensible heat requirement. The capital cost of the exchanger is a function of the cost per unit area (A$), solvent heat capacity ($C_p$), temperature difference between two solvent streams (A$\Delta$T), the liquid film heat transfer coefficient (h), solvent capacity ($\Delta C_{solv}$), and the temperature gain by the rich solvent (Equation 13).

$$\frac{HX\ cost}{mol\ CO_2} = \frac{A\$(T_{rich,out} - T_{rich,in}) \cdot C_p}{h \cdot \Delta T \cdot \Delta C_{solv}} \tag{13}$$

The sensible heat requirement is the result of cross-exchanger inefficiency, which increases with increase in $\Delta T$ and also depends on $C_p$ and capacity (Equation 14).

$$Q_{sensible} = \frac{C_p}{\Delta C_{solv}} \cdot \Delta T \tag{14}$$

In order to assign value to sensible heat, the equivalent electric work by the steam used in the reboiler is calculated assuming a Carnot cycle efficiency and 0.75 turbine efficiency (Equation 15), and W$ representing the cost per unit of electricity.

$$\frac{Sensible\ heat\ cost}{mol\ CO2} = W\$ \cdot 0.75 \frac{T_{steam} - T_{sink}}{T_{steam}} \cdot Q_{sensible} \tag{15}$$

The total cost associated with heating the solvent equals the sum of the two costs (Equation 16), $$\frac{Total\ cost}{mol\ CO2} = \tag{16}$$

$$\frac{A\$(T_{rich,out} - T_{rich,in}) \cdot C_p}{h \cdot \Delta T \cdot \Delta C_{solv}} + W\$ \cdot 0.75 \frac{T_{steam} - T_{sink}}{T_{steam}} \frac{C_p}{\Delta C_{solv}} \cdot \Delta T$$

Equation 16 assumes constant $\Delta T$, h, and $C_p$ across the exchanger. $\Delta T_{opt}$ for the cross exchanger can be solved, which minimize the total work. The quantity $T_{rich,out} - T_{rich,in}$ is assumed to have negligible dependence on $\Delta T$ and treated as a constant.

$$\Delta T_{opt} = \sqrt{\frac{(T_{rich,out} - T_{rich,in})T_{steam}}{0.75(T_{steam} - T_{sink})} \frac{A\$}{W\$} \frac{1}{h}} \tag{17}$$

$\Delta T_{opt}$ depends on the cost per unit area relative to the cost of electric work, Carnot efficiency, temperature change across the exchanger, and the heat transfer coefficient of the solvent (Equation 17). An empirical correlation for liquid heat exchangers by Colburn [18] relates the liquid film heat transfer coefficient (h) to the liquid velocity (G), heat capacity ($C_p$), heat conductivity (k), viscosity ($\mu$), and the diameter of the exchanger (Equation 18).

$$\frac{hD}{k} = 0.026\left(\frac{DG}{\mu}\right)^{0.8}\left(\frac{C_p\mu}{k}\right)^{0.3} \tag{18}$$

While viscosity differs significantly between solvents, other heat transfer properties remain relatively constant among different amines. Assuming the Colburn relationship is valid for common exchanger geometries, h can be written as dependent on viscosity only, where a is the combined constant for all other terms in the correlation (Equation 19).

$$h = \left(\frac{0.026\ G^{0.8} C_p^{0.3} k^{0.7}}{D^{0.2}}\right)\frac{1}{\mu^{0.5}} \cong \frac{a}{\mu^{0.5}} \tag{19}$$

Using $\Delta T_{opt}$ and h in the total cost equation, the minimum cost of heating with optimum exchanger design is inversely proportional to $\Delta C_{solv}$ and scales to solvent viscosity to the 0.25 power (Equation 20).

$$\left(\frac{Total\ cost}{mol\ CO_2}\right)_{minimum} = \tag{20}$$

$$\frac{2 \cdot C_p}{\Delta C_{solv}} \sqrt{\frac{0.75 \cdot A\$W\$(T_{rich,out} - T_{rich,in})(T_{steam} - T_{sink})}{a \cdot \mu^{-0.5} \cdot T_{steam}}}$$

Based on this cost dependence on solvent properties, a normalized solvent capacity can be defined:

$$\Delta C_\mu = \frac{\Delta C_{solv}}{(\mu_{\alpha_{mid}}/10\ cP)^{0.25}}$$

$\Delta C_\mu$ normalizes solvent capacity by viscosity of $CO_2$-loaded solvent relative to a standard viscosity value (10 cP, $\mu$ of loaded 8 m PZ). $\Delta C_\mu$ is a more direct representation of relative energy performance than mass-based capacity ($\Delta C_{solv}$, Equation 7). For PZ blends, 2 m PZ/4 m AMP has $\Delta C_{solv}$ less than 8 m PZ, but also viscosity that is about 50% of 8 m PZ. Thus, the $\Delta C_\mu$ for 2 m PZ/4 m AMP is about 10% better than 8 m PZ. Thus, the relative performance of a solvent can change significantly due to viscosity. The effect of pressure drop on heat exchanger performance was not included in this optimization. The velocity of the liquids (G) and the geometry of the exchanger are assumed to be constant.

Volatility

Amine volatility was studied using an equilibrium reactor with a re-circulating gas stream, with the gas phase composition analyzed online by a multi-component FTIR. The experimental apparatus and methods are described by Nguyen (Nguyen T, Hillard M, Rochelle G T. Amine volatility in CO2 capture. International Journal of Greenhouse Gas Control 2010; 4 (5) 707-715).

Intrinsic volatility of the amines was studied by measuring the VLE of amine-water systems. The Henry's constant is calculated from experimental data (Equation 22).

$$H_{amine,T} = \frac{P_{amine}}{x_{amine} \cdot \gamma_{amine}^{\infty}} \quad (22)$$

For Henry's constant experiments, dilute amine concentrations were used. At dilute conditions, the activity coefficient of the amine at infinite dilution ($\gamma_{amine}^{\infty}$) is approximately one, and the Henry's constant can be calculated from amine partial pressure ($P_{amine}$) measurements. A structure property correlation for $H_{amine}*$ was developed using experimental results and literature data (Equation 23).

$$\ln(H_{amine}(Pa)) = \text{Intercept} + B \cdot (1/313K - 1/T(K)) + \Sigma(\text{coefficient } i)(\# \text{ groups}) \quad (23)$$

TABLE 12

Parameters for the structural property correlation for $H_{amine}$ (Equation 23)

| Parameter | Value | Standard error |
|---|---|---|
| N | −7.10 | 0.49 |
| NH | −4.29 | 0.26 |
| O | −3.19 | 0.16 |
| $N_{cyc}$ | −2.83 | 0.16 |
| NH2 | −1.29 | 0.21 |
| OH | −0.34 | 0.19 |
| $O_{cyc}$ | 0 | 0 |
| C | 0.013 | 0.05 |
| CH3—(C) | 0.260 | 0.09 |
| CH3—($C_{cyc}$) | 0.281 | 0.20 |
| Ccyc | 0.660 | 0.07 |
| CH3—($N_{cyc}$) | 1.88 | 0.10 |
| CH3—(N) | 3.92 | 0.25 |
| Intercept | 6.95 | 0.31 |
| B | 6840 | 423 |

$H_{amine}$ for new amines can be predicted using Equation 23. The measured or predicted $H_{amine}$ for the amines used in the PZ blends at 40° C. are summarized in Table 13. High amine volatility leads to higher amine loss with the exit flue gas at the top of the absorber. For the amines used in the new PZ blends, BAE and AEP have lower $H_{amine}$ than PZ. HMDA and DAB have $H_{amine}$ slightly higher than PZ, but still lower than MEA. AMP is a volatile amine, with $H_{amine}$ about 3.5 times that of MEA.

While Henry's constant represents intrinsic volatility of the amine, the practical volatility of the solvent in the absorber also depends on the concentration of the amine in solution and solvent $CO_2$ loading. At zero $CO_2$ loading, the expected $P_{amine}$ over the solvent equals to $H_{amine}$ multiplied by the mole fraction of the amine in the liquid (Table 13). HMDA and DAB have high $H_{amine}$, but the volatility for 6 m/PZ 2 m HMDA and 6 m PZ/2 m DAB is not high due to the low concentration of the volatile amines.

TABLE 13

The practical Henry's constant and amine partial pressure at 40° C. for the PZ blends

| | Zero $CO_2$ loading | | Loaded solvent | | |
|---|---|---|---|---|---|
| PZ (m)/(m) Amine | $H_{amine}$ Pa | $P_{amine}$ Pa | $P_{amine}$ Pa | $P_{PZ}$ Pa | $\alpha_{CO2}$ |
| 6/2 m HMDA | 85 | 2.7 | | | |
| 6/2 m DAB | 83[#] | 2.6 | | | |
| 6/2 m BAE | 3.4[#] | 0.1 | | | |
| 5/2 m AEP | 14.4[#] | 0.5 | | | |
| 5/2.3 AMP | 350 | 12.8 | 5.7[c] | 0.6[c] | 0.3[c] |
| 5/5 m MDEA | 22.9 | 1.7 | 0.16 | 0.5 | 0.21 |
| 4/4 m 2MPZ | 66.8 | 4.2 | 0.85 | 0.1 | 0.32 |
| 3.75/3.75 m 1MPZ | 1MPZ 332 | 1MPZ 19.6 | | | |
| 0.5 m 1,4DMPZ | DMPZ 2183 | DMPZ 17.6 | | | |
| 2/7 m MEA | 98.7 | 10.7 | | | |
| 2/7 m MDEA | 22.9 | 2.5 | 0.61[d] | 0.18[d] | 0.1[d] |
| 8 m PZ | 50.9 | 6.4 | | 0.77[a] | 0.31 |
| 7 m MEA | 98.7 | 11.0 | 1.27[b] | | 0.43 |

[a]$\ln(P_{PZ}/X_{PZ}) = -123 + 21.6\ln(T) + 20.2\alpha - 18174\alpha^2/T$; Xu Q. Thermodynamics of CO2 loaded aqueous amines. The University of Texas at Austin, Austin, Texas, 2011.
[b]$\ln(P_{MEA}/X_{MEA}) = 30 - 8153/T - 2594\alpha^2/T$; Xu Q. Thermodynamics of CO2 loaded aqueous amines. The University of Texas at Austin, Austin, Texas, 2011.
[c]Ref Li H, Li L, Nguyen T, Rochelle GT, Chen J. Characterization of piperazine/2-aminomethylpropanol. Energy Procedia 2013; Presented at GHGT-11, Kyoto, Japan, Nov. 18-22, 2012. Energy Procedia, 2013;
[d]Ref Nguyen T, Hillard M, Rochelle GT. Amine volatility in CO2 capture. International Journal of Greenhouse Gas Control 2010; 4 (5) 707-715;
[#]Values predicted using Equation 23

$CO_2$ loading further reduces solvent volatility by reacting with free amine molecules and producing nonvolatile products. Experiments were performed for $CO_2$-water-amine systems and the $P_{amine}$ at absorber temperature was measured. $P_{amine}$ for $CO_2$ loaded solvents is much lower than $P_{amine}$ at zero loading for all solvents. $P_{amine}$ of AMP in loaded 5 m PZ/2.3 m AMP is still significantly higher than amines in other solvents. Comp o Comparisons should also be made for $P_{amine}$ against the environmental toxicity limit of the amine.

Oxidative Degradation

Oxidation of amines at absorber conditions was studied in the high-gas flow (HGF) and low-gas flow (HGF) apparatuses. The experimental conditions were 55-70° C. with 2% $CO_2$ in air (HGF) or oxygen (LGF) in most experiments. Oxygen mass transfer was provided by vigorous agitation (LGF) or sparging the liquid with a high gas rate of 7-8 L/min (HGF). Other details of the apparatuses have been reported previously (Sexton A J, Rochelle G T. Reaction Products from the Oxidative Degradation of Monoethanolamine. Industrial & Engineering Chemistry Research, 2011; 50 (2): 667-673).

Amine oxidation by molecular oxygen produces ammonia, heat-stable salts (primarily formate), and other products. Changes in amine concentration are often too low for precise quantification of the rate; therefore ammonia or total formate (formate+formamides) production is used to estimate the oxidation rate from amine solutions. The ratio of amine loss to formate (0.1-0.4) or ammonia (0.7-1) production was determined experimentally for MEA and PZ under a variety of conditions.

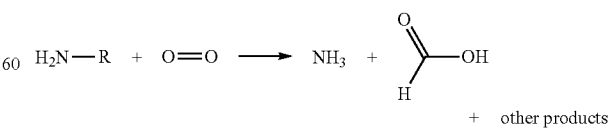

Results indicate for ammonia production in the HGF show a strong dependence on the type of catalyst present. Iron and copper was a more potent catalyst than iron alone for every amine or amine blend tested, whereas manganese behaved as a catalyst or an inhibitor in the presence of iron and copper.

TABLE 14

Ammonia production rates (mmol/kg/hr) from various solvents in the HGF apparatus with air and 2% $CO_2$ at 70° C. with iron (Fe), copper (Cu) and manganese (Mn) added at 1 mM concentration

| m Amine/ m PZ | Fe | Fe/Cu | Fe/Cu/Mn |
|---|---|---|---|
| 7 BAE | 5.46 | 13.9 | 13.6 |
| 8 AEP | 2.42 | — | — |
| 4 AMP/6 | <0.02 | 1.89 | 0.12 |
| 2 HMDA/6 | 0.03 | 1.35 | 2.56 |
| 2 DAB/6 | <0.02 | 1.1 | 0.53 |
| 8 m 1MPZ | <0.02 | — | — |
| 8 m 2PE | <0.02 | — | — |
| 8 m PZ | <0.02 | 0.37 | 0.03 |
| 7 MEA | 0.9 | 6.6 | 11.6 |

TABLE 15

Total formate production rates in various solvents in the LGF apparatus with oxygen and 2% $CO_2$ at 70° C. with various metals (SSM = Fe, Ni, Cr)

| m Amine/ m PZ | Total Formate Rate (mmol/kg/hr) | Catalyst |
|---|---|---|
| 2 AEP[a] | 0.089 | SSM + Mn |
| 2 AEP/5[a] | 0.076 | SSM + Mn |
| 2 HMDA/6 | 0.095 | SSM + Mn |
| MDEA[b] | 0.039 | SSM |
| 7 MDEA/2[b] | 0.072 | SSM |
| 4 m 2MPZ/4[c] | 0.021 | SSM + Mn |
| 8 m PZ[d] | 0.031 | SSM |
| 8 m PZ[a] | 0.026 | SSM + Mn |
| 7 MEA | 6.65 | Mn + Fe |
| 7 MEA | 3.64 | Fe |

[a]Du Y, et al. Aqueous piperazine/N-(2-aminoethyl)piperazine for CO2 capture. Energy Procedia 2013; Presented at GHGT-11, Kyoto, Japan, Nov. 18-22, 2012. Energy Procedia, 2013.;
[b]Closmann FB. Oxidation and thermal degradation of methyldiethanolamine/piperazine in CO2 capture. The University of Texas at Austin. Ph.D. Dissertation. 2011.;
[c]Sherman B, et al. Carbon capture with 4 m piperazine/4 m 2-methylpiperazine. Presented at GHGT-11, Kyoto, Japan, Nov. 18-22, 2012. Energy Procedia, 2013;
[d]Freeman SA. Thermal degradation and oxidation of aqueous piperazine for carbon dioxide capture. PhD Dissertation, The University of Texas at Austin, Austin, Texas, 2010.

MEA, BAE, and AEP all showed significant ammonia production in the presence of iron only, whereas AMP, HMDA, PZ, 1MPZ, and 2PE produced very little or no ammonia. In the presence of copper and iron, 8 m PZ was the most stable to oxidation.

Results from the LGF are similar to those from the HGF. The total formate rate for each experiment was calculated from the final sample only for consistency. Production of total formate in MEA was much greater than in straight PZ or any of the PZ blends tested. In both experiments, AEP and HMDA showed greater susceptibility to oxidation than straight PZ or PZ/2MPZ. Manganese, which is a strong catalyst of MEA oxidation, had little effect on the total formate rate in 8 m PZ.

The practical absorption rates ($k_g'$) of concentrated PZ blends are competitive against 8 m PZ and other PZ blends, which are about 1.5-2 times that of 7 m MEA. The only major exception is 6 m PZ/2 m HMDA which has a lower rate close to 7 m MEA. Practical absorption rate of PZ blends is not dependent on the concentration of PZ or the reaction kinetics of the other amine, it is a strong function of the viscosity and practical lean loading of the solvent. All PZ blends have no precipitation limitations in the rich loading range (0.45 mol/mol). With the exception of 6 m PZ/2 m HMDA, all PZ blends have either less restricting solubility boundary at lean loading (0.2 mol/mol) or no limitations. 6 m HMDA/2 m PZ, 6 m PZ/2 m DAB, 6 m PZ/2 m BAE, 5 m PZ/2 m AEP, 4 m PZ/4 m 2MPZ, and 3.75 m PZ/3.75 m 1MPZ/0.5 m 1,4DMPZ are thermally stable and have overall degradation rate ($k_1$) competitive with 8 m PZ. The $k_1$ for 8 m DAB, 2.33 m AEP, and 8 m 1MPZ are not stable by themselves, but do not affect the overall degradation rates when blended with PZ. Blends using PZ and its identified stable degradation products (AEP) tend to have reduced degradation rates as the amines reach reaction equilibrium. Blends using PZ and alkanolamines (MEA, MDEA, AMP) are thermally unstable, as PZ will react with the amine at a high rate. Concentrated PZ blends have capacity 20% lower than 8 m PZ, and 15% higher than 7 m MEA. The $H_{abs}$ of blends using AMP, BAE, and AEP are higher than 8 m PZ by about 5 kJ/mol. Solvents with the best energy performance have high $H_{abs}$, $T_{max}$, $P_{max}$, and $P_{CO2}/P_{H2O}$, which are as 6 m PZ/2 m HMDA, 6 m PZ/2 m BAE, and 5 m PZ/2 m AEP. The cost of heating the solvent, with optimized exchanger design, depends on the solvent capacity and viscosity to the 0.25 power. Comparing solvents based on performance of the cross exchanger shows 5 m PZ/5 m MDEA and 2 m PZ/4 m AMP as the best solvents. 6 m PZ/2 m HMDA and 6 m PZ/2 m DAB have similar performance to 7 m MEA. AMP has the highest intrinsic volatility, with $H_{amine}$ about 3.5 times MEA. HMDA and DAB have similar $H_{amine}$ as MEA, and BAE and AEP are non-volatile. The volatility of a solvent depends on the concentration of the volatile amine and $CO_2$ loading. 6 m PZ/2 m HMDA and 6 m PZ/2 m DAB are expected to have similar volatility as 8 m PZ because the concentration of the volatile amines are low. $CO_2$ loading reduces solvent volatility. 5 m PZ/2.3 m AMP at loaded conditions still has significant volatility relative to other solvents. MEA, BAE, and AEP are easily oxidized, with significant ammonia production in the presence of iron only; whereas AMP and HMDA produced very little or no ammonia. Liquid phase analysis on formate production confirms the relative oxidation rate of AEP and HMDA. 8 m PZ is still the most stable solvent, with low oxidation rate in the presence of iron and copper.

Blends using concentrated (25-35 wt %) piperazine (PZ) were characterized as solvents for $CO_2$ capture at typical coal flue gas conditions. The new blends are 6 m PZ/2 m hexamethylenediamine (HMDA), 6 m PZ/2 m diaminobutane (DAB), 6 m PZ/2 m bis(aminoethyl)ether (BAE), 5 m PZ/2 m aminoethylpiperazine (AEP), and 5 m PZ/2.3 m 2-amino 2-methyl-propanol (AMP). The $CO_2$ absorption rate of the blends was measured using a wetted wall column (WWC). The $CO_2$ vapor liquid equilibrium was measured at 20-160° C. Amine vapor pressure measurements are reported to show potential volatility at practical conditions. The rate of thermal degradation was measured from 135 to 175° C. Oxidative degradation was measured in two semi-batch experiments with different $O_2$ rate at absorber conditions. Advanced parameters are introduced to demonstrate the overall rate and energy performance of the solvents in a real process. The performance of 7 m MEA, 8 m PZ, and six other competitive PZ blends are evaluated based on previous results and presented as basis of comparison.

All of the PZ blends have better solubility window than 8 m PZ, with no precipitation at rich loading. The absorption rate of the concentrated PZ blends is similar to that of 8 m PZ and 1.5-2 times higher than 7 m MEA; the solvent capacity is about 20% lower than 8 m PZ and 15% higher than 7 m MEA. Among all of the PZ blends, 5 m PZ/5 m MDEA has the best combination of rate and capacity. Blends using HMDA, AEP, BAE, AMP, and MEA have a high heat of $CO_2$ absorption.

Blends using MEA, MDEA, and AMP are not thermally stable, while other blends have good thermal stability. The combination of high $H_{abs}$ and thermal stability leads to good overall energy performance, which is observed for 6 m PZ/2 m HMDA, 6 m PZ/2 m BAE and 5 m PZ/2 m AEP. AMP has relatively high volatility, whereas BAE and AEP are expected to have low volatilities. The only drawback of 6 m PZ/2 m BAE is its high oxidation rate. 6 m PZ/2 m HMDA and 6 m PZ/2 m DAB have good oxidative stability.

PZ blends using low viscosity amines will have high absorption rate, and tertiary and hindered amines will contribute to high capacity. Amines with high pKa will improve the blend $H_{abs}$. For thermal stability, alkanolamines should not be used together with PZ. Highly viscous blends such as 6 m PZ/2 m HMDA are expected to have 10-20% higher cost associated with cross-exchanger design and operation than solvents with low viscosity.

Example 6

Aqueous Piperazine/N-(2-Aminoethyl) Piperazine for $CO_2$ Capture

Amine scrubbing has shown the most promise for effective capture of $CO_2$ from coal-fired flue gas. Aqueous monoethanolamine (MEA) with a concentration between 15-30% has been previously used in similar applications such as $CO_2$ removal from natural gas and hydrogen, and is currently considered the state-of-the-art technology for $CO_2$ absorption/stripping because of its effectiveness for $CO_2$ capture and low cost of production. However, the low resistance to degradation, and low $CO_2$ capacity and $CO_2$ absorption rates of MEA lead to high capital and energy cost when MEA is used for $CO_2$ capture from coal-fired flue gas.

Concentrated piperazine (PZ) has been proposed as a possible alternative to 30 wt % MEA for $CO_2$ capture from coal-fired flue gas (Rochelle G T, Chen E, Freeman S A, Van Wagener D H, Xu Q, Voice A K. Aqueous piperazine as the new standard for CO2 capture technology. Chem Eng J 2011; 171(3):725-33.). PZ has about twice the $CO_2$ absorption rate and $CO_2$ capacity, and greater resistance to oxidative and thermal degradation than 30 wt % MEA, which can lower the heat duty for the stripper in amine scrubbing systems by approximately 5-10% (Freeman S A, Dugas R E, Van Wagener D H, Nguyen T, Rochelle G T. Carbon dioxide capture with concentrated, aqueous piperazine. Int J Greenh Gas Con 2010; 4(2):119-24.).

In spite of desirable characteristics, the application of concentrated PZ in industry may be limited by solid precipitation at both lean and rich $CO_2$ loading. At room temperature (22° C.), 8 m PZ requires a loading of 0.25 mol $CO_2$/mol alkalinity to stay in solution and also forms solids at high $CO_2$ loading.

Blending solvents already in use is one approach to combine desirable characteristics. A novel PZ-based blend, piperazine/N-(2-aminoethyl) piperazine (PZ/AEP), was investigated to remediate the precipitation of concentrated PZ without sacrificing its $CO_2$ capacity and absorption rate, resistance to degradation, and other desirable characteristics.

Materials and Methods

Solution Preparation

Aqueous PZ/AEP was prepared by melting anhydrous PZ (99%, Alfa Aesar, Ward Hill, Mass.) in water and AEP (99%, Alfa Aesar, Ward Hill, Mass.) mixture, and gravimetrically sparging $CO_2$ (99.5%, Matheson Tri Gas, Basking Ridge, N.J.) to achieve the desired $CO_2$ concentration. The concentration of $CO_2$ was determined by total inorganic carbon (TIC) analysis, described by Hilliard (Hilliard M D. A Predictive Thermodynamic Model for an Aqueous Blend of Potassium Carbonate, piperazine, and Monoethanolamine for Carbon Dioxide Capture from Flue Gas. The University of Texas at Austin, Austin, Tex., 2008.)

Solvent Solubility

The solid solubility of PZ/AEP with a total N concentration of 16 m was measured in a water bath over a range of PZ/AEP molar ratio (5/2, 4/2.67, 3/3.33), $CO_2$ loading (from 0 to 0.4 mol $CO_2$/mol alkalinity), and temperature (from 0 to 50° C.). The solid solubility measurements were based on visual observations and the method was described in detail by Freeman [5]. Solutions with desired properties were heated up to 50° C. in a water bath to melt precipitates in solution with lean $CO_2$ loading. While cooling slowly, the temperature at which the solution first began to crystallize or precipitate was regarded as the crystallizing transition temperature. Finally, the solution was heated again to carefully observe the temperature when the crystals fully melt and this was noted as the melting transition temperature. The difference between crystallizing and melting transition temperature, which is also called hysteresis, was minimized to 1° C. or less for most of the measured points by giving enough equilibrium time and repeating the melting-crystallizing process at transition temperatures.

Viscosity Measurements

Viscosity of 5 m PZ/2 m AEP was measured using a Physica MCR 300 cone and plate rheometer (Anton Paar GmbH, Graz, Austria). The method was also described by Freeman (Freeman S A. Thermal Degradation and Oxidation of Aqueous piperazine for Carbon Dioxide Capture. The University of Texas at Austin, Austin, Tex., 2011). The average value and standard deviation calculated from 10 individual measurements for each sample was reported.

Thermal Degradation

Thermal degradation was measured in ½-inch OD 316 stainless steel thermal cylinders. Cylinders were filled with 7 mL of amine solution with around 3 mL of headspace, sealed with two Swagelok® end caps, and placed in forced convection ovens maintained at the target temperature. Individual cylinders were removed from the ovens at each sampling point and then analyzed for degradation products, degradation rate, and $CO_2$ loading, using a Dionex ICS-2500 cation ion chromatograph, a Dionex ICS-3000 modular Dual Reagent-Free anion ion chromatograph (Dionex Corporation) and an infrared $CO_2$ analyzer (Horiba Instruments Inc., Spring, Tex.). The details of the experimental apparatus, procedure, and analytical methods are described by Freeman. (Freeman S A. Thermal Degradation and Oxidation of Aqueous piperazine for Carbon Dioxide Capture. The University of Texas at Austin, Austin, Tex., 2011; Freeman S A, Rochelle G T. Thermal Degradation of Aqueous piperazine for $CO_2$ Capture: 2. Product Types and Generation Rates. *Ind Eng Chem Res* 2012; 51(22):7726-35.)

Oxidation

Oxidative degradation experiments for 8 m PZ and 2 m AEP spiked with 0.05 mM $Cr^{3+}$, 01 mM $Ni^{2+}$, 0.4 mM $Fe^{2+}$ and 0.1 mM $Mn^{2+}$ were conducted in a low gas flow agitated reactor with 100 mL/min of a saturated 98%/2% $O_2/CO_2$ gas mixture fed into the reactor headspace. The duration of the experiment is 2 weeks and 3 ml samples were taken every two to three days and water was added periodically to maintain the water balance of the reactor contents. The liquid samples were analyzed for PZ, AEP, and degradation products using ion chromatography. The details of the experimental apparatus, procedure, and analytical methods are described by Sexton (Sexton A J. Amine oxidation in $CO_2$ capture processes. The University of Texas at Austin, Austin, Tex., 2008).

Nitrosamine Formation and Decomposition

Nitrosamine formation and decomposition experiments were conducted in ⅜-inch Swagelok thermal cylinders using a similar method to thermal degradation experiments. 5 m PZ/2 m AEP or 2 m AEP solutions with 0.3 mol $CO_2$/mol alkalinity were prepared and spiked gravimetrically with 40 mmol/kg of sodium nitrite ($NaNO_2$) immediately before being placed into convection ovens at 100° C. and 150° C. The details of the experimental apparatus, procedure, and analytical methods are described by Fine (Fine N A, Rochelle G T. Managing n-nitrosopiperazine in amine scrubbing. Presented at GHGT-11, Kyoto, Japan, Nov. 18-22, 2012. *Energy Procedia*, 2013).

$CO_2$ Absorption Rate and Solubility $CO_2$ absorption rate and equilibrium partial pressure in 5 m PZ/2 m AEP were measured from 20 to 100° C. using a wetted wall column (WWC), which countercurrently contacted an aqueous 5 m PZ/2 m AEP solution with a saturated $N_2/CO_2$ stream on the surface of a stainless steel rod with a known surface area to simulate the situation of $CO_2$ absorption in a absorber. The detailed description of wetted wall column measurement has been given by Li (Li L, et al. Amine blends using concentrated piperazine. Presented at GHGT-11, Kyoto, Japan, Nov. 18-22, 2012. Energy Procedia, 2013).

High Temperature Vapor-Liquid Equilibrium

The total pressure of 5 m PZ/2 m AEP loaded with $CO_2$ was measured from 100 to 160° C. using a sealed autoclave (SA). The partial pressure of $CO_2$ was calculated by subtracting the partial pressure of $N_2$ and water from the measured total pressure. The pressure of water was assumed to follow Raoult's Law and the pressure of amine was neglected. The experimental method and calculation of $CO_2$ partial pressure are described in detail by Xu (Xu Q. Thermodynamics of $CO_2$ Loaded Aqueous Amines. The University of Texas at Austin, Austin, Tex., 2011.)

Synthesis of N-(2-aminoethyl) piperazine

The synthesis of N-(2-aminoethyl) piperazine from PZ and MEA in the presence of $CO_2$ was conducted using a method similar to that of thermal degradation experiments. 7 m PZ/2 m MEA with 0.3 mol $CO_2$/mol alkalinity was placed in ½-inch OD 316 stainless steel thermal cylinders, which were then sealed and placed in a convection oven held at 150° C. Cylinders were removed periodically and samples were analyzed using ion chromatography.

Results and Discussion

Solid Solubility of PZ/AEP

The melting transition temperature of PZ/AEP with variable amine concentration ratio (5/2, 4/2.67, 3/3.33) over a range of $CO_2$ loading from 0 to 0.4 mol/mol alkalinity is shown in FIG. 34. The transition temperature for non-blended 8 m PZ from Freeman (Freeman S A, Dugas R E, Van Wagener D H, Nguyen T, Rochelle G T. Carbon dioxide capture with concentrated, aqueous piperazine. Int J Greenh Gas Con 2010; 4(2):119-24) is also shown in FIG. 34 for comparison. As the proportion of PZ in the blend decreases, the transition temperature decreases. For 5 m PZ/2 m AEP, a $CO_2$ loading of approximately 0.20 mol/mol alkalinity is required to maintain a liquid solution without precipitation at room temperature (22° C.), which is lower than 0.25 mol/mol alkalinity required for 8 m PZ. Unlike 8 m PZ, which also precipitates when $CO_2$ loading reaches 0.44 mol $CO_2$/mol alkalinity, no precipitate was observed for the three blends at rich $CO_2$ loading (until $CO_2$ reached its solubility limit under atmospheric pressure, which is about 0.4 mol $CO_2$/mol alkalinity in the three blends). Therefore, this blend has a lower solvent solubility limit at lean loading, and is free from precipitation at rich loading under atmospheric pressure.

Viscosity

Viscosity of 5 m PZ/2 m AEP with 0.2 and 0.3 mol $CO_2$/mol alkalinity was measured at 20° C., 40° C., and 60° C. (Table 16). The results suggests that the viscosity of this blend is comparable to that of non-blended 8 m PZ (Freeman S A, Dugas R E, Van Wagener D H, Nguyen T, Rochelle G T. Carbon dioxide capture with concentrated, aqueous piperazine. Int J Greenh Gas Con 2010; 4(2):119-24) (i.e., 11.96 cP for 5 PZ/2 AEP compared to 9.99 cP for 8 m PZ at 0.30 mol $CO_2$/mol alkalinity and 40° C.). The data also demonstrate the expected trend that viscosity increases with increasing $CO_2$ concentration and decreasing temperature.

TABLE 16

Viscosity of 5 m PZ/2 m AEP from 20 to 60° C.

| $CO_2$ Loading | Viscosity (cP) | | |
|---|---|---|---|
| (mol/mol alkalinity) | 20° C. | 40° C. | 60° C. |
| 0.20 | 21.92 ± 0.068 | 9.843 ± 0.082 | 5.88 ± 0.162 |
| 0.30 | 24.75 ± 0.090 | 11.96 ± 0.108 | 7.78 ± 0.720 |

Thermal Degradation

The thermal degradation of 5 m PZ/2 m AEP was measured for 20 weeks with 0.3 mol $CO_2$/mol alkalinity at 150° C. and 175° C. After the 20-week experiment, the loss of PZ and AEP at 150° C. was approximately 10% and 30%, respectively, while at 175° C. the amines were almost entirely degraded (FIGS. 35 and 36). From these results it can be concluded that 5 m PZ/2 m AEP is thermally stable up to 150° C. but not 175° C.

The thermal degradation of 5 m PZ/2 m AEP is compared to that of 5.33 m non-blended AEP and 8 m PZ (Freeman S A, Rochelle G T. Thermal degradation of piperazine and its structural analogs. Energy Procedia 2011; 4 (2011):43-50) (FIGS. 35 and 36), and their apparent first order rate constants ($k_1$) for thermal degradation is given in Table 17, along with the data for 7 m MEA. The PZ in this blend degrades at the same rate as in 8 m PZ at both temperatures (FIG. 35). However, the AEP in the blend degraded much more slowly than in 5.33 m AEP with 0.3 mol $CO_2$/mol alkalinity (FIG. 36). This could have two explanations: 1) compared to 2 m AEP, due to the competition of PZ for $H^+$, this blend produced less protonated AEP, which is likely to be the initiating species required for the initial reactions of thermal degradation; 2) as PZ is one of the major products for AEP thermal degradation, its presence may inhibit the degradation of AEP. The overall amine degradation rate of this blend is on the same scale as that of 8 m PZ, while much smaller than that of 5.33 m AEP and 7 m MEA.

TABLE 17

Apparent first order rate constant ($k_1$) for thermal degradation of PZ/AEP and other related solvents.

| Amine | Components | Loading mol/mol alkalinity | $k_1 \times 10^{-9}$ ($s^{-1}$) | |
|---|---|---|---|---|
| | | | 150° C. | 175° C. |
| PZ | 5 m PZ/2 m AEP | 0.3 | 10.2 | 162 |
| AEP | 5 m PZ/2 m AEP | 0.3 | 27.9 | 388 |
| PZ/AEP | 5 m PZ/2 m AEP | 0.3 | 15.2 | 201 |
| [11]PZ | 8 m PZ | 0.3 | 6.1 | 140 |
| AEP | 5.33 m AEP | 0.3 | 365 | 2022 |
| [13]MEA | 7 m MEA | 0.4 | 807 | N/A |

N/A: not available

The effect of CO$_2$ on the degradation of PZ and AEP in 5 m PZ/2 m AEP at 175° C. is given in FIG. 37. The increase of CO$_2$ accelerated the degradation of both PZ and AEP in this blend. This can be ascribed to the increased protonated PZ/AEP species present in solution, which are likely to be the initiating species required for the initial reactions of thermal degradation.

The thermal degradation products of 5 m PZ/2 m AEP at 175° C. are shown in FIG. 38. It can be seen that NH$_4^+$ and total formate, the sum of formate and N-Formyl PZ, were the two major products for the thermal degradation, while 1,1'-(1,2-ethanediyl)bis-PZ (PEP), 1-Ethyl PZ, Triethylenediamine (TEDA), total 1-[2-[(2-aminoethyl)amino]ethyl] PZ (AEAEPZ), the sum of AEAEPZ and AEAEPZ Urea, and N,N"-di(2-aminoethyl) piperazine (DAEP) were the minor ones. As the retention time of TEDA is too close to that of 1-Ethyl PZ on cation ion chromatography, we quantified them as a combination. All the products showed a fast phase in the first 1-3 weeks, followed by a slow rate or steady-state concentration at longer time.

PZ, AEP, and CO$_2$ loss are compared to the production of NH$_4^+$ and total formate during thermal degradation of 5 m PZ/2 m AEP with 0.3 mol CO$_2$/mol alkalinity at 175° C. (FIG. 39). The rate of PZ/AEP decrease is much larger than the rate of NH$_4^+$ increase in the first week, indicating some degradation pathways that do not produce NH$_4^+$ may also occur in the first week. This non-NH$_4^+$ production pathway could be the reaction between two PZ molecules to produce AEAEPZ and AEAEPZ urea.

Oxidative Degradation

Sexton et al. (Sexton A J. Amine oxidation in CO$_2$ capture processes. The University of Texas at Austin, Austin, Tex., 2008) and Freeman et al. (Freeman S A. Thermal Degradation and Oxidation of Aqueous piperazine for Carbon Dioxide Capture. The University of Texas at Austin, Austin, Tex., 2011) have shown that PZ oxidizes significantly slower than MEA under similar conditions, and that the generation rate of total formate (formate and formyl amides) can represent the oxidation rate of PZ under different conditions in low gas flow experiments. In this work, oxidation of 8 m PZ, 2 m AEP and 5 m PZ/2 m AEP at 70° C. in the presence of 0.1 mM Mn$^{2+}$ and with the typical SSM mixture (0.4 mM Fe$^{2+}$, 0.05 mM Cr$^{3+}$ and 0.1 mM Ni$^{2+}$), was investigated. The generation of total formate is shown in FIG. 40, compared to that in 8 m PZ and 7 m MEA in the absence of Mn$^{2+}$ under similar conditions. It can be seen from FIG. 40 that Mn$^{2+}$ did not have a significant catalytic effect on the oxidation of PZ. In terms of the production of total formate, the oxidation of 2 m AEP and 5 m PZ/2 m AEP was comparable to that of 8 m PZ, but significantly slower than that of 7 m MEA.

Nitrosamines

Nitrosamines, which are likely to be carcinogenic and can be formed through nitrosation of secondary amines (Fine N A, Rochelle G T. Managing n-nitrosopiperazine in amine scrubbing. Presented at GHGT-11, Kyoto, Japan, Nov. 18-22, 2012. Energy Procedia, 2013), may be important when using amines containing secondary amine nitrogens in CO$_2$ capture. The formation of nitrosamines in 5 m PZ/2 m AEP was compared to that in 8 m PZ and 2 m AEP at 0.3 mol CO$_2$/mol alkalinity and 100° C. (FIG. 41). As can be seen from FIG. 41, the formation rate of total nitrosamine (mono-nitroso-PZ (MNPZ) and mono-nitroso-AEP (MNAEP)) in 5 m PZ/2 m AEP is similar to the formation rate of MNPZ in 8 m PZ. However, the formation of MNAEP in this blend is slower than that in 2 m AEP. This can be ascribed to the competition between PZ and AEP for CO$_2$ in blend. Compared to 2 m AEP, this blend produced less AEP carbamate species, which are likely to be the initiating species required for the initial reactions of nitrosation and first order to the formation rate of MNAEP.

The decomposition of nitrosamines in 5 m PZ/2 m AEP was investigated at 0.3 mol CO$_2$/mol alkalinity and 150° C., compared to that in 8 m PZ and 2 m AEP under similar conditions (FIG. 42). As can be seen from FIG. 42, the decomposition of MNPZ and MNAEP in 5 m PZ/2 m AEP is on the same scale as that of that of MNPZ in 8 m PZ. However, the decomposition of MNAEP in 5 m PZ/2 m AEP is much faster than that of MNAEP in 2 m AEP. This may be ascribed to the high amine concentration in this blend compared to 2 m AEP, though the mechanism for thermal decomposition of nitrosamine is still unclear at this moment. Together with the formation results, these results indicate that PZ/AEP may have a similar nitrosamine issue to individual PZ.

CO$_2$ Solubility

The CO$_2$ solubility in loaded 5 m PZ/2 m AEP was measured from 40 to 160° C. (FIG. 43). CO$_2$ equilibrium partial pressure, P$_{CO2}$ (Pa), was regressed using the following empirical model Eq. 1 as a function of temperature, T (K), and CO$_2$ loading, α (mol CO$_2$/mol alkalinity), in the liquid phase.

$$\ln P_{CO2} = 39.83 = 11105 * \frac{1}{T} - 15.47 * a + 22167 * \frac{a^2}{T} \quad (1)$$

The CO$_2$ partial pressure of 8 m PZ is also given in FIG. 43 for comparison. From FIG. 43, we can see that CO$_2$ partial pressure of 5 m PZ/2 m AEP is consistently higher than that of 8 m PZ from 40 to 160° C., indicating a lower CO$_2$ solubility in this blend. Based on the difference in the equilibrium CO$_2$ partial pressure from 5 to 0.5 kPa at 40° C., the working capacity of 5 m PZ/2 m AEP (0.67 mole per kg amines+water) is lower than that of 8 m PZ (0.79 mole per kg amines+water), but still much higher than that of 7 m MEA (0.47 mole per kg amines+water).

Absorption Rate

CO$_2$ absorption rate into 5 m PZ/2 m AEP were studied in a wetted wall column from 20 to 100° C. with loading from 0.25 to 0.39 mol CO$_2$/mol alkalinity. The liquid-film mass coefficients (k$_g$') of CO$_2$ absorption into 5 m PZ/2 m AEP are shown in FIG. 44. To compare kg' in 5 m PZ/2 m AEP to that in 8 m PZ on the same basis, the rate data are plotted against partial pressure of CO$_2$ instead of CO$_2$ loading. T compare kg' at variable temperature, the rate data of 5 m PZ/2 m AEP at 20 to 100° C. are plotted as a function of the equilibrium partial pressure of CO$_2$ at 40° C. Compared to 8 m PZ, at 40° C. the blend has similar rate. Similar to other amines studied in CO$_2$ capture, temperature has a negative effect on CO$_2$ absorption rate into 5 m PZ/2 m AEP, especially at rich CO$_2$ loading.

Synthesis of N-(2-aminoethyl) piperazine

Since AEP is the dominant thermal degradation product in 7 m MEA/2 m PZ, the synthesis of AEP was studied at 150° C. with an initial loading of 0.3 mol CO$_2$/mol alkalinity with two blends: 7 m PZ/2 m MEA and 6 m PZ/4 m MEA. A combined AEP/DAEP yield of 68% was obtained with 89% of the total alkalinity present as PZ, AEP, or DAEP over 840 hours in 7 m PZ/2 m MEA. A combined AEP/DAEP yield of 52% was obtained with 77% of the total alkalinity present as PZ, AEP, or DAEP in 6 m PZ/4 m MEA. Ureas appear to be the greatest contributor to alkalinity loss. These results show that PZ/AEP can be achieved by starting with PZ/MEA, leading to cost reduction in obtaining the solvent.

The blend 5 m PZ/2 m AEP has a larger solid solubility window than 8 m PZ. In 5 m PZ/2 m AEP, a CO$_2$ loading of 0.20 mol/mol alkalinity is required to avoid precipitation at 22° C., which is lower than 0.25 mol/mol alkalinity required for 8 m PZ. No precipitate was observed in PZ/AEP at rich CO$_2$ loading. The viscosity of 5 m PZ/2 m AEP is comparable to 8 m PZ.

5 m PZ/2 m AEP is thermally stable up to 150° C. but not 175° C. Thermal degradation of this blend is comparable to 8 m PZ, but significantly slower than 7 m MEA. In terms of the production of total formate, the oxidation of 5 m PZ/2 m AEP is comparable to that of 8 m PZ, but significantly slower than that of 7 m MEA, and Mn$^{2+}$ does not have a significant catalytic effect on the oxidation of PZ.

The working capacity of 5 m PZ/2 m AEP (0.67 mole per kg amines+water) is lower than that of 8 m PZ (0.79 mole per kg amines+water), but still much higher than that of 7 m MEA (0.47 mole per kg amines+water). Kinetics measurements have shown that compared to 8 m PZ, at 40° C. 5 m PZ/2 m AEP has similar CO$_2$ absorption rates. The formation and decomposition of nitrosamine in PZ/AEP is similar to that in PZ. PZ/AEP can be synthesized in situ by thermal degradation of PZ/MEA. Compared to 8 m PZ, the greater solvent solubility and comparable CO$_2$ absorption and degradation rates, indicate that 5 m PZ/2 m AEP is a superior solvent for CO$_2$ capture by absorption/stripping.

A novel blend of piperazine (PZ) with N-(2-aminoethyl) piperazine (AEP) has been proposed as a superior solvent for CO$_2$ capture from coal-fired flue gas. Blending PZ with AEP can remediate the precipitation issue of concentrated PZ while maintaining its high CO$_2$ absorption rate, and high resistance to degradation. Although PZ/AEP has a lower CO$_2$ capacity than concentrated piperazine, its higher heat of absorption may offset the negative effect on energy consumption. PZ/AEP also shows a milder nitrosamine issue than concentrated piperazine. A novel method for synthesizing AEP using PZ and monoethanolamine (MEA) was also developed to lower the solvent cost in industry application.

Example 7

In-Situ Synthesis of Useful Polyamines for CO$_2$ Capture from Piperazine

Synthesis Concept

Primary/secondary ethanolamines and propanolamines initially form oxazolidinones (thermal degradation pathway).

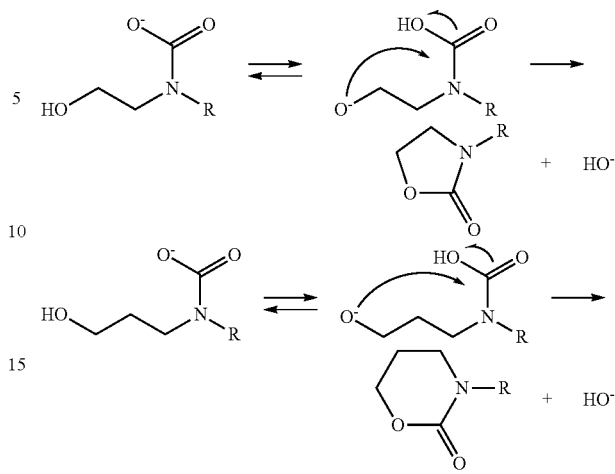

As shown below, piperazine can rapidly and selectively react with oxazolidinone to form substituted piperazines

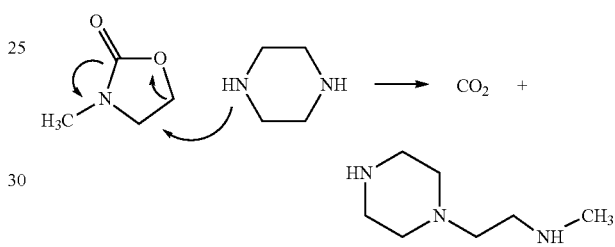

piperazine is considered to be the state of the art. It has a fast CO$_2$ absorption rate, resistance to degradation, reduced parasitic energy loss in capture plant, and limited solid solubility ranges. Substituted piperazines maintain positive characteristics of piperazine and have improved solid solubility characteristics. Most are hard to obtain in commercial quantities, but they can be made in-situ in the CO$_2$ stripping column.

Experimental Methods/Apparatus

Reagents measured gravimetrically. A solution was sparged with CO$_2$, measured gravimetrically. The initial concentration used was 7 m piperazine/2 m oxazolidinone-forming amine, 0.3 mol CO$_2$/mol N. Sealed Swagelok® stainless-steel batch reactors, convection ovens held at constant temperature, Cation Chromatography (Dionex ICS-2100), Potentiometric Titration (Metrohm Titrando) were used in these experiments. The following table lists the amines tested.

TABLE 18

Amines Tested

| Amine | Structure | Oxazolidinone Structure | Primary Synthesis Product |
|---|---|---|---|
| Monoethanol amine (MEA) | H$_2$N–CH$_2$CH$_2$–OH | (oxazolidinone) | (HN-piperazine-N-CH$_2$CH$_2$-NH$_2$) |
| Methylamino ethanol (MAE) | H$_2$N–NH–CH$_2$CH$_2$–OH | H$_3$C–(oxazolidinone) | (HN-piperazine-N-CH$_2$CH$_2$-NH-CH$_3$) |

TABLE 18-continued

Amines Tested

| Amine | Structure | Oxazolidinone Structure | Primary Synthesis Product |
|---|---|---|---|
| Monoisopropanol amine (MIPA) | H₂N–CH₂–CH(OH)–CH₃ | 5-methyl-oxazolidinone | piperazine with –CH(CH₃)–CH₂–NH₂ substituent |
| 2-Amino-2-methyl-1-propanol (AMP) | H₂N–C(CH₃)₂–CH₂OH | 4,4-dimethyl-oxazolidinone | piperazine with –CH₂–C(CH₃)₂–NH₂ substituent |
| Monopropanol amine (MPA) | H₂N–CH₂–CH₂–CH₂–OH | 6-membered cyclic carbamate | piperazine with –(CH₂)₃–NH₂ substituent |

Modeling Reaction Kinetics

First-order rate behavior models amine conversion well.

$$-r_A = k \ast C_A$$

Arrhenius Temperature Dependency was assumed.

$$k = A \ast \exp\left(\frac{-E_A}{R \ast T}\right)$$

FIG. 45 shows the concentration of MAE over time, which indicates first order conversion behavior at 150° C. The initial conditions were 7 m PZ/2 m MAE amine, 0.3 mol $CO_2$/mol N. FIG. 46 shows the concentration of PZ-MAE synthesis product and parent amines under initial conditions 7 m PZ/2 m MAE, 150° C., 0.3 mol $CO_2$/mol N. FIG. 46 demonstrates thermal stability of synthesis product. FIG. 47 shows comparison of conversion Rates for Various Amines. Initial conditions were 7 m PZ/2 m amine, 0.3 mol $CO_2$/mol N. Table 19 summarizes the results of these experiments.

TABLE 19

Summary of Results

| | H₂N–CH₂–CH₂–OH | H₂N–(CH₂)₃–OH | H₂N–CH₂–CH(OH)–CH₃ | H₂N–C(CH₃)₂–CH₂OH | H₃C–NH–CH₂–CH₂–OH |
|---|---|---|---|---|---|
| Conversion (at 500 hours) | 85% | 45% | 44% | 28% | 100%* |
| Synthesis Product Selectivity (500 hours) | 69% | >90% | 87%^ | 93% | >90% |
| Alkalinity Loss, %/week | 2.0 | 1.7 | 1.5 | 1.0 | 5.0* |
| 1ˢᵗ-Order Amine Conversion Rate, 1/hr | 0.0042 | 0.0012 | 0.00088 | 0.00067 | 0.017 |
| Activation Energy, kJ/mol | 160 | 150 | 130 | 140 | 100 |

Thus, piperazine can rapidly and selectively react with oxazolidinones to form substituted piperazines. Substituted piperazines formed via synthesis are thermally stable. Increased steric hindrance or chain length of oxazolidinone-former reduces synthesis rate. Increased steric hindrance increases selectivity to synthesis products. Secondary oxazolidinone-forming amines have greater conversion rates compared to primary oxazolidinone-forming amines.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

REFERENCES

[1] Rochelle G T, et al. Aqueous piperazine as the new standard for $CO_2$ capture technology. *Chemical Engineering Journal* 2011; 171:725-733.

[2] Oyenekan B A, Rochelle G T. Alternative stripper configurations for $CO_2$ capture by aqueous amines. *American Institute of Chemical Engineering Journal* 2007; 53 (12): 3144-3154.

[3] Van Wagner D H, Rochelle G T. Stripper configurations for $CO_2$ capture by aqueous monoethanolamine. *Chemical Engineering Research and Design* 2010; 89 (9): 1639-1646.

[4] Chen X, Closmann F, Rochelle G T. Accurate Screening of Amines by the Wetted Wall Column. *Energy Procedia*. 2011; 4: 101-108.e

[5] Dugas R. *Carbon dioxide absorption, desorption, and diffusion in aqueous piperazine and monoethanolamine*. PhD Dissertation, The University of Texas at Austin, Austin, Tex., 2009

[6] Freeman S A, et al. Carbon dioxide capture with concentrated, aqueous piperazine. *Energy Procedia* 2009; 1(1): 1489-1496.

[7] Li H, Li L, Nguyen T, Rochelle G T, Chen J. Characterization of piperazine/2-aminomethylpropanol. *Energy Procedia* 2013; Presented at GHGT-11, Kyoto, Japan, Nov. 18-22, 2012. Energy Procedia, 2013.

[8] Du Y, et al. Aqueous piperazine/N-(2-aminoethyl)piperazine for $CO_2$ capture. *Energy Procedia* 2013; Presented at GHGT-11, Kyoto, Japan, Nov. 18-22, 2012. Energy Procedia, 2013.

[9] Xu Q. *Thermodynamics of $CO_2$ loaded aqueous amines*. The University of Texas at Austin, Austin, Tex., 2011.

[10] Freeman S A. *Thermal degradation and oxidation of aqueous piperazine for carbon dioxide capture*. PhD Dissertation, The University of Texas at Austin, Austin, Tex., 2010.

[11] Namjoshi 0, Du Y, Rochelle G T. Thermal degradation of piperazine blends with diamines. Presented at GHGT-11, Kyoto, Japan, Nov. 18-22, 2012. *Energy Procedia*, 2013.

[12] Li L, Li H, Du Y, Namjoshi O, Rochelle G T. Absorption rates and $CO_2$ solubility in new piperazine blends. Presented at GHGT-11, Kyoto, Japan, Nov. 18-22, 2012. *Energy Procedia*, 2013.

[13] Rochelle G T, et al. Acidic gas removal by aqueous amine solvents. US Patent 2011/0171093 A1. Jul. 14, 2011.

[14] Oyenekan B A, Rochelle G T. Energy performance of stripper configurations for $CO_2$ capture by aqueous amines. *Industrial & Engineering Chemistry Research* 2006; 45(8): 2457-2464.

[15] Davis J. *Thermal degradation of aqueous amines used for carbon dioxide captuer*. PhD Dissertation, The University of Texas at Austin, Austin, Tex., 2009.

[16] Nguyen T, Hillard M, Rochelle G T. Amine volatility in $CO_2$ capture. *International Journal of Greenhouse Gas Control* 2010; 4 (5) 707-715

[17] DIPPR, 1998-Provo, Utah: BYU DIPPR, Thermophysical Properties Laboratory, 1998-Version 13.0.

[18] Colburn A P, du Pont de E I. Mean temperature difference and heat transfer coefficient in liquid heat exchangers. *Industrial and Engineering Chemistry*, 1933; 25(8): 873-877.

[19] Sexton A J, Rochelle G T. Reaction Products from the Oxidative Degradation of Monoethanolamine. *Industrial & Engineering Chemistry Research*, 2011; 50 (2): 667-673

[20] Closmann F B. *Oxidation and thermal degradation of methyldiethanolamine/piperazine in $CO_2$ capture*. The University of Texas at Austin. Ph.D. Dissertation. 2011.

[21] Sherman B, et al. Carbon capture with 4 m piperazine/4 m 2-methylpiperazine. Presented at GHGT-11, Kyoto, Japan, Nov. 18-22, 2012. *Energy Procedia*, 2013.

[22] Rochelle G T. Amine Scrubbing for $CO_2$ Capture. *Science* 2009; 325(5948):1652-4.

[23] Freeman S A, Dugas R E, Van Wagener D H, Nguyen T, Rochelle G T. Carbon dioxide capture with concentrated, aqueous piperazine. *Int J Greenh Gas Con* 2010; 4(2):119-24.

[24] Hilliard M D. A Predictive Thermodynamic Model for an Aqueous Blend of Potassium Carbonate, piperazine, and Monoethanolamine for Carbon Dioxide Capture from Flue Gas. The University of Texas at Austin, Austin, Tex., 2008.

[25] Freeman S A. Thermal Degradation and Oxidation of Aqueous piperazine for Carbon Dioxide Capture. The University of Texas at Austin, Austin, Tex., 2011.

[26] Freeman S A, Rochelle G T. Thermal Degradation of Aqueous piperazine for $CO_2$ Capture: 2. Product Types and Generation Rates. *Ind Eng Chem Res* 2012; 51(22):7726-35.

[27] Sexton A J. Amine oxidation in $CO_2$ capture processes. The University of Texas at Austin, Austin, Tex., 2008.

[28] Fine N A, Rochelle G T. Managing n-nitrosopiperazine in amine scrubbing. Presented at GHGT-11, Kyoto, Japan, Nov. 18-22, 2012. *Energy Procedia*, 2013.

[29] Li L, et al. Amine blends using concentrated piperazine. Presented at GHGT-11, Kyoto, Japan, Nov. 18-22, 2012. *Energy Procedia*, 2013.

[30] Freeman S A, Rochelle G T. Thermal degradation of piperazine and its structural analogs. *Energy Procedia* 2011; 4 (2011):43-50.

[31] Davis J D, Rochelle G T. Thermal degradation of monoethanolamine at stripper conditions. *Energy Procedia* 2009; 1 (2009):327-33.

[32] Chen X, Rochelle G T. Aqueous piperazine derivatives for $CO_2$ capture: Accurate screening by a wetted wall column. *Chem Eng Res Des* 2011; 89 (2011):1693-710.

What is claimed is:

1. A method comprising contacting an acidic gas with an aqueous amine solvent, wherein the aqueous amine solvent comprises piperazine and a linear diamine, wherein the linear diamine is 3-oxapentane-1,5-diamine, and wherein the 3-oxapentane-1,5-diamine is present in the aqueous amine solvent at a concentration in the range of from about 4 to about 12 equivalents/kg water.

2. The method of claim 1 wherein 50 mol % or less of the amine in the solvent is the linear diamine.

3. The method of claim 1 further comprising flowing the solvent to a stripper operating at a temperature in the range of from about 120° C. to about 165° C.

4. A method comprising contacting an acidic gas with a blend comprising piperazine, diaminoethylpiperazine and aminoethylpiperazine.

5. The method of claim 4 wherein the amine concentration of the blend is in the range of from about 8 to about 24 equivalents/kg water and wherein 50 mol % or less of the amine in the blend is aminoethylpiperazine.

6. The method of claim 4 further comprising flowing the blend to a stripper operating at a temperature in the range of from about 120° C. to about 165° C.

7. The method of claim 6 wherein the blend composition has reached equilibrium at the operating temperature of the stripper.

* * * * *